United States Patent
Baileykobayashi et al.

(10) Patent No.: US 11,299,555 B2
(45) Date of Patent: Apr. 12, 2022

(54) METHOD FOR DIAGNOSING ALZHEIMER'S DISEASE USING SIGNAL PEPTIDE AS INDICATOR

(71) Applicants: TOAGOSEI CO., LTD., Tokyo (JP); NATIONAL UNIVERSITY CORPORATION NAGOYA UNIVERSITY, Aichi (JP)

(72) Inventors: Nahoko Baileykobayashi, Tsukuba (JP); Makoto Sawada, Nagoya (JP); Tetsuhiko Yoshida, Tsukuba (JP)

(73) Assignees: Toagosei Co., LTD, Tokyo (JP); National University Corporation Nagoya University, Aichi (JP)

( * ) Notice: Subject to any disclaimer, the term of this patent is extended or adjusted under 35 U.S.C. 154(b) by 320 days.

(21) Appl. No.: 16/081,189

(22) PCT Filed: Mar. 2, 2017

(86) PCT No.: PCT/JP2017/008331
§ 371 (c)(1),
(2) Date: Aug. 30, 2018

(87) PCT Pub. No.: WO2017/150680
PCT Pub. Date: Sep. 8, 2017

(65) Prior Publication Data
US 2019/0071520 A1 Mar. 7, 2019

(30) Foreign Application Priority Data

Mar. 3, 2016 (JP) .............................. JP2016-041052

(51) Int. Cl.
*C07K 17/08* (2006.01)
*G01N 27/62* (2021.01)
(Continued)

(52) U.S. Cl.
CPC ............. *C07K 17/08* (2013.01); *G01N 27/62* (2013.01); *G01N 33/6851* (2013.01);
(Continued)

(58) Field of Classification Search
CPC .... C07K 17/08; C07K 14/47; G01N 33/6851; G01N 27/62; G01N 27/622; G01N 27/623;
(Continued)

(56) References Cited

U.S. PATENT DOCUMENTS 7,179,606 B2 * 2/2007 Jackowski ............. C07K 16/00
435/7.1
9,678,086 B2 * 6/2017 Van Eyk ............. G01N 33/6848
(Continued)

FOREIGN PATENT DOCUMENTS

EP 1522856 A1 * 4/2005 ........... C07K 14/595
JP 2011016763 A 1/2011
(Continued)

OTHER PUBLICATIONS

Naslund, J. et al., "Relative Abundance of Alzheimer Abeta Amyloid Peptide Variants in Alzheimer Disease and Normal Aging," Proc. Natl. Acad. Sci. (1994) 91:8378-8382 (Year: 1994).*
(Continued)

*Primary Examiner* — Jesse P Frumkin
(74) *Attorney, Agent, or Firm* — Occhiuti & Rohlicek LLP

(57) ABSTRACT

This method for aiding Alzheimer's detection provided by the present invention includes: determining a profile of signal peptides contained in a bodily fluid from a test subject, and comparing the signal peptide profile thus determined for the test subject with a previously-determined profile of signal peptides in a bodily fluid from a healthy subject. A difference between the signal peptide profile of
(Continued)

the test subject and the signal peptide profile of the healthy subject at a specific molecular weight is then associated with the test subject's suffering from or developing Alzheimer's.

3 Claims, 6 Drawing Sheets

Specification includes a Sequence Listing.

(51) Int. Cl.
   *G01N 33/68* (2006.01)
   *C07K 14/47* (2006.01)

(52) U.S. Cl.
   CPC ......... *G01N 33/6896* (2013.01); *C07K 14/47* (2013.01); *G01N 2800/2821* (2013.01); *G01N 2800/60* (2013.01)

(58) Field of Classification Search
   CPC ....... G01N 33/6896; G01N 2800/2821; G01N 2800/60
   See application file for complete search history.

(56) References Cited

U.S. PATENT DOCUMENTS

| | | | |
|---|---|---|---|
| 2005/0244904 A1 | 11/2005 | Ng | |
| 2009/0055100 A1* | 2/2009 | Cahill | C12Y 102/01012 702/19 |
| 2010/0036094 A1* | 2/2010 | Mischak | G01N 33/6896 530/350 |
| 2010/0159486 A1* | 6/2010 | Liotta | G01N 33/6896 435/7.92 |
| 2015/0353637 A1* | 12/2015 | Wang | G01N 33/6863 424/139.1 |
| 2017/0082579 A1 | 3/2017 | Sawada | |
| 2020/0005905 A1* | 1/2020 | Sawada | H01J 49/0036 |

FOREIGN PATENT DOCUMENTS

| | | |
|---|---|---|
| JP | 5422785 | 12/2013 |
| WO | 2015178249 | 11/2015 |
| WO | 2016032319 | 3/2016 |

OTHER PUBLICATIONS

Perugia, Emanuel. "Towards an understanding of the serum amyloid A (SAA) protein amyloid formation." The Weizmann Institute of Science (Israel), ProQuest Dissertations Publishing, 2009. (Year: 2009).*

Hye, Abdul, Joanna Riddoch-Contreras, Alison L. Baird, Nicholas J. Ashton, Chantal Bazenet, Rufina Leung, Eric Westman et al. "Plasma proteins predict conversion to dementia from prodromal disease." Alzheimer's & Dementia 10, No. 6 (2014): 799-807.

Butterfield, D. Allan, Liqing Gu, Fabio Di Domenico, and Rena AS Robinson. "Mass spectrometry and redox proteomics: applications in disease." Mass spectrometry reviews 33, No. 4 (2014): 277-301.

Japanese Office Action dated Feb. 18, 2021 in JP Application No. 2018-503407.

* cited by examiner

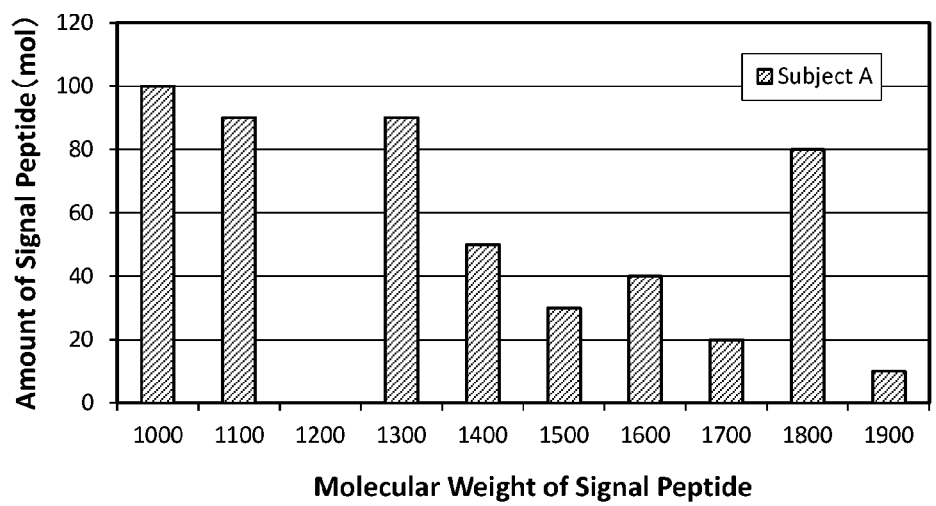
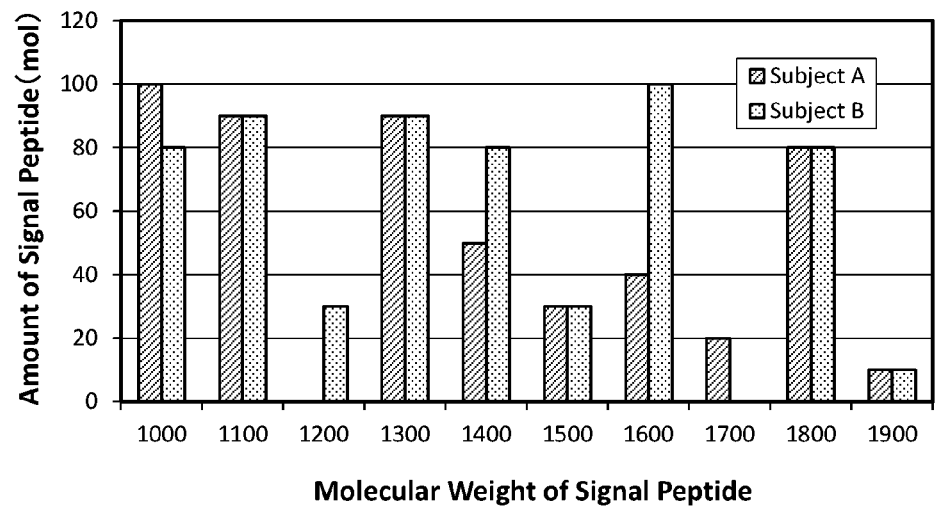

METHOD FOR DIAGNOSING ALZHEIMER'S DISEASE USING SIGNAL PEPTIDE AS INDICATOR

CROSS REFERENCE TO RELATED APPLICATIONS

This application is a National Phase under 35 USC 371 of International Application No. PCT/JP2017/008331 filed on Mar. 2, 2017, which claims priority to Japanese Application No. 2016-041052 filed on Mar. 3, 2016, the contents of which are hereby incorporated by reference in their entirety.

TECHNICAL FIELD

The present invention relates to a method for diagnosing Alzheimer's disease using a signal peptide as an indicator.

The priority claim for this application is based on Japanese Patent Application No. 2016-041052 filed on Mar. 3, 2016, and the entire contents of that Japanese application are herein incorporated by reference.

BACKGROUND ART

Neurodegenerative diseases are diseases involving impairment of specific nerves, and are characterized by symptoms of reduced cognitive function, ataxia, and involuntary movement. Such neurodegenerative diseases include Alzheimer's disease, Parkinson's disease, amyotrophic lateral sclerosis and the like.

Alzheimer's disease is a neurodegenerative disease involving impairment of neurons associated with higher brain function, and is a cause of dementia. The principal clinical symptoms of Alzheimer's disease include symptoms of cognitive impairment such as memory impairment, language disorders and apraxia, personality changes such as violent behavior and speech, and abnormal behaviors such as wandering and the like.

Many of these clinical symptoms associated with Alzheimer's disease are also common to other cognitive disorders, and it is extremely difficult to make a definite diagnosis of Alzheimer's disease based on such clinical symptoms. Consequently, diagnosing Alzheimer's disease normally means making a comprehensive judgment (diagnosis) based on the results of multiple tests, including interviews, tests to assess cognitive function (for example, neuropsychological evaluations such as the mini-mental state examination (MMSE)), and brain imaging (CT, MRI, etc.).

CITATION LIST

Patent Literature

Patent Literature 1: Japanese Patent No. 5422785

Non Patent Literature

Non Patent Literature 1: Alzheimer and Dementia, Vol. 10, 2014, pp. 799-807

SUMMARY OF INVENTION

Technical Problem

However, even if a diagnosis is based on a combination of the results of the multiple tests described above, it is still difficult to diagnose Alzheimer's disease with a high degree of accuracy. Even specialists are at risk of overlooking Alzheimer's disease (diagnosing it as another disease).

Moreover, the tests to assess cognitive function (for example, neuropsychological evaluations such as the mini-mental state examination (MMSE)) are often time-consuming to administer, and tend to be burdensome for both the patient and the medical institution. Furthermore, these tests to assess cognitive function are used principally for dementia screening, and are not very accurate (sensitive or specific) as a method for diagnosing Alzheimer's disease.

In addition, brain imaging requires specialized and expensive medical equipment, and can only be performed at a limited number of medical facilities. Judging the results of such imaging is also an advanced skill.

At present, the only way to obtain a definite diagnosis of Alzheimer's is to perform an autopsy after the patient's death and confirm the presence of senile plaques and neurofibrillary tangles, which are pathological features specific to Alzheimer's. However, confirming pathological features of the brain is extremely difficult when diagnosing living patients.

Under these circumstances, there has been demand in recent years for the identification and use of biomarkers that can provide useful information for Alzheimer's diagnosis. The specificity and sensitivity of diagnosis can be expected to improve when Alzheimer's is diagnosed with such biomarkers.

For example, according to Non Patent Literature 1 the abundance of specific proteins contained in cerebrospinal fluid (CSF) differs between Alzheimer's patients and healthy individuals.

However, although there have been numerous studies into the identification and use of useful biomarkers for diagnosing Alzheimer's, none has yet been incorporated into routine clinical testing due to problems of accuracy, reliability and the like.

It is an object of the present invention to provide a new method that can aid in the detection of Alzheimer's, as well as a biomarker for use in this method. It is another object to provide an Alzheimer's testing composition and Alzheimer's testing kit for use in this method for aiding detection of Alzheimer's.

Solution to Problem

The inventors conducted numerous studies of signal peptides present in bodily fluids in the course of intensive research aimed at establishing methods of diagnosing Alzheimer's using such signal peptides as indicators. As a result, we discovered differences in the presence and absence and abundance of specific signal peptides between the bodily fluids of Alzheimer's patients and the bodily fluids of healthy subjects. We then perfected the present invention after finding that useful data for diagnosing Alzheimer's could be obtained by using these specific signal peptides as indicators.

First, the inventors discovered that the profiles of signal peptides in the bodily fluids of Alzheimer's patients differed from the profiles of signal peptides in the bodily fluids of healthy subjects. Therefore, the first embodiment of the present invention provides a method for aiding Alzheimer's detection, the method including: determining a profile of signal peptides in a molecular weight range of 1000 to 3500 from signal peptides contained in a bodily fluid from a test subject; and comparing the signal peptide profile thus determined for the test subject with a previously-determined profile of signal peptides in bodily fluid from a healthy subject. In this method, a difference between the signal peptide profile of the test subject and the signal peptide profile of the healthy subject at any of the following molecular weights is associated with the test subject's suffering from or developing Alzheimer's (typically, the difference suggests that the test subject suffers from or has developed Alzheimer's):
1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1620.77±2, 1622.09±2, 1629.17±2, 1632.48±2, 1642.66±2, 1675.65±2, 1687.50±2, 1690.86±2, 1692.39±2, 1694.78±2, 1717.35±2, 1724.64±2, 1731.08±2, 1736.78±2, 1767.38±2, 1779.67±2, 1784.07±2, 1786.71±2, 1791.82±2, 1800.02±2, 1801.91±2, 1821.62±2, 1841.19±2, 1860.98±2, 1865.22±2, 1867.67±2, 1868.76±2, 1875.59±2, 1876.11±2, 1883.01±2, 1900.43±2, 1906.28±2, 1933.29±2, 1936.24±2, 1958.71±2, 1966.43±2, 1966.96±2, 1980.85±2, 1994.59±2, 1996.12±2, 1996.79±2, 2005.98±2, 2084.90±2, 2090.75±2, 2102.82±2, 2121.37±2, 2133.94±2, 2134.56±2, 2135.18±2, 2137.45±2, 2159.33±2, 2169.86±2, 2187.30±2, 2196.08±2, 2196.64±2, 2240.20±2, 2257.07±2, 2261.04±2, 2269.26±2, 2292.01±2, 2302.72±2, 2330.24±2, 2331.10±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2539.62±2, 2540.74±2, 2543.60±2, 2545.55±2, 2553.90±2, 2594.54±2, 2620.55±2, 2621.08±2, 2629.71±2, 2631.23±2, 2635.51±2, 2659.81±2, 2673.96±2, 2674.65±2, 2698.27±2, 3319.44±2, 3353.34±2.

In this Description, a "signal peptide profile" is a data set relating to the presence status of multiple signal peptides (whether the signal peptides are present, and the degree of abundance thereof) within a specific molecular weight range. Typically, the multiple signal peptides are distinguished (classified) based on their molecular weights.

Such a signal peptide profile can be determined by mass spectrometry for example, and represented as a mass spectrum. The signal peptide profile can also be determined by another analysis method based on the physiochemical properties or biochemical properties of the signal peptides. For example, the signal peptides can be determined based on differences in their electrophoretic properties in two-dimensional electrophoresis, and represented in the form of multiple spots confirmed on a two-dimensional electrophoresis gel. Alternatively, the signal peptide profile can be determined by immunological methods using antibodies to the signal peptides (preferably using a protein microarray capable of analyzing multiple proteins simultaneously).

This signal peptide profile need not include data relating to all signal peptides present within a specific molecular weight range, and need only include data relating to signal peptides with molecular weights that are subject to comparison. Thus, the signal peptide profile includes data relating to 2 or 3 or more, or at least 5, or at least 10, or at least 20, or at least 30, or at least 40, or at least 50, or at least 60, or at least 70, or at least 80, or at least 90, or at least 100 signal peptides.

In the method for aiding Alzheimer's detection disclosed here, useful data for judging whether or not a test subject suffers from or has developed Alzheimer's can be obtained by a simple method in which a profile of signal peptides contained in a bodily fluid from the test subject is determined, and this signal peptide profile is compared with the signal peptide profile from the healthy subject. This method for aiding Alzheimer's detection can be used favorably for predicting, diagnosing (early diagnosis) and initiating treatment for Alzheimer's, and as a follow-up indicator after the start of treatment (typically, as an indicator for evaluating the effects of treatment).

Because this method is an in vitro test using a bodily fluid collected from a test subject, it does not require that the test subject (patient) personally appear at a facility capable of obtaining the signal peptide profile from the bodily fluid. Thus, the method for aiding Alzheimer's detection described here can be implemented at many medical facilities.

Moreover, with this method the likelihood that a test subject suffers from or has developed Alzheimer's is indicated as the result of a comprehensive analysis of the determined signal peptide profile. Therefore, this method can provide highly reliable data for diagnosing Alzheimer's.

The inventors have confirmed that the likelihood that a test subject suffers from or has developed Alzheimer's is greater when certain signal peptides specified by specific molecular weights are more abundant in the signal peptide profile of the test subject. That is, in a preferred embodiment of the method for aiding Alzheimer's detection disclosed here as the first embodiment, an increase in abundance of a signal peptide specified by any of following molecular weights in the signal peptide profile of the test subject in comparison with the signal peptide profile of the healthy subject is associated with the test subject's suffering from or developing Alzheimer's (typically, suggests that the test subject suffers from or has developed Alzheimer's):
1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1622.09±2, 1629.17±2, 1632.48±2, 1642.66±2, 1675.65±2, 1687.50±2, 1690.86±2, 1717.35±2, 1724.64±2, 1731.08±2, 1736.78±2, 1767.38±2, 1779.67±2, 1784.07±2, 1786.71±2, 1791.82±2, 1800.02±2, 1821.62±2, 1841.19±2, 1860.98±2, 1865.22±2, 1876.11±2, 1883.01±2, 1900.43±2, 1906.28±2, 1936.24±2, 1958.71±2, 1966.43±2, 1980.85±2, 1994.59±2, 1996.79±2, 2005.98±2, 2084.90±2, 2090.75±2, 2102.82±2, 2134.56±2, 2137.45±2, 2159.33±2, 2169.86±2, 2196.64±2, 2240.20±2, 2257.07±2, 2261.04±2, 2292.01±2, 2302.72±2, 2330.24±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2540.74±2, 2543.60±2, 2545.55±2, 2553.90±2, 2594.54±2, 2621.08±2, 2629.71±2, 2635.51±2, 2659.81±2, 2674.65±2, 2698.27±2, 3319.44±2.

The inventors have also confirmed that the likelihood that a test subject suffers from or has developed Alzheimer's is greater when certain signal peptides specified by specific molecular weights are less abundant in the signal peptide profile of the test subject. That is, in a preferred embodiment of the method for aiding Alzheimer's detection disclosed here as the first embodiment, a decrease in abundance of a signal peptide specified by any of following molecular weights in the signal peptide profile of the test subject in comparison with the signal peptide profile of the healthy subject is associated with the test subject's suffering from or developing Alzheimer's (typically, suggests that the test subject suffers from or has developed Alzheimer's):
1620.77±2, 1692.39±2, 1694.78±2, 1801.91±2, 1867.67±2, 1868.76±2, 1875.59±2, 1933.29±2, 1966.96±2, 1996.12±2, 2121.37±2, 2133.94±2, 2135.18±2, 2187.30±2, 2196.08±2, 2269.26±2, 2331.10±2, 2539.62±2, 2620.55±2, 2631.23±2, 2673.96±2, 3353.34±2.

In a preferred embodiment of the method for aiding Alzheimer's detection disclosed here as the first embodiment, the signal peptide profile is determined with a mass spectrometer.

Comprehensive analysis of signal peptides in bodily fluid can be accomplished easily and with a high degree of accuracy by using a mass spectrometer. That is, a profile of signal peptides in a bodily fluid can be determined easily and with a high degree of accuracy by using a mass spectrometer.

Patent Literature 1 describes a method for using mass spectrometry to detect cancer, but does not describe detecting Alzheimer's.

In another preferred embodiment of the method for aiding Alzheimer's detection disclosed here as the first embodiment, a bodily fluid from a test subject is immobilized on a thermoplastic resin before the signal peptide profile is determined, and the profile of signal peptides present in the bodily fluid immobilized on the thermoplastic resin is determined by a matrix assisted laser desorption/ionization-time-of-flight mass spectrometry (MALDI-TOFMS).

Conventionally, it was believed that when a sample immobilized on a thermoplastic resin is irradiated with an ionizing laser to perform mass spectrometry, the thermoplastic resin on which the sample is immobilized is ionized together with the sample, reducing the accuracy of the mass spectrometry. However, the inventors' researches have confirmed that ionization of signal peptides can be promoted and accurate mass spectrometry can be accomplished by performing mass spectrometry with a bodily fluid to be analyzed immobilized on a thermoplastic resin.

That is, even when a bodily fluid contains signal peptides that are difficult to ionize, a signal peptide profile that includes these signal peptides can be determined favorably by analysis using MALDI-TOFMS with the bodily fluid immobilized on a thermoplastic resin.

After further research into signal peptide profiles in the bodily fluids of Alzheimer's patients, the inventors confirmed that body fluids from Alzheimer's patients and body fluids from healthy subjects differ in the degree of abundance of specific signal peptides.

Thus, the second embodiment of the present invention provides a method for aiding Alzheimer's detection, the method including: testing the presence or absence of an Alzheimer's-associated signal peptide, or a degree of abundance of the Alzheimer's-associated signal peptide when the Alzheimer's-associated signal peptide is present in a bodily fluid derived from a test subject.

This Alzheimer's-associated signal peptide is a signal peptide, the presence or absence or degree of abundance of which in a bodily fluid from an Alzheimer's patient differs from the presence or absence of the same signal peptide in a bodily fluid from a healthy subject or from a reference level set for the degree of abundance thereof. The molecular weight of this Alzheimer's-associated signal peptide is:
$1474.95\pm2$, $1497.91\pm2$, $1516.00\pm2$, $1532.22\pm2$, $1534.67\pm2$, $1536.19\pm2$, $1544.01\pm2$, $1556.44\pm2$, $1559.85\pm2$, $1561.62\pm2$, $1591.89\pm2$, $1592.66\pm2$, $1611.67\pm2$, $1620.77\pm2$, $1622.09\pm2$, $1629.17\pm2$, $1632.48\pm2$, $1642.66\pm2$, $1675.65\pm2$, $1687.50\pm2$, $1690.86\pm2$, $1692.39\pm2$, $1694.78\pm2$, $1717.35\pm2$, $1724.64\pm2$, $1731.08\pm2$, $1736.78\pm2$, $1767.38\pm2$, $1779.67\pm2$, $1784.07\pm2$, $1786.71\pm2$, $1791.82\pm2$, $1800.02\pm2$, $1801.91\pm2$, $1821.62\pm2$, $1841.19\pm2$, $1860.98\pm2$, $1865.22\pm2$, $1867.67\pm2$, $1868.76\pm2$, $1875.59\pm2$, $1876.11\pm2$, $1883.01\pm2$, $1900.43\pm2$, $1906.28\pm2$, $1933.29\pm2$, $1936.24\pm2$, $1958.71\pm2$, $1966.43\pm2$, $1966.96\pm2$, $1980.85\pm2$, $1994.59\pm2$, $1996.12\pm2$, $1996.79\pm2$, $2005.98\pm2$, $2084.90\pm2$, $2090.75\pm2$, $2102.82\pm2$, $2121.37\pm2$, $2133.94\pm2$, $2134.56\pm2$, $2135.18\pm2$, $2137.45\pm2$, $2159.33\pm2$, $2169.86\pm2$, $2187.30\pm2$, $2196.08\pm2$, $2196.64\pm2$, $2240.20\pm2$, $2257.07\pm2$, $2261.04\pm2$, $2269.26\pm2$, $2292.01\pm2$, $2302.72\pm2$, $2330.24\pm2$, $2331.10\pm2$, $2339.45\pm2$, $2340.89\pm2$, $2345.00\pm2$, $2385.34\pm2$, $2432.63\pm2$, $2452.57\pm2$, $2475.26\pm2$, $2497.02\pm2$, $2506.70\pm2$, $2515.58\pm2$, $2532.19\pm2$, $2539.62\pm2$, $2540.74\pm2$, $2543.60\pm2$, $2545.55\pm2$, $2553.90\pm2$, $2594.54\pm2$, $2620.55\pm2$, $2621.08\pm2$, $2629.71\pm2$, $2631.23\pm2$, $2635.51\pm2$, $2659.81\pm2$, $2673.96\pm2$, $2674.65\pm2$, $2698.27\pm2$, $3319.44\pm2$ or $3353.34\pm2$.

With this method, the likelihood that a test subject suffers from or has developed Alzheimer's can be easily investigated by a simple method in which the presence or absence of the Alzheimer's-associated signal peptide, or the abundance thereof when present, is tested for a bodily fluid from the test subject. This method for aiding Alzheimer's detection can be used favorably for predicting, diagnosing (early diagnosis) and initiating treatment for Alzheimer's, and as a follow-up indicator after the start of treatment (typically, as an indicator for evaluating the effects of treatment).

Because this method is an in vitro test method in which the object of testing is a bodily fluid collected from a test subject, it does not require that the subject (patient) personally appear at a facility capable of testing the presence or absence or degree of abundance of the signal peptide in the bodily fluid. Thus, the method for aiding Alzheimer's detection described here can be implemented at many medical facilities.

In a preferred embodiment of the method for aiding Alzheimer's detection disclosed here as the second embodiment, the amino acid sequence constituting the Alzheimer's-associated signal peptide is any of the amino acid sequences represented by SEQ ID NOS: 1 to 624.

A signal peptide comprising any of the amino acid sequences represented by SEQ ID NOS: 1 to 624 is a typical example of a signal peptide corresponding to the molecular weight of the Alzheimer's-associated signal peptide. That is, the signal peptides comprising the amino acid sequences represented by SEQ ID NOS: 1 to 624 above are suitable as the Alzheimer's-associated signal peptide.

The Alzheimer's-associated signal peptide disclosed here is a signal peptide the presence or absence or degree of abundance of which in a bodily fluid from an Alzheimer's patient has been confirmed by the inventors to differ from the presence or absence of the same signal peptide in a bodily fluid from a healthy subject, or from a reference level set for the degree of abundance thereof. Thus, this Alzheimer's-associated signal peptide can be used as a biomarker for diagnosing Alzheimer's.

That is, the present invention provides a biomarker for use in diagnosing Alzheimer's. This biomarker is a signal peptide comprising any of the amino acid sequences represented by SEQ ID NOS: 1 to 624.

In another preferred embodiment of the method for aiding Alzheimer's detection disclosed here as the second embodiment, the degree of abundance of any of the Alzheimer's-associated signal peptides having following molecular weights out of the tested Alzheimer's-associated signal peptides in a bodily fluid from a test subject is confirmed to be higher than the reference level thereof:
$1474.95\pm2$, $1497.91\pm2$, $1516.00\pm2$, $1532.22\pm2$, $1534.67\pm2$, $1536.19\pm2$, $1544.01\pm2$, $1556.44\pm2$, $1559.85\pm2$, $1561.62\pm2$, $1591.89\pm2$, $1592.66\pm2$, $1611.67\pm2$, $1622.09\pm2$, $1629.17\pm2$, $1632.48\pm2$, $1642.66\pm2$, $1675.65\pm2$, $1687.50\pm2$, $1690.86\pm2$, $1717.35\pm2$, $1724.64\pm2$, $1731.08\pm2$, $1736.78\pm2$, $1767.38\pm2$, $1779.67\pm2$, $1784.07\pm2$, $1786.71\pm2$, $1791.82\pm2$, $1800.02\pm2$, $1821.62\pm2$, $1841.19\pm2$, $1860.98\pm2$, $1865.22\pm2$, $1876.11\pm2$, $1883.01\pm2$, $1900.43\pm2$, $1906.28\pm2$, $1936.24\pm2$, $1958.71\pm2$, $1966.43\pm2$, $1980.85\pm2$, $1994.59\pm2$, $1996.79\pm2$, $2005.98\pm2$, $2084.90\pm2$, $2090.75\pm2$, $2102.82\pm2$, $2134.56\pm2$, $2137.45\pm2$, $2159.33\pm2$, $2169.86\pm2$, $2196.64\pm2$, $2240.20\pm2$, $2257.07\pm2$, $2261.04\pm2$, $2292.01\pm2$, $2302.72\pm2$, $2330.24\pm2$, $2339.45\pm2$, 2340.89±2, 2345.00±2, 2385.34±2, 2432.63±2, 2452.57±2, 2475.26±2, 2497.02±2, 2506.70±2, 2515.58±2, 2532.19±2, 2540.74±2, 2543.60±2, 2545.55±2, 2553.90±2, 2594.54±2, 2621.08±2, 2629.71±2, 2635.51±2, 2659.81±2, 2674.65±2, 2698.27±2 or 3319.44±2.

In a preferred embodiment, the amino acid sequence of this Alzheimer's-associated signal peptide is any of the amino acid sequence represented by SEQ ID NOS: 1 to 4, 16 to 39, 72 to 82, 85 to 86, 99 to 104, 110 to 135, 140 to 161, 167 to 172, 175 to 203, 207 to 220, 222 to 232, 236 to 241, 244 to 255, 260 to 267, 272 to 302, 307 to 327, 336 to 396, 416 to 457, 466 to 479, 486 to 550, 558 to 582, 587 to 592, 597 to 606, and 614 to 623.

This Alzheimer's-associated signal peptide is a signal peptide the abundance of which in bodily fluids from Alzheimer's patients has been confirmed by the inventors to be greater than its reference level. Consequently, if the abundance of this Alzheimer's-associated signal peptide is found to be greater than the reference level in a bodily fluid from a test subject, this abundance is associated with the test subject's suffering from or developing Alzheimer's (typically, it suggests that the test subject suffers from or has developed Alzheimer's).

In another preferred embodiment of the method for aiding Alzheimer's detection disclosed here as the second embodiment, the degree of abundance of any of the Alzheimer's-associated signal peptides having following molecular weights out of the tested Alzheimer's-associated signal peptides in a bodily fluid from a test subject is confirmed to be lower than a reference level set based on the degree of abundance of the same signal peptide in a bodily fluid from a healthy subject:
1620.77±2, 1692.39±2, 1694.78±2, 1801.91±2, 1867.67±2, 1868.76±2, 1875.59±2, 1933.29±2, 1966.96±2, 1996.12±2, 2121.37±2, 2133.94±2, 2135.18±2, 2187.30±2, 2196.08±2, 2269.26±2, 2331.10±2, 2539.62±2, 2620.55±2, 2631.23±2, 2673.96±2 or 3353.34±2.

In a preferred embodiment, the amino acid sequence of this Alzheimer's-associated signal peptide is any of the amino acid sequences represented by SEQ ID NOS: 5 to 11, 40, 41, 46, 47, 54 to 65, 83, 84, 106, 107, 162 to 166, 174, 204, 233, 234, 242, 243, 271, 306, 397 to 404, 458 to 465, 484, 485, 551 to 553, 595, 596, 607 to 609 and 624.

This Alzheimer's-associated signal peptide is a signal peptide the abundance of which in bodily fluids from Alzheimer's patients has been confirmed by the inventors to be lower than its reference level. Consequently, if the abundance of this Alzheimer's-associated signal peptide is found to be lower than the reference level in a bodily fluid from a test subject, this abundance is associated with the test subject's suffering from or developing Alzheimer's (typically, it suggests that the test subject suffers from or has developed Alzheimer's).

Moreover, in a preferred embodiment of the method for aiding Alzheimer's detection disclosed here as the second embodiment, at least the degree of abundance of an Alzheimer's-associated signal peptide with a molecular weight of 1629.17±2, 1767.38±2, 1900.43±2, 1933.29±2, 1966.96±2, 1996.12±2, 2187.30±2, 2196.08±2, 2196.64±2 or 2240.20±2 is tested.

In an especially preferred embodiment, the amino acid sequence constituting this Alzheimer's-associated signal peptide is any of the amino acid sequences represented by SEQ ID NOS: 1 to 75.

This Alzheimer's-associated signal peptide is a signal peptide the presence or absence or degree of abundance of which in bodily fluids from Alzheimer's patients has been confirmed by the inventors to be dramatically different from the presence or absence or degree of abundance of the same signal peptide in a bodily fluid from healthy subjects (typically, from the reference level). Consequently, useful and highly reliable data for judging whether a test subject suffers from or has developed Alzheimer's can be obtained by testing whether or not such an Alzheimer's-associated signal peptide is present in a bodily fluid from the test subject, or by testing the degree of abundance of that Alzheimer's-associated signal peptide when present.

In another preferred embodiment of the method for aiding Alzheimer's detection disclosed here as the second embodiment, the bodily fluid from the test subject is tested for at least 10 kinds of Alzheimer's-associated signal peptides with molecular weights differing by at least 3 from each other.

By testing multiple Alzheimer's-associated signal peptides with differing molecular weights, it is possible to obtain even more reliable (accurate) data for judging whether or not a test subject suffers from or has developed Alzheimer's.

Moreover, in a preferred embodiment of the method for aiding Alzheimer's detection disclosed here as the second embodiment, the presence or absence or degree of abundance of an Alzheimer's-associated signal peptide or peptides in a bodily fluid from the test subject is tested using a mass spectrometer.

The presence or absence and degree of abundance of multiple Alzheimer's-associated signal peptides can be tested efficiently using this mass spectrometer.

Another preferred embodiment of the method for aiding Alzheimer's detection disclosed here as the second embodiment comprises immobilizing the bodily fluid on a thermoplastic resin before testing for the presence or absence and degree of abundance of the Alzheimer's-associated signal peptide in the bodily fluid, and using a matrix assisted laser desorption/ionization-time-of-flight mass spectrometer (MALDI-TOFMS) to test for the presence or absence and degree of abundance of the Alzheimer's-associated signal peptide in the bodily fluid fixed on the thermoplastic resin.

The presence or absence and degree of abundance of even a difficult-to-ionize signal peptide can be analyzed with a high degree of accuracy by fixing the bodily fluid on the thermoplastic resin and using MALDI-TOFMS to investigate the Alzheimer's-associated signal peptide in the immobilize bodily fluid.

Moreover, in another preferred embodiment of the method for aiding Alzheimer's detection disclosed here as the first or second embodiment, the bodily fluid is cerebrospinal fluid.

Cerebrospinal fluid has few contaminants. Because cerebrospinal fluid circulates continuously through the brain and spinal column, moreover, it readily reflects changes in the environment of the nervous system (typically the central nervous system). Consequently, cerebrospinal fluid is a suitable subject for testing signal peptide profiles, and also for testing the presence or absence or degree of abundance of Alzheimer's-associated signal peptides.

Another aspect of the present invention provides a composition for use in detecting Alzheimer's (sometimes called an "Alzheimer's testing composition" below). An Alzheimer's testing composition of one embodiment disclosed herein comprises a synthetic peptide comprising any of the amino acid sequences represented by SEQ ID NOS: 1 to 624, together with one or two or more kinds of carriers.

Another aspect of the present invention provides a kit for use in detecting Alzheimer's (hereunder sometimes called an "Alzheimer's testing kit"). An Alzheimer's testing kit of one embodiment disclosed herein comprises: a synthetic peptide comprising any of the amino acid sequences represented by SEQ ID NOS: 1 to 624; and a support for immobilizing (carrying) the synthetic peptide or a bodily fluid from a test subject.

The synthetic peptide contained in the Alzheimer's testing composition and Alzheimer's testing kit is an artificially synthesized peptide comprising the same amino acid sequence as a signal peptide that is one of the Alzheimer's-associated signal peptides discovered by the inventors. Consequently, this synthetic peptide can be used as a standard substance or a control (typically a positive control) in a method for aiding Alzheimer's detection. Thus, a method for aiding Alzheimer's detection can be implemented with a high degree of reliability using the composition or kit disclosed here.

In a preferred embodiment of the Alzheimer's testing kit disclosed here, the support is made of a thermoplastic resin.

Fixing the synthetic peptide on a thermoplastic resin support allows even difficult-to-ionize peptides to be analyzed (measured) favorably by mass spectrometry (typically MALDI-TOFMS) using MALDI (matrix assisted laser desorption/ionization) as the ionization method. Consequently, this Alzheimer's testing kit is especially desirable when mass spectrometry (typically MALDI-TOFMS) using MALDI (matrix assisted laser desorption/ionization) as the ionization method is used in the method for aiding Alzheimer's detection.

BRIEF DESCRIPTION OF DRAWINGS

FIG. 1 is a graph showing a typical example of a signal peptide profile. This graph schematically shows a profile of signal peptides presumed to be present in a bodily fluid derived from a virtual subject A. The molecular weights of the signal peptides are shown on the horizontal axis, and the amount (mol) of each signal peptide on the vertical axis.

FIG. 2 is a graph displaying the signal peptide profile of subject A from FIG. 1 together with the signal peptide profile of a subject B, which was determined separately from the signal peptide profile of the subject A. The molecular weights of the signal peptides are shown on the horizontal axis, and the abundance (mol) of each signal peptide on the vertical axis. As in the case of the subject A, the signal peptide profile of the subject B displayed on this graph is a profile of signal peptides presumed to be present in a bodily fluid derived from a virtual subject B.

DESCRIPTION OF EMBODIMENTS

Figure 3:
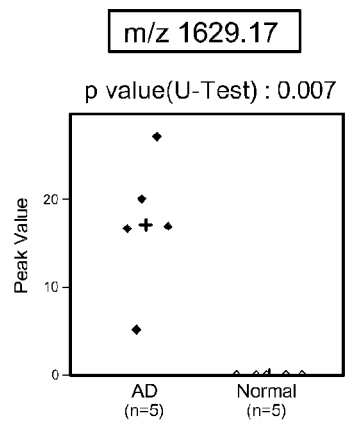
FIG. 3 shows a scatter plot of the results of a test of the abundance (peak values) in cerebrospinal fluids of a signal peptide corresponding to a peak detected at m/z 1629.17 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.

Preferred embodiments of the present invention are explained below. Matters other than those specifically mentioned in this Description (such as the molecular weights and amino acid sequences of the Alzheimer's-associated signal peptides disclosed here) that are necessary for implementing the present invention (such as methods for analyzing signal peptides in bodily fluid, peptide chemical synthesis methods, and general matters associated with the preparation of testing compositions containing peptides) can be understood as design matters by those skilled in the art based on prior art in the fields of cell engineering, physiology, medicine, pharmacology, organic chemistry, biochemistry, genetic engineering, protein engineering, molecular biology, genetics and the like. The present invention can be implemented based on the content disclosed in this Description and technical common knowledge in these fields. In the explanations below, in some cases amino acids are represented by 1-letter abbreviations based on the rules of nomenclature for amino acids given in the IUPAC-IUB guidelines (but are represented by 3-letter abbreviations in the sequence tables).

The entire contents of all literature cited in this Description are also incorporated by reference in this Description.

In this Description, a "synthetic peptide" is not a peptide of which peptide chain exists stably and independently by itself in nature, but rather a peptide fragment that has been manufactured by artificial chemical synthesis or biosynthesis (that is, production based on genetic engineering), and can exist stably in a specific composition (such as an Alzheimer's testing composition or Alzheimer's testing kit used to detect Alzheimer's).

In this Description, moreover, the term "peptide" refers to an amino acid polymer having multiple peptide bonds, and encompasses those called polypeptides and oligopeptides according to the number of constituent amino acid residues. Typically, it refers to those with relatively low molecular weights comprising not more than 50 (preferably not more than 30, such as not more than 20) total amino acid residues.

In this Description, "amino acid residue" is a term encompassing the N-terminal amino acid and C-terminal amino acid of the peptide chain, except where otherwise specified.

The amino acid sequences described in this Description are always N-terminal on the left side and C-terminal on the right.

The terms "healthy" and "normal" are used synonymously in this Description. These terms signify the healthy state of an individual who exhibits no clinical symptoms of Alzheimer's and has not been diagnosed with Alzheimer's. That is, in the present Description a "healthy subject", "healthy person" or "normal subject" means the same as a "healthy individual" or "normal individual", meaning that the individual exhibits no clinical symptoms of Alzheimer's and has not been diagnosed with Alzheimer's. In the present Description, a "healthy subject" is a "healthy person", meaning a test subject used as a comparative subject in the inventions disclosed here.

The "healthy subject" is preferably one who does not suffer from and has not developed any other form of dementia (such as cerebrovascular dementia, Lewy body dementia or Pick's disease), and more preferably is one who also does not suffer from and has not developed any other neurodegenerative disease (such as amyotrophic lateral sclerosis disease or Parkinson's disease).

Moreover, the "healthy subject" is preferably one who resembles the test subject in terms of such background factors as race, age, sex and the like.

In this Description, the "degree of abundance of a signal peptide" is not limited to the absolute quantitative value of the signal peptide in a bodily fluid, but also includes the relative quantitative value of the signal peptide. For example, it may means that the abundance of the signal peptide is greater or less than the abundance thereof in a specific bodily fluid (typically, a bodily fluid from a healthy subject), or that it is greater or less than a specific reference value (typically, a reference value determined based on the degree of abundance of the signal peptide in bodily fluids from healthy subjects).

In this Description, moreover, the "±2" in "M±2" designating a specific molecular weight M indicates an error range that may occur due to the analytic equipment, analytic methods and measurement conditions and differences in these. An error range of "±2" has been set based on the error range that may occur in mass spectrometry using general-purpose MALDI-TOFMS, but the error range is not limited to this, and another value (such as ±1 or ±3) can also be set appropriately depending on the analytic equipment, analytic methods and measurement conditions.

First Embodiment

Focusing on signal peptides in bodily fluid, the inventors first conducted exhaustive research into bodily fluids from Alzheimer's patients and bodily fluids from healthy subjects, including a comprehensive analysis of signal peptides present in these bodily fluids. Considering the fact that the signal peptide profiles of bodily fluids from Alzheimer's patients differ from the signal peptide profiles of bodily fluids from healthy subjects, we perfected a method for aiding Alzheimer's detection based on differences between these signal peptide profiles.

That is, in the method for aiding Alzheimer's detection disclosed here as the first embodiment, a difference between a profile of signal peptides contained in a bodily fluid from a test subject and a profile of signal peptides contained in a bodily fluid from a healthy subject at a specific molecular weight or weights is associated with the test subject's suffering from or developing Alzheimer's (typically, the difference suggests that the test subject suffers from or has developed Alzheimer's, by for example indicating an increased likelihood that the test subject suffers from or has developed Alzheimer's).

Specifically, the method for aiding Alzheimer's detection disclosed as the first embodiment comprises (i) Determining a profile of signal peptides in the molecular weight range of 1000 to 3500 from signal peptides contained in a bodily fluid from a test subject, and (ii) Comparing the signal peptide profile thus determined for the test subject with a signal peptide profile previously determined in bodily fluid from a healthy subject.

In this method for aiding Alzheimer's detection, a difference between the signal peptide profile of the test subject and the signal peptide profile of the healthy subject at any of the following molecular weights is associated with the test subject's suffering from or developing Alzheimer's (typically, the suggests that the test subject suffers from or has developed Alzheimer's):

1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1620.77±2, 1622.09±2, 1629.17±2, 1632.48±2, 1642.66±2, 1675.65±2, 1687.50±2, 1690.86±2, 1692.39±2, 1694.78±2, 1717.35±2, 1724.64±2, 1731.08±2, 1736.78±2, 1767.38±2, 1779.67±2, 1784.07±2, 1786.71±2, 1791.82±2, 1800.02±2, 1801.91±2, 1821.62±2, 1841.19±2, 1860.98±2, 1865.22±2, 1867.67±2, 1868.76±2, 1875.59±2, 1876.11±2, 1883.01±2, 1900.43±2, 1906.28±2, 1933.29±2, 1936.24±2, 1958.71±2, 1966.43±2, 1966.96±2, 1980.85±2, 1994.59±2, 1996.12±2, 1996.79±2, 2005.98±2, 2084.90±2, 2090.75±2, 2102.82±2, 2121.37±2, 2133.94±2, 2134.56±2, 2135.18±2, 2137.45±2, 2159.33±2, 2169.86±2, 2187.30±2, 2196.08±2, 2196.64±2, 2240.20±2, 2257.07±2, 2261.04±2, 2269.26±2, 2292.01±2, 2302.72±2, 2330.24±2, 2331.10±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2539.62±2, 2540.74±2, 2543.60±2, 2545.55±2, 2553.90±2, 2594.54±2, 2620.55±2, 2621.08±2, 2629.71±2, 2631.23±2, 2635.51±2, 2659.81±2, 2673.96±2, 2674.65±2, 2698.27±2, 3319.44±2, 3353.34±2.

In a profile of signal peptides in a bodily fluid from an Alzheimer's patient, a signal peptide specified by any of the following molecular weights is more abundant than in the signal peptide profile of a healthy subject:

1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1622.09±2, 1629.17±2, 1632.48±2, 1642.66±2, 1675.65±2, 1687.50±2, 1690.86±2, 1717.35±2, 1724.64±2, 1731.08±2, 1736.78±2, 1767.38±2, 1779.67±2, 1784.07±2, 1786.71±2, 1791.82±2, 1800.02±2, 1821.62±2, 1841.19±2, 1860.98±2, 1865.22±2, 1876.11±2, 1883.01±2, 1900.43±2, 1906.28±2, 1936.24±2, 1958.71±2, 1966.43±2, 1980.85±2, 1994.59±2, 1996.79±2, 2005.98±2, 2084.90±2, 2090.75±2, 2102.82±2, 2134.56±2, 2137.45±2, 2159.33±2, 2169.86±2, 2196.64±2, 2240.20±2, 2257.07±2, 2261.04±2, 2292.01±2, 2302.72±2, 2330.24±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2540.74±2, 2543.60±2, 2545.55±2, 2553.90±2, 2594.54±2, 2621.08±2, 2629.71±2, 2635.51±2, 2659.81±2, 2674.65±2, 2698.27±2, 3319.44±2.

That is, the fact that a signal peptide specified by any of these molecular weights is more abundant in the signal peptide profile of a test subject than in the signal peptide profile of a healthy subject reflects a strong likelihood that the test subject suffers from or has developed Alzheimer's.

Moreover, in a profile of signal peptides in a bodily fluid from an Alzheimer's patient, a signal peptide specified by any of the following molecular weights is less abundant than in the signal peptide profile of a healthy subject:

1620.77±2, 1692.39±2, 1694.78±2, 1801.91±2, 1867.67±2, 1868.76±2, 1875.59±2, 1933.29±2, 1966.96±2, 1996.12±2, 2121.37±2, 2133.94±2, 2135.18±2, 2187.30±2, 2196.08±2, 2269.26±2, 2331.10±2, 2539.62±2, 2620.55±2, 2631.23±2, 2673.96±2, 3353.34±2.

That is, the fact that a signal peptide specified by any of these molecular weights is less abundant in the signal peptide profile of a test subject than in the signal peptide profile of a healthy subject reflects a strong likelihood that the test subject suffers from or has developed Alzheimer's.

FIG. 1 shows a typical example of a signal peptide profile of a subject A. As shown in FIG. 1, a signal peptide profile can be represented as a bar graph, with the molecular weights of the signal peptides presumed to be present in the bodily fluid of a subject A shown on the horizontal axis, and the amounts of these signal peptides on the vertical axis.

FIG. 2 displays two signal peptide profiles, the signal peptide profile of the subject A from FIG. 1 and the signal peptide profile of a subject B, which was determined separately from the signal peptide profile of the subject A. When the signal peptide profile of the subject A and the signal peptide profile of the subject B are in the relationship shown in FIG. 2, the signal peptide profile of the subject A differs from the signal peptide profile of the subject B at molecular weights of 1000, 1200, 1400, 1600 and 1700. Specifically, the signal peptides specified at the molecular weights 1000 and 1700 are more abundant in the signal peptide profile of the subject A than in the signal peptide profile of the subject B, while the signal peptides specified at the molecular weights 1200, 1400 and 1600 are less abundant in the signal peptide profile of the subject A than in the signal peptide profile of the subject B.

In the method for aiding Alzheimer's detection disclosed here, to obtain data about a test subject's suffering from or developing Alzheimer's (typically, data suggesting that the test subject suffers from or has developed Alzheimer's, such as data showing an increased likelihood that the test subject suffers from or has developed Alzheimer's), it is sufficient to compare the signal peptide profile of the test subject with the signal peptide profile of a healthy subject, and confirm at least one difference at the aforementioned specific molecular weights (typically, an increase or decrease in the abundance of at least one of the signal peptides specified by the specific molecular weights). From the standpoint of obtaining data for determining more reliably (with greater accuracy) whether a test subject suffers from Alzheimer's, it is desirable to confirm that the signal peptide profile of the test subject differs from the signal peptide profile of a healthy subject at multiple (2 or 3 or more, or preferably at least 10, or more preferably at least 20) molecular weights selected from the aforementioned specific molecular weights (typically, that the signal peptides specified by these specific molecular weights are more or less abundant than in a healthy subject).

A profile of signal peptides in a bodily fluid can be determined by a known method (qualitative measurement method) capable of confirming the presence or absence of signal peptides specified by the target molecular weights. Preferably, it is determined by a method (quantitative measurement method) capable of measuring the amounts of the signal peptides specified by the target molecular weights.

In a preferred embodiment, the signal peptide profile is determined by analysis using a mass spectrometer. That is, this signal peptide profile is preferably determined by mass spectrometry. Typically, a signal peptide profile can be determined efficiently by mass spectrometry because multiple signal peptides can be analyzed simultaneously.

A mass spectrum of signal peptides present in a bodily fluid can be obtained by using mass spectrometry to measure a bodily fluid subject to analysis. This mass spectrum is a spectrum obtained as a result of isolating the signal peptides in the bodily fluid according to their mass to charge ratios (m/z), and can be used as the aforementioned signal peptide profile.

The mass spectrometry is not particularly limited, and may be selected appropriately from the conventional mass spectrometry methods of LC-MS (liquid chromatography-mass spectrometry), ESI-MS (electrospray ionization mass spectrometry) and MALDI-TOFMS (matrix assisted laser desorption/ionization-time-of-flight mass spectrometry). In other words, the ionization methods and ion detection methods in mass spectrometry are not particularly limited. For example, the conventional methods of EI (electron ionization), CI (chemical ionization), FAB (fast atom bombardment), ESI (electrospray ionization), APCI (atmospheric pressure chemical ionization), ICP (inductively coupled plasma) and MALDI (matrix assisted laser desorption ionization) can be selected appropriately as the ionization method. For the method of detecting the ionized molecules, a conventional detection method such as magnetic sector, quadrupole (Q), ion trap (IT), Fourier-transform ion cyclotron resonance (FT-ICR), accelerator mass spectrometry (AMS) or time-of-flight (TOF) detection or a tandem method combining these detection methods can be selected appropriately.

In an especially preferred embodiment, analysis is performed by mass spectrometry using MALDI (matrix assisted laser desorption ionization) (or referred to as MNALDIMS below). With MALDI MS, it is typically possible to analyze large molecules that are difficult to ionize (for example, biological molecules such as proteins and peptides). Moreover, MALDI MS is also suited to analyzing signal peptides in bodily fluid because it can typically analyze micro samples and samples with low purity in many cases. In such mass spectrometry using MALDI, the ionized molecules are typically analyzed (detected) by time-of-flight mass spectrometry (TOFMS). That is, MALDI-TOFMS can preferably be adopted for mass spectrometry.

When signal peptides in a bodily fluid are analyzed by such MALDI MS (typically MALDI-TOFMS), the bodily fluid is preferably immobilized on a thermoplastic resin. The signal peptides are often highly hydrophobic molecules having many hydrophobic amino acids, and typically tend to have low ionization efficiency. Ionization of the signal peptides can be promoted by immobilization on a thermoplastic resin. Moreover, immobilizing the bodily fluid on a thermoplastic resin can improve the accuracy of signal peptide analysis because it can suppress ionization of contaminants contained in the bodily fluid.

A conventional known resin material may be used as the thermoplastic resin for immobilizing the bodily fluid, without any particular limitations. For example, a resin material consisting primarily of a polyolefin resin such as polyethylene or polypropylene, an acrylic resin such as polymethyl methacrylate, an ethylene-vinyl acetate copolymer resin (EVA), a polyvinyl chloride resin or a polyester resin or the like can be used. To promote ionization of the signal peptides while suppressing ionization of contaminants, an ethylene-vinyl acetate copolymer resin can be used by preference.

In a preferred embodiment, the bodily fluid to be analyzed is immobilized on a thermoplastic resin that has been molded into a film shape or sheet shape (typically, a thermoplastic film). The thickness of this thermoplastic resin film is not particularly limited, but may be about 50 µm to 200 µm (typically about 100 µm) for example.

The matrix used when analyzing signal peptides in bodily fluid by the MALDI MS (typically MALDI-TOFMS) method is not particularly limited, and a conventional known matrix used in mass spectrometry by MALDI may be selected appropriately. Examples include sinapinic acid (3,5-dimethoxy-4-hydroxycinnamic acid), CHCA (α-cyano-4-hydroxycinnamic acid), ferulic acid (trans-4-hydroxy-3-methoxycinnamic acid), gentisic acid, DHBA (2,5-dihydroxybenzoic acid), HPA (3-hydroxypicolinic acid), dithranol (1,8-dihydroxy-9,10-dihydroanthracen-9-one) and the like. Sinapinic acid is suitable as a matrix for mass spectrometry of high molecular weight molecules, and is also suitable as a matrix for mass spectrometry of peptides and proteins. Consequently, this sinapinic acid can be used favorably as a matrix in mass spectrometry of signal peptides.

In a preferred embodiment, multiple mass spectrometric analyses are repeatedly performed independently of one another on the target bodily fluid. Signal peptides contained in bodily fluid can be accurately assayed by statistically processing the results of such multiple mass spectrometric analyses.

For example, the abundance of a signal peptide present in a bodily fluid can be confirmed by calculating the frequency with which the presence of the target signal peptide is detected in multiple mass spectrometric analyses (detection frequency), and taking this frequency as the quantitative value of the signal peptide. Alternatively, in cases in which the target signal peptide can be quantified by a single mass spectrometric analysis, an average value or median value calculated from the results (quantitative values) of multiple mass spectrometric analyses can be used favorably as the quantitative value of the signal peptide.

Because the quantitative accuracy may be improved by increasing the number of times that mass spectrometry is repeated, mass spectrometry is preferably repeated at least 50 times for example (preferably at least 100 times, or more preferably at least 200 times, or still more preferably at least 300 times).

For example, the abundance of a signal peptide in a bodily fluid can be confirmed by the following methods when MALDI MS is adopted as the method of mass spectrometry.

First, the bodily fluid to be analyzed is exposed multiple times (such as at least 50 times, or preferably at least 100 times, or more preferably at least 200 times, or still more preferably at least 300 times) to an ionizing laser. Mass spectrometry (preferably TOFMS) is performed for each laser exposure, and the presence (detection) or absence of a molecule of the target molecular weight (that is, a signal peptide of the target molecular weight) is confirmed. The frequency with which a molecule of the target molecular weight is detected (detection frequency) in these multiple MALDI MS analyses is then calculated, and this frequency is given as the abundance of the signal peptide to thereby confirm the abundance of the target signal peptide.

In another preferred embodiment, the signal peptide profile may be determined by immunological methods. Typically, immunological methods are methods in which the amount of an antigen is assessed by performing an antigen-antibody reaction between an antigen (or fragment thereof) and an antibody that reacts specifically with that antigen to thereby form an immune complex, and then detecting (visualizing) the antibody. That is, the signal peptide profile can be determined by methods using antibodies that react specifically with the target signal peptides or fragments thereof.

A conventional known method may be adopted as the immunological method without any particular limitations as long as it can detect the target signal peptide. Examples include EIA, radioimmunoassay (RIA), fluorescence immunoassay (FIA), chemiluminescence immunoassay (CLIA), gel precipitation reaction, immunoturbidimetric methods, particle agglutination reaction methods and the like.

Either a method (direct method) using an antibody that has been somehow labeled in advance (labeled primary antibody) or a method (indirect method) using a labeled secondary antibody that specifically recognizes an antibody (primary antibody) to the signal peptide may be used favorably as the immunological method.

A labeling compound commonly used by those skilled in the art in the field of diagnosis by immunological methods such as ELISA may be used as the labeling substance for the antibody (primary antibody or secondary antibody). Examples include radioactive isotopes such as $^3H$, $^{14}C$, $^{131}I$ and $^{99m}Tc$; enzymes such as β-galactosidase, β-glucosidase, alkaline phosphatase, peroxidase and malate dehydrogenase; fluorescent substances such as fluorescamine and fluorescein isothiocyanate; luminescent substances such as luciferin, luminol derivatives, isoluminol derivatives; and the like.

Labeling of the antibody with these labeling substances can be accomplished by conventional known methods, and detailed explanations are omitted because these methods are not a feature of the invention.

The antibody used in the immunological method may be any capable of detecting the target signal peptide, without any particular limitations. For example, it may be a monoclonal antibody, polyclonal antibody, single chain antibody, chimera antibody or the like. The immune animal (antibody-producing animal, host, source) and constant domain of the immunoglobulin (also called the isotype or class) are also not particularly limited. For example, the antibody may be obtained by immunizing a mouse, rat, rabbit, horse, cow, goat, sheep, pig or the like, and may be any of IgG, IgM, IgA, IgE or IgD (preferably IgG).

These antibodies may be prepared by conventional known methods, and detailed explanations are omitted because these methods are not a feature of the present invention.

A composition, kit or protein array (typically a protein microarray) containing an antibody capable of detecting a target signal peptide is also provided by another aspect of the present invention.

The profile of signal peptides contained in the bodily fluid from a healthy subject may be any profile of signal peptides in a bodily fluid collected from at least one healthy subject who does not suffer from and has not developed Alzheimer's. However, the profiles of signal peptides in bodily fluids are subject to differences among individuals (individual differences) even among healthy subjects. Consequently, the profile of signal peptides contained in the bodily fluid from a healthy subject is preferably determined comprehensively from the profiles of signal peptides contained in bodily fluids from multiple (2 or 3 or more, or preferably at least 5, or more preferably at least 10) healthy subjects.

This profile of signal peptides in the bodily fluid from a healthy subject is preferably determined by methods similar to those used to determine the signal peptide profile of the test subject.

In the method for aiding Alzheimers detection disclosed here, the signal peptide profile of the test subject and the signal peptide profile of the healthy subject can be compared by comparing at least one of the aforementioned specific molecular weights at which deviations from the profile of signal peptides in a bodily fluid from a healthy subject indicate the onset or development of Alzheimer's.

Data about the likelihood (typically, an increase or decrease in the likelihood) that a test subject suffers from or has developed Alzheimer's can be obtained more reliably (accurately) by comparing more of the specific molecular weights at which deviations from the signal peptide profile of the healthy subject indicate the onset or development of Alzheimer's when comparing the signal peptide profiles of the test subject and the healthy subject. That is, preferably the signal peptide profile of the test subject and the signal peptide profile of the healthy subject are compared with respect to 2 or 3 or more (preferably at least 10, or more preferably at least 20) of the specific molecular weights at which deviations from the profile of signal peptides in a bodily fluid from a healthy subject indicate the onset or development of Alzheimer's.

In the method for aiding Alzheimer's detection disclosed here, when the signal peptide profile of a test subject and the signal peptide profile of a healthy subject are compared with a focus on specific molecular weights, the likelihood that the test subject suffers from or has developed Alzheimer's (typically, an increase in such likelihood) can be indicated with greater accuracy the greater the frequency of differences at the specific molecular weights being compared.

That is, from the standpoint of obtaining more reliable (accurate) data about the likelihood that a test subject suffers from or has developed Alzheimer's (typically, an increase in such likelihood), it is desirable to confirm that the signal peptide profile of the test subject and the signal peptide profile of the healthy subject differ at 60% or more (preferably at least 70%, or more preferably at least 80%, or still more preferably at least 95%) of the specific molecular weights that are compared in the comparison of the signal peptide profiles of the test subject and the healthy subject.

Second Embodiment

The inventors compared and studied the profiles of signal peptides contained in bodily fluids from Alzheimer's patients and the profiles of signal peptides contained in bodily fluids from healthy subjects in more detail. We then found that the presence and absence and degree of abundance of specific signal peptides (that is, Alzheimer's-associated signal peptides) were different in bodily fluids from Alzheimer's patients and bodily fluids from healthy subjects. We then perfected a method for aiding Alzheimer's detection using such a specific signal peptide (that is, Alzheimer's-associated signal peptide) as an indicator.

That is, in the method for aiding Alzheimer's detection disclosed here as the second embodiment, a difference between the presence or absence or degree of abundance of the Alzheimer's-associated signal peptide in a bodily fluid from a test subject and the presence or absence of the same Alzheimer's-associated signal peptide in a bodily fluid from a healthy subject or a reference level set for degree of abundance thereof is associated with the test subject's suffering from or developing Alzheimer's (typically, the difference suggests that the test subject suffers from or has developed Alzheimer's, by for example indicating an increased likelihood that the test subject suffers from or has developed Alzheimer's).

Specifically, the method for aiding Alzheimer's detection disclosed here as the second embodiment encompasses:

(i) Testing whether one or two or more Alzheimer's-associated signal peptides are present in a bodily fluid from a test subject, or testing the degree of abundance of the Alzheimer's-associated signal peptide or peptides when present.

In this method for aiding Alzheimer's detection, the molecular weight of the Alzheimer's-associated signal peptide is:
1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1620.77±2, 1622.09±2, 1629.17±2, 1632.48±2, 1642.66±2, 1675.65±2, 1687.50±2, 1690.86±2, 1692.39±2, 1694.78±2, 1717.35±2, 1724.64±2, 1731.08±2, 1736.78±2, 1767.38±2, 1779.67±2, 1784.07±2, 1786.71±2, 1791.82±2, 1800.02±2, 1801.91±2, 1821.62±2, 1841.19±2, 1860.98±2, 1865.22±2, 1867.67±2, 1868.76±2, 1875.59±2, 1876.11±2, 1883.01±2, 1900.43±2, 1906.28±2, 1933.29±2, 1936.24±2, 1958.71±2, 1966.43±2, 1966.96±2, 1980.85±2, 1994.59±2, 1996.12±2, 1996.79±2, 2005.98±2, 2084.90±2, 2090.75±2, 2102.82±2, 2121.37±2, 2133.94±2, 2134.56±2, 2135.18±2, 2137.45±2, 2159.33±2, 2169.86±2, 2187.30±2, 2196.08±2, 2196.64±2, 2240.20±2, 2257.07±2, 2261.04±2, 2269.26±2, 2292.01±2, 2302.72±2, 2330.24±2, 2331.10±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2539.62±2, 2540.74±2, 2543.60±2, 2545.55±2, 2553.90±2, 2594.54±2, 2620.55±2, 2621.08±2, 2629.71±2, 2631.23±2, 2635.51±2, 2659.81±2, 2673.96±2, 2674.65±2, 2698.27±2, 3319.44±2 or 3353.34±2.

The signal peptides specified by these molecular weights are signal peptides the presence or absence or degree of abundance of which in bodily fluids from Alzheimer's patients has been confirmed by the inventors to differ from the presence or absence or reference levels set based on and degree of abundance of the same signal peptides in bodily fluids from healthy subjects.

A typical example of the Alzheimer's-associated signal peptide disclosed here is a signal peptide comprising any of the amino acid sequences represented by SEQ ID NOS: 1 to 624.

In the method for aiding Alzheimer's detection disclosed here as the second embodiment, the presence or absence and degree of abundance of the Alzheimer's-associated signal peptide can be tested by methods similar to those used to determine the profile of signal peptides in a bodily fluid in the first embodiment. Consequently, detailed explanations of these testing methods are omitted.

The reference level can be set based on test results obtained by testing the presence or absence, or the degree of abundance when present, of a target signal peptide in a bodily fluid collected from at least one healthy subject who does not suffer from (has not developed) Alzheimer's. However, the presence or absence (or abundance) of target signal peptides in bodily fluids is subject to differences among individuals (individual differences) even among healthy subjects. Consequently, the reference level is preferably determined comprehensively based on the results of testing of bodily fluids from multiple (2 or 3 or more, or preferably at least 5, or more preferably at least 10) healthy subjects.

The methods for testing the bodily fluids collected from the healthy subjects are preferably similar to those used to test the presence or absence or degree of abundance of the Alzheimer's-associated signal peptides in bodily fluids from test subjects.

When one healthy subject is tested as a control, the reference level can be determined using the test result from the single healthy subject as the reference level.

When multiple healthy subjects are tested as control subjects, on the other hand, the reference level can be determined by appropriate statistical processing of the test results from the multiple healthy subjects. The methods of this statistical processing are not particularly limited. For example, the average (or median) of the test results from multiple healthy subjects can be calculated, and this average (or median) value can be set as the upper or lower limit of the reference level. Alternatively, the value of a predetermined multiple of the average (or median) value can be set as the upper or lower limit of the reference level. For example, a multiple of 1.5 times, 2 times, 3 times or 5 times the average (or median value) or a multiple of 0.8 times, or 0.5 times, or 0.3 times the average (or median) value can be the upper or lower limit of the reference level.

Alternatively, a suitable numerical range that includes the average (or median) value can also be set as the reference level. For example, a statistical tolerance range or a range of predetermined multiples can be set as the reference level, or a range up to a number 1 times, or 1.5 times, or 2 times, or 3 times, or 5 times the standard deviation (or standard error) from the average (or median) value can be set as the reference level. A numerical range of ±10%, or ±20%, or ±30%, or ±40%, or ±50% or ±60% of the average (or median) value can also be set as the reference level for example.

A suitable cutoff (or threshold) value can also be calculated and used as the reference level. This cutoff (or threshold) value can be set at a value at which an Alzheimer's patient can be distinguished from a healthy patient with a predetermined sensitivity and/or specificity (such as at least 50%, or at least 60%, or at least 70%, or at least 80%, or at least 90%, or at least 95%, or at least 98%). This cutoff (or threshold) value can be calculated by conventional known statistical methods, and can be determined at will from a comparison of the abundance distributions of the signal peptide in a healthy subject group and an Alzheimer's patient group.

For example, it can be set using an ROC curve (receiver operating characteristic curve). An ROC curve is a graph showing the Alzheimer's detection sensitivity on the vertical axis and the false positive rate (that is, "1-specificity") on the horizontal axis. To set the cutoff value, an appropriate reference value is set for the abundance of the target signal peptide, and an ROC curve can then be obtained by continuously varying this reference value and plotting the resulting changes in the sensitivity and false-positive rate. A value that can be expected to yield the desired sensitivity and specificity can then be set as the cutoff value based on the resulting ROC curve.

"Sensitivity" in an Alzheimer's patient group means the rate (true positive rate) at which the Alzheimer's patient group is judged as positive when the abundance of a signal peptide is set to a predetermined value (the reference value), while "specificity" in a healthy subject group means the rate (true negative rate) at which the healthy subject group is judged as negative when the abundance of a signal peptide is set to a predetermined value (the reference value).

Alternatively, the 5th percentile value (preferably the 1st percentile value) or the 95th percentile value (preferably 99th percentile value) of the abundance of the signal peptide in the healthy subject group or Alzheimer's patient group can be set as the cutoff value.

In the method for aiding Alzheimer's detection disclosed here, data about a test subject's suffering from or developing Alzheimer's (typically, data suggesting that the test subject suffers from or has developed Alzheimer's, such as data regarding the likelihood that the test subject suffers from or has developed Alzheimer's) can be obtained by testing the presence or absence or degree of abundance of at least one kind of Alzheimer's-associated signal peptide in a bodily fluid from the test subject. From the standpoint of improving the reliability (typically accuracy) of the data obtained by this method, it is desirable to test for 2 or 3 or more, or preferably at least 10, or still more preferably at least 20 Alzheimer's-associated signal peptides. When testing for multiple Alzheimer's-associated signal peptides, moreover, the molecular weights of these Alzheimer's-associated signal peptides preferably differ by at least 3 (more preferably by at least 5) from each other.

In the method for aiding Alzheimer's detection disclosed here, a difference between the test results for at least one kind of Alzheimer's-associated signal peptide (difference in the presence or absence of the Alzheimer's-associated signal peptide in a bodily fluid from a test subject, or in the abundance of the signal peptide in a bodily fluid from a test subject) and the reference level of that Alzheimer's-associated signal peptide is associated with the test subject's suffering from or developing Alzheimer's (typically, suggests that the test subject suffers from or has developed Alzheimer's).

That is, a preferred embodiment of the method for aiding Alzheimer's detection disclosed here also comprises comparing the results of a test of a bodily fluid from the test subject (presence or absence of one or two or more Alzheimer's-associated signal peptides in the bodily fluid from the test subject, or degree of abundance of such Alzheimer's-associated signal peptides when present) with the reference levels of the corresponding Alzheimer's-associated signal peptides.

In the method for aiding Alzheimer's detection disclosed here, the likelihood that the test subject suffers from or has developed Alzheimer's (typically, an increase in this likelihood) is indicated more reliably (accurately) the greater the frequency with which the degree of abundance (or presence or absence) of these Alzheimer's-associated signal peptides in the bodily fluid from the test subject differs from the reference levels when the results of a test of a bodily fluid from the test subject are compared with the reference levels of the corresponding Alzheimer's-associated signal peptides.

That is, from the standpoint of obtaining highly reliable (highly accurate) data about the likelihood that a test subject suffers from or has developed Alzheimer's (typically, an increase in such likelihood), it is desirable to confirm that at least 60% (preferably at least 70%, or more preferably at least 80%, or still more preferably at least 95%) of the tested Alzheimer's-associated signal peptides differ from the reference levels for those signal peptides.

In other words, in the method for aiding Alzheimer's detection disclosed here the likelihood that a test subject does not suffer from or has not developed Alzheimer's (typically, a decrease in the likelihood that the test subject suffers from or has developed Alzheimer's) is indicated more reliably (accurately) the lower the frequency with which the degree of abundance (or presence or absence) of these Alzheimer's-associated signal peptides in the bodily fluid from the test subject differs from the reference levels when the results of a test of a bodily fluid from the test subject are compared with the reference levels of the corresponding Alzheimer's-associated signal peptides.

That is, from the standpoint of obtaining highly reliable (high accurate) data about the likelihood that a test subject does not suffer from and has not developed Alzheimer's (typically, a decrease in the likelihood that the test subject suffers from or has developed Alzheimer's), it is desirable to confirm that at least 60% (preferably at least 70%, or more preferably at least 80%, or still more preferably at least 95%) of the tested Alzheimer's-associated signal peptides are within the reference levels for those signal peptides.

In a preferred embodiment of the method for aiding Alzheimer's detection disclosed here, at least any of the Alzheimer's-associated signal peptides having the molecular weights $1629.17\pm2$, $1767.38\pm2$, $1900.43\pm2$, $1933.29\pm2$, $1966.96\pm2$, $1996.12\pm2$, $2187.30\pm2$, $2196.08\pm2$, $2196.64\pm2$, or $2240.20\pm2$ is tested as an Alzheimer's-associated signal peptide. More preferably, at least any of the Alzheimer's-associated signal peptides having the amino acid sequences represented by SEQ ID NOS: 1 to 75 is tested as an Alzheimer's-associated signal peptide. In other words, preferred Alzheimer's-associated signal peptides for testing by the method for aiding Alzheimer's detection disclosed here include at least any of the Alzheimer's-associated signal peptides having molecular weights of $1629.17\pm2$, $1767.38\pm2$, $1900.43\pm2$, $1933.29\pm2$, $1966.96\pm2$, $1996.12\pm2$, $2187.30\pm2$, $2196.08\pm2$, $2196.64\pm2$ or $2240.20\pm2$ (preferably, at least any of the Alzheimer's-associated signal peptides having the amino acid sequences represented by SEQ ID NOS: 1 to 75).

These Alzheimer's-associated signal peptides are Alzheimer's-associated signal peptides the presence or absence or degree of abundance of which in bodily fluids from Alzheimer's patients has been confirmed by the inventors to differ dramatically from the reference levels. Consequently, the reliability (typically accuracy) of data obtained by the method for aiding Alzheimer's detection disclosed here (that is, data associated with a test subject's suffering from or developing Alzheimer's, typically data suggesting that the test subject suffers from or has developed Alzheimer's, such as data regarding the likelihood that the test subject suffers from or has developed Alzheimer's) can be improved by testing the presence or absence or degree of abundance when present of at least one kind (preferably 2 or 3 or more kinds, or more preferably at least 5 kinds, or still more preferably at least 10 kinds) of these Alzheimer's-associated signal peptides in a bodily fluid from a test subject.

In a preferred embodiment of the method for aiding Alzheimer's detection disclosed here, the abundance of a signal peptide capable of distinguishing Alzheimer's patients from healthy subjects with high sensitivity and/or high specificity is tested. For example, preferably the AUC (area under the curve) of each ROC curve is calculated, and the abundance of a signal peptide with a large AUC is tested (that is, the abundance of that signal peptide is compared with the reference level thereof). The AUC is the area under the ROC curve, and it is known that indicators with greater AUCs are better indicators for detecting diseases with high diagnostic ability (predictive ability).

In a preferred embodiment of the method for aiding Alzheimer's detection disclosed here, specific Alzheimer's-associated signal peptides are tested to confirm that the degree of abundance of those signal peptides in a bodily fluid from the test subject is higher than the reference levels. These specific Alzheimer's-associated signal peptides, the abundance of which in a bodily fluid from a test subject is tested to confirm that it is higher than the reference levels, are also called "Alzheimer's positive signal peptides" below.

The Alzheimer's positive signal peptides are typically the Alzheimer's-associated signal peptides specified by the following molecular weights:
1474.95±2, 1497.91±2, 1516.00±2, 1532.22±2, 1534.67±2, 1536.19±2, 1544.01±2, 1556.44±2, 1559.85±2, 1561.62±2, 1591.89±2, 1592.66±2, 1611.67±2, 1622.09±2, 1629.17±2, 1632.48±2, 1642.66±2, 1675.65±2, 1687.50±2, 1690.86±2, 1717.35±2, 1724.64±2, 1731.08±2, 1736.78±2, 1767.38±2, 1779.67±2, 1784.07±2, 1786.71±2, 1791.82±2, 1800.02±2, 1821.62±2, 1841.19±2, 1860.98±2, 1865.22±2, 1876.11±2, 1883.01±2, 1900.43±2, 1906.28±2, 1936.24±2, 1958.71±2, 1966.43±2, 1980.85±2, 1994.59±2, 1996.79±2, 2005.98±2, 2084.90±2, 2090.75±2, 2102.82±2, 2134.56±2, 2137.45±2, 2159.33±2, 2169.86±2, 2196.64±2, 2240.20±2, 2257.07±2, 2261.04±2, 2292.01±2, 2302.72±2, 2330.24±2, 2339.45±2, 2340.89±2, 2345.00±2, 2385.34±2, 2432.63±2, 2452.57±2, 2475.26±2, 2497.02±2, 2506.70±2, 2515.58±2, 2532.19±2, 2540.74±2, 2543.60±2, 2545.55±2, 2553.90±2, 2594.54±2, 2621.08±2, 2629.71±2, 2635.51±2, 2659.81±2, 2674.65±2, 2698.27±2 or 3319.44±2.

In a preferred embodiment, these Alzheimer's positive signal peptides are any of the amino acid sequences represented by SEQ ID NOS: 1 to 4, 16 to 39, 72 to 82, 85 to 86, 99 to 104, 110 to 135, 140 to 161, 167 to 172, 175 to 203, 207 to 220, 222 to 232, 236 to 241, 244 to 255, 260 to 267, 272 to 302, 307 to 327, 336 to 396, 416 to 457, 466 to 479, 486 to 550, 558 to 582, 587 to 592, 597 to 606 and 614 to 623.

These Alzheimer's positive signal peptides are a subset of the Alzheimer's-associated signal peptides, and are signal peptides the abundance of which in bodily fluids from Alzheimer's patients has been confirmed by the inventors to be higher than the reference levels. That is, the fact that the abundance of any Alzheimer's positive signal peptide in a bodily fluid from a test subject exceeds the reference level reflects a strong likelihood that the test subject suffers from or has developed Alzheimer's.

In another preferred embodiment of the method for aiding Alzheimer's detection disclosed here, specific Alzheimer's-associated signal peptides are tested to confirm that the degree of abundance of those signal peptides in a bodily fluid from a test subject is lower than the reference levels. These specific Alzheimer's-associated signal peptides, the abundance of which in a bodily fluid from a test subject is tested to confirm that it is lower than the reference levels, are also called "Alzheimer's negative signal peptides" below.

These Alzheimer's negative signal peptides are typically the Alzheimer's signal peptides specified by the following molecular weights:
1620.77±2, 1692.39±2, 1694.78±2, 1801.91±2, 1867.67±2, 1868.76±2, 1875.59±2, 1933.29±2, 1966.96±2, 1996.12±2, 2121.37±2, 2133.94±2, 2135.18±2, 2187.30±2, 2196.08±2, 2269.26±2, 2331.10±2, 2539.62±2, 2620.55±2, 2631.23±2, 2673.96±2 or 3353.34±2.

In a preferred embodiment, these Alzheimer's negative signal peptides are any of the amino acid sequences represented by SEQ ID NOS: 5 to 11, 40, 41, 46, 47, 54 to 65, 83, 84, 106, 107, 162 to 166, 174, 204, 233, 234, 242, 243, 271, 306, 397 to 404, 458 to 465, 484, 485, 551 to 553, 595, 596, 607 to 609, 624.

These Alzheimer's negative signal peptides are a subset of the Alzheimer's-associated signal peptides, and are signal peptides the abundance of which in bodily fluids from Alzheimer's patients has been confirmed by the inventors to be lower than the reference levels. That is, the fact that the abundance of any Alzheimer's negative signal peptide in a bodily fluid from a test subject is smaller than the reference level reflects a strong likelihood that the test subject suffers from or has developed Alzheimer's.

To confirm a strong likelihood that the test subject suffers from or has developed Alzheimer's, it is desirable to test the degree of abundance of the Alzheimer's positive signal peptides in a bodily fluid from the test subject (or the presence or absence of the Alzheimer's positive signal peptides in a bodily fluid from the test subject).

To confirm a strong likelihood that the test subject does not suffer from and has not developed Alzheimer's, on the other hand, it is desirable to test the degree of abundance of the Alzheimer's negative signal peptides in a bodily fluid from the test subject (or the presence or absence of the Alzheimer's negative signal peptides in a bodily fluid from the test subject).

In the method for aiding Alzheimer's detection disclosed here as the first or second embodiment, the bodily fluid is not particularly limited as long as it is one that can be used as an object of testing in in vitro testing to aid disease detection (diagnosis), and biological samples collected in advance from test subjects, such as cerebrospinal fluid, blood, plasma, serum, lymph fluid, ascites, saliva, synovial fluid, semen, tears, sweat, urine and the like, may be used as is or after being prepared with suitable diluents and the like. It is more desirable to use cerebrospinal fluid, blood, serum or plasma, and cerebrospinal fluid is especially desirable.

The bodily fluid may also be one that has been pre-treated in advance to isolate the signal peptides from a biological sample obtained from a test subject (to increase the abundance of the signal peptides).

<Biomarker>

A signal peptide the degree of abundance (or presence or absence) of which in bodily fluids from Alzheimer's patients is significantly different from the degree of abundance (or presence or absence) thereof in bodily fluids from healthy subjects, and which can be used to detect (diagnose) Alzheimer's by using the degree of abundance of the signal peptide as an indicator, can be used as a biomarker for diagnosing Alzheimer's (hereunder sometimes called an AD biomarker).

"Significantly different" in this Description may mean that the significance level in a statistically significant difference test is 5%. That is, the difference can be judged to be significant if the p value obtained from statistically significant difference testing is p<0.05. Conventional known testing methods such as a t-test (for example, Student's t-test) or U test (Mann-Whitney's U test) may be applied to statistically significant difference testing, with no particular limitations.

The signal peptides designated as Alzheimer's-associated signal peptides in the second embodiment of the method for aiding Alzheimer's detection (including the Alzheimer's positive signal peptides and Alzheimer's negative signal peptides) are all signal peptides which have been confirmed by the inventors to have p values of P<0.05 according to a U test (Mann-Whitney's U test) in a comparison of abundance in bodily fluids from Alzheimer's patients with abundance in bodily fluids from healthy subjects. Consequently, these Alzheimer's-associated signal peptides can be used favorably as AD biomarkers.

That is, a typical example of the AD biomarker provided by the present invention is a signal peptide comprising any of the amino acid sequences represented by SEQ ID NOS: 1 to 624.

Of these Alzheimer's-associated signal peptides, the signal peptides with molecular weights of 1629.17±2, 1767.38±2, 1900.43±2, 1933.29±2, 1966.96±2, 1996.12±2, 2187.30±2, 2196.08±2, 2196.64±2, or 2240.20±2 (typically, signal peptides comprising amino acid sequences represented by SEQ ID NOS: 1 to 75) are all signal peptides which have been confirm by the inventors to have p values of P<0.01 according to a U test (Mann-Whitney's U test) in a comparison of abundance in bodily fluids from Alzheimer's patients with abundance in bodily fluids from healthy subjects. Consequently, these Alzheimer's-associated signal peptides are especially desirable for use as AD biomarkers.

An Alzheimer's positive signal peptide (typically, a signal peptide comprising any of the amino acid sequences represented by SEQ ID NOS: 1 to 4, 16 to 39, 72 to 82, 85 to 86, 99 to 104, 110 to 135, 140 to 161, 167 to 172, 175 to 203, 207 to 220, 222 to 232, 236 to 241, 244 to 255, 260 to 267, 272 to 302, 307 to 327, 336 to 396, 416 to 457, 466 to 479, 486 to 550, 558 to 582, 587 to 592, 597 to 606 and 614 to 623) can also be used favorably as a biomarker (hereunder also called a positive biomarker) an increase in the abundance of which is associated with the onset or development of Alzheimer's (typically, suggests the onset or development of Alzheimer's, by indicating an increased likelihood of the onset or development of Alzheimer's for example).

Moreover, an Alzheimer's negative signal peptide (typically, a signal peptide comprising any of the amino acid sequences represented by SEQ ID NOS: 5 to 11, 40, 41, 46, 47, 54 to 65, 83, 84, 106, 107, 162 to 166, 174, 204, 233, 234, 242, 243, 271, 306, 397 to 404, 458 to 465, 484, 485, 551 to 553, 595, 596, 607 to 609 and 624) can also be used favorably as a biomarker (hereunder also called a negative biomarker) a decrease in the abundance of which is associated with the onset or development of Alzheimer's (typically, suggests the onset or development of Alzheimer's, by indicating an increased likelihood of the onset or development of Alzheimer's for example).

The present invention also provides an artificially synthesized peptide (hereunder sometimes called a synthetic marker peptide) comprising any of the amino acid sequences constituting the aforementioned biomarkers for diagnosing Alzheimer's.

This synthetic marker peptide can be used favorably as a control (typically a positive control) or a standard substance (typically, as an internal standard substance or external standard substance) in a method for aiding Alzheimer's detection. This synthetic marker peptide can also be used favorably for the purpose of calibrating equipment used in a method for aiding Alzheimer's detection.

That is, a typical example of the synthetic marker peptide provided by the present invention is an artificially synthesized peptide comprising any of the amino acid sequences represented by SEQ ID NOS: 1 to 624.

A synthetic marker peptide comprising any of the amino acid sequences constituting the aforementioned positive biomarkers may also be called a "synthetic positive marker peptide" below. Similarly, a synthetic marker peptide comprising any of the amino acid sequences constituting the aforementioned negative biomarkers may also be called a "synthetic negative marker peptide".

Moreover, the present invention also provides a peptide set comprising a combination of 2 or 3 or more (preferably at least 5, or more preferably at least 10, or still more preferably at least 20) synthetic marker peptides selected from the synthetic marker peptides disclosed here. The combination of synthetic marker peptides can be selected appropriately so as to correspond to the AD biomarkers of interest in the method for aiding Alzheimer's detection.

This peptide set can be suitably used when multiple signal peptides are of interest simultaneously in the method for aiding Alzheimer's detection (or when multiple molecular weights are of interest simultaneously in a signal peptide profile).

The peptide set disclosed here may be a set of peptides selected from the synthetic positive marker peptides, or a set of peptides selected from the synthetic negative marker peptides for example.

The peptide set may also be a set of peptides selected from the synthetic marker peptides corresponding to the Alzheimer's-associated signal peptides (that is, AD biomarkers) having molecular weights of 1629.17±2, 1767.38±2, 1900.43±2, 1933.29±2, 1966.96±2, 1996.12±2, 2187.30±2, 2196.08±2, 2196.64±2 or 2240.20±2 (typically, the synthetic marker peptides comprising amino acid sequences represented by SEQ ID NOS: 1 to 75).

The peptide set may also be a set of peptides selected from the synthetic marker peptides corresponding to the Alzheimer's-associated signal peptides (that is, AD biomarkers) within a specific molecular weight range. That is, it may be a set of peptides selected from the synthetic marker peptides corresponding to the Alzheimer's-associated signal peptides (that is, AD biomarkers) having molecular weights of at least 1000 and less than 2000, or at least 2000 and less than 2500, or at least 2500 and less than 3000, or at least 3000 and less than 3500 for example.

The synthetic marker peptide disclosed here can be easily manufactured in accordance with common chemical synthesis methods. For example, either a conventional known solid-phase synthesis method or liquid-phase synthesis method may be adopted. Solid-phase synthesis using Boc (t-butyloxycarbonyl) or Fmoc (9-fluorenylmethyloxycarbonyl) as the protective group of the amino group is desirable.

For the synthetic marker peptide disclosed here, a peptide chain having the desired amino acid sequence and modified (such as C-terminal amidated) parts can be synthesized by solid-phase synthesis using a commercial peptide synthesizer (available for example from Intavis AG, Protein Technologies or the like).

The synthetic marker peptide can also be synthesized based on genetic engineering techniques. That is, a polynucleotide (typically DNA) having a nucleotide sequence (including ATG initiation codon) coding for the amino acid sequence of a desired synthetic marker peptide is synthesized. A recombinant vector carrying a gene expression construct comprising the synthesized polynucleotide (DNA) together with various regulatory elements for expressing the amino acid sequence in host cells (including promoters, ribosome binding sites, terminators, enhancers, and various cis-elements for controlling the expression level) is then constructed according to the host cells.

This recombinant vector is then introduced into specific host cells (such as yeast, insect or plant cells) by ordinary methods, and the host cells (or a tissue or individual organism containing those cells) are cultured under specific conditions. The target peptide can thus be expressed and produced in cells. The peptide can then be isolated from the host cells (or from medium when it is excreted), and refolded, purified or the like as necessary to obtain the target synthetic marker peptide.

Methods conventionally used in the field can be adopted as the methods for constructing a recombinant vector and introducing the resulting vector into host cells and the like, and detailed explanations are omitted because these methods themselves are not a particular feature of the present invention.

For example, a fusion protein expression system can be used for efficient and large-scale production in host cells. That is, a gene (DNA) coding for the amino acid sequence of a target synthetic marker peptide is chemically synthesized, and the synthesized gene is introduced into a favorable site of a suitable fusion protein expression vector (for example, the pET series provided by Novagen, and GST (glutathione S-transferase) fusion protein expression vectors such as the pGEX series provided by Amersham Biosciences). Host cells (typically E. coli) are then transformed with the resulting vector. The resulting transformant is cultured to obtain the target fusion protein. Next, the protein is extracted and purified. The resulting purified fusion protein is then cleaved with a specific enzyme (protease), and a released target peptide fragment (designed synthetic marker peptide) is collected by a method such as affinity chromatography. This can also be refolded by suitable methods as necessary. The synthetic marker peptide disclosed here can be manufactured using such a conventional known fusion protein expression system (for example, a GST/His system provided by Amersham Biosciences for example).

Alternatively, template DNA (that is, a synthetic gene fragment containing a nucleotide sequence coding for the amino acid sequence of a synthetic marker peptide) for use in a cell-free protein synthesis system can be constructed, and a target polypeptide can be synthesized in vitro with a so-called cell-free protein synthesis system using various compounds necessary for peptide synthesis (ATP, RNA polymerase, amino acids, etc.). The papers of Shimizu et al (Shimizu et al., Nature Biotechnology, 19, 751-755 (2001)) and Madin et al (Madin et al., Proc. Natl. Acad. Sci. USA, 97(2), 559-564 (2000)) for example may be consulted with respect to cell-free protein synthesis systems. Based on the techniques described in these papers, many companies have already commissioned polypeptide products at the time of filing of this application, and cell-free protein synthesis kits (for example, the PROTEIOS® wheat germ cell-free protein synthesis kit available from CellFree Sciences Co., Ltd. in Japan) are commercially available.

A single- or double-stranded polynucleotide comprising a nucleotide sequence coding for the synthetic marker peptide disclosed here and/or a nucleotide sequence complementary to that sequence can be easily manufactured (synthesized) by conventional known methods. That is, a nucleotide sequence corresponding to the amino acid sequence of a synthetic marker peptide can be easily determined and provided by selecting codons corresponding to each amino acid residue constituting a designed amino acid sequence. Once the nucleotide sequence has been determined, a (single-stranded) polynucleotide corresponding to the desired nucleotide sequence can then be easily obtained with a DNA synthesizer or the like. Furthermore, the resulting single-stranded DNA can then be used as a template to obtain a target double-stranded DNA by various enzymatic synthesis techniques (typically PCR). Moreover, a polynucleotide may be in the form of either DNA or RNA (mRNA or the like). DNA may be provided in either double-stranded or single-stranded form. In the case of single-stranded DNA, it may be either a coding strand (sense strand) or a non-coding strand (antisense strand) complementary to the sense strand.

As discussed above, the polynucleotide thus obtained can be used in various host cells and cell-free protein synthesis systems as a material for constructing a recombinant gene (expression cassette) for synthetic marker peptide production.

The synthetic marker peptide disclosed here may also be in the form of a salt. For example, it is possible to use an acid addition salt of the peptide obtained by an addition reaction performed by ordinary methods with a commonly used inorganic or organic acid. Other salts (such as metal salts) are also possible. Thus, the "peptides" described in this Description and in the Claims encompass salts of peptides.

<Alzheimer's Testing Composition>

The Alzheimer's testing composition provided by the present invention contains at least one of the synthetic marker peptides. This composition can be used as a control (typically a positive control) or an indicator substance in a method for aiding Alzheimer's detection for example. In other words, the present invention provides a comparative composition (typically a positive control composition) and a standard substance composition in a method for aiding Alzheimer's detection.

The Alzheimer's testing composition disclosed here may contain 2 or 3 or more of the synthetic marker peptides. That is, the Alzheimer's testing composition may contain the synthetic marker peptide set described above.

Like conventional in vitro diagnostic agents (in vitro testing agents) and peptide preparations, the Alzheimer's testing composition disclosed here may contain various components in addition to the synthetic marker peptide as the principal component. In addition to the synthetic marker peptide, it may normally contain at least one kind of accessory component capable of maintaining the peptide stably (typically, without denaturing or decomposition). This accessory component may differ depending on the use and form (mode of use) of the Alzheimer's testing composition, but examples include various pharmacologically (medically) acceptable carriers. A carrier that is commonly used as a diluent, excipient or the like in conventional in vitro diagnostic agents (in vitro testing agents) is preferred.

For example, saline and various pharmacologically acceptable buffers may be included as solvents, or in other words carriers. Typical examples include water, physiological buffers (such as phosphate-buffered saline (PBS)), and various organic solvents. Other examples include aqueous solutions of alcohols (such as ethanol) at suitable concentrations, glycerol, and non-drying oils such as olive oil, as well as liposomes. Various excipients such as sugars (dextrin, lactose, etc.) may also be included. In addition, preservatives, stabilizers, pH adjusters and other agents as well as various fillers, bulking agents, binders, humectants, surfactants, colorants, perfumes and the like may be added as in conventional diagnostic agents and peptide preparations.

The form of the Alzheimer's testing composition is not particularly limited. Examples of typical forms include liquids, suspensions, emulsions, aerosols, foams, granules, powders, pills, capsules, ointments, aqueous gels and the like. The composition may also be in the form of a freeze-dried composition or granules that are dissolved in saline or a suitable buffer (such as PBS) before use to prepare a liquid.

The processes for preparing agents (compositions) in various forms using the synthetic marker peptide (principal component) and various carriers (accessory components)

may be in accordance with conventional known methods, and detailed explanations are omitted because such preparation methods are not themselves a feature of the present invention. Sources of detailed information about formulations include Comprehensive Medicinal Chemistry, Corwin Hansch Ed., Pergamon Press (1990). The entire contents of this text are incorporated by reference in this Description.

<Alzheimer's Testing Kit>

The present invention provides an Alzheimer's testing kit for use in a method for aiding Alzheimer's detection. This kit comprises at least one of the synthetic marker peptide.

The Alzheimer's testing kit may also comprise 2 or 3 or more of the synthetic marker peptide. That is, the Alzheimer's testing kit may comprise the synthetic marker peptide set described above.

The reagents and instruments included in this kit may be selected appropriately according to the types of testing methods (typically, the methods for analyzing the degree of abundance (or presence or absence) of signal peptides in bodily fluid, or the methods for determining signal peptide profiles in bodily fluid) and the detection and measurement equipment (normally a commercial device is used, and suitable chemicals and instruments (substrates, etc.) are selected according to the user's manual). For example, in addition to the synthetic marker peptide and various carriers (including solvents such as saline) constituting the aforementioned Alzheimer's testing composition, these may include diluents (typically various buffers) for diluting the synthetic marker peptide or bodily fluid to be measured, and a matrix for MALDI MS and the like.

One preferred embodiment of the Alzheimer's testing kit disclosed herein is a kit provided with a plurality of the Alzheimer's testing composition, containing mutually different synthetic marker peptides. For example, this may be a kit provided with an Alzheimer's testing composition containing at least one of the synthetic positive marker peptides and an Alzheimer's testing composition containing at least one of the synthetic negative marker peptides.

Another preferred embodiment of the Alzheimer's testing kit disclosed here may be provided with a substrate for immobilizing (carrying) the synthetic marker peptide or bodily fluid.

For example, this may be a kit containing a synthetic marker peptide that has been immobilized (carried) in advance on a substrate. Alternatively, the kit may be provided with a substrate separately from the synthetic marker peptide, and the synthetic marker peptide may be carried (immobilized) on the substrate at the time of use.

The bodily fluid to be measured (that is, a bodily fluid from a test subject) may be immobilized on a substrate that is the same as or different from the substrate on which the synthetic marker peptide is immobilized, and either may be selected depending on the detection method.

Typically, the substrate may be made of various polymer compounds (such as agarose and cellulose) and synthetic resins (such as polystyrene, polypropylene and polycarbonate), or a ceramic material such as glass. The substrate may be in the shape of a plate, beads, or a membrane, stick or test tube or the like depending on the intended use, without any particular limitations. The method of carrying (immobilizing) the peptide on the substrate may be similar to conventional methods, without any particular limitations. For example, a conventional known physical adsorption method, covalent binding method, ionic binding method, crosslinking method or the like may be adopted.

A kit provided with a substrate having a surface made of thermoplastic resin for immobilizing (carrying) the synthetic marker peptide or bodily fluid (or a substrate made of thermoplastic resin) can be used favorably in a testing method (method for aiding Alzheimer's detection) using MALDI MS. In this case, the substrate is preferably in a film, sheet, plate, membrane, stick or chip form. The peptide may then be carried on the substrate by heating and melting the thermoplastic resin.

Another preferred embodiment of the Alzheimer's testing kit disclosed here is a kit provided with an Alzheimer's testing chip comprising at least one of the synthetic marker peptides immobilized (carried) on a film-shaped or plate-shaped substrate. In this substrate, the surface that carries the synthetic marker peptide is made of a thermoplastic resin.

In other words, the present invention provides an Alzheimer's testing chip comprising at least one of the synthetic marker peptide immobilized (carried) on a film-shaped or plate-shaped substrate, wherein the surface of the substrate that carries the synthetic marker peptide is made of a thermoplastic resin.

In a preferred embodiment of this Alzheimer's testing chip, 2 or 3 or more (preferably at least 5, or more preferably at least 10, or still more preferably at least 20) different synthetic marker peptides are immobilized on the same substrate. Typically, this may comprise the synthetic marker peptides constituting the synthetic marker peptide set described above, immobilized on the same substrate.

In an Alzheimer's testing chip comprising multiple synthetic marker peptides immobilized on the same substrate, the multiple synthetic marker peptides may be immobilized on the same spot on the same substrate, or may be immobilized on different spots independently of one another. For example, the synthetic marker peptides constituting the synthetic marker peptide set described above may all be immobilized together on the same spot.

One preferred example of the Alzheimer's testing kit disclosed here is a kit provided with multiple Alzheimer's testing chips having different synthetic marker peptides immobilized thereon. For example, this may be a kit provided with an Alzheimer's testing chip having at least one of the aforementioned synthetic positive marker peptides immobilized thereon, and an Alzheimer's testing chip having at least one of the aforementioned synthetic negative marker peptides immobilized thereon.

Some examples of the present invention are explained below, but the intent is not to limit the invention to what is shown in the examples.

Example 1

Bodily fluids obtained from a healthy subject group and an Alzheimer's patient group were tested to determine the profiles of signal peptides contained in the bodily fluids. In this example, the signal peptide profiles in the bodily fluids were determined by comprehensive analysis using MALDI TOFMS. The specific procedures are given below.

In this example, cerebrospinal fluid collected from 5 healthy subjects and cerebrospinal fluid collected from 5 Alzheimer's patients (2 Hispanic, 3 Caucasian) was used for the samples. Commercial products were purchased and used as all the cerebrospinal fluid samples. The characteristics (sex, race, disease stage, etc.) of the cerebrospinal fluid donors in each group are shown in Table 1.

The disease stage classification in Table 1 was determined by FAST (Functional Assessment Staging of Alzheimer's Disease), with "EARLY" representing mild dementia (FAST score 4) and PROG representing moderate dementia (FAST score 5) in the table.

TABLE 1

|  | Alzheimer's patient group | Healty subject group |
|---|---|---|
| Number of subjects | 5 | 5 |
| Age (±SD) | 69.2 ± 4.5 | 76 ± 12.5 |
| Sex (%) | | |
| Male | 4 (80%) | 2 (40%) |
| Female | 1 (20%) | 3 (60%) |
| Disease stage classification | | |
| EARLY | 4 (80%) | 0 (0%) |
| PROG | 1 (20%) | 0 (0%) |

Each cerebrospinal fluid sample was mixed with a matrix and immobilized on a substrate.

The cerebrospinal fluid sample and matrix liquid were first mixed at a volume ratio of 1:1. The matrix liquid comprised sinapinic acid (CHCA) as the matrix, contained at a concentration of 5 mg/mL in a 50 vol % acetonitrile aqueous solution containing 0.1 vol % trifluoroacetic acid (0.1% TFA/50% ACN aqueous solution).

The matrix liquid was next mixed with the cerebrospinal fluid sample to obtain a mixed matrix-cerebrospinal fluid sample, 2 μL of which was then dropped onto a substrate, and vacuum dried. A measurement plate commonly used in MALDI MS was covered with an EVA film for use as the substrate. That is, in the substrate for immobilizing the bodily fluid in this example the surface for immobilizing the bodily fluid was made of a thermoplastic resin.

The measurement sample thus prepared was subjected to mass spectrometry.

A Shimadzu Corporation AXIMA® Performance was used as the mass spectrometer (MALDI-TOFMS). For the measurement conditions, the laser source was a N2 encapsulated laser (λ=337.1 nm), the acceleration voltage was +20 kV, the delay withdrawal was optimized at m/z 2200, and the flight mode was set to Liner mode. The measurement equipment was calibrated by the external standard method, using Antiotensin II (m/z 1046.54), ACTH fragment 18-39 (m/z 2465.20) and Insulin (m/z 5730.61) as the calibrants (calibration standards). Each cerebrospinal fluid sample was exposed 200 times to laser light, and a mass spectrum was obtained for each laser exposure.

The mass spectra obtained separately for each laser exposure were integrated and averaged to obtain a representative mass spectrum for each cerebrospinal fluid sample.

The mass spectra obtained separately for each of the 200 laser exposures were also compared, the number of times that each peak was detected in the 200 mass spectra was integrated, and the integrated value was given as the peak value. That is, if a peak at m/z 1000 was detected 100 times in the 200 mass spectra separately obtained from the 200 laser exposures, the peak value of this peak is 100.

The peaks detected in the representative mass spectrum obtained above reflect the presence of signal peptides corresponding to the m/z values of these peaks in the measured cerebrospinal fluid sample. That is, the profile of signal peptides in this cerebrospinal fluid is represented qualitatively by this representative mass spectrum. Consequently, a profile of signal peptides present in a bodily fluid (cerebrospinal fluid) can be obtained as a representative mass spectrum by the method disclosed here.

The peak values obtained above reflect the degree of abundance of signal peptides with molecular weights corresponding to the m/z values of these peaks in the measured cerebrospinal fluid sample. That is, the data set relating to these peak values quantitatively shows a profile of the signal peptides in the cerebrospinal fluid. Consequently, a profile of signal peptides present in a bodily fluid (cerebrospinal fluid) can be determined as a collection of data on peak values by the method disclosed here.

Example 2: Comparison of Alzheimer's Patient Group and Healthy Subject Group

The peak values of each peak obtained in Example 1 above were then subjected to statistically significant difference testing between the Alzheimer's patient group and the healthy subject group. A two-tailed test was performed using a U test (Mann-Whitney's U test) as the statistically significant difference test. In this significant difference test, the significance level was set at 5% (that is the difference was significant when the P value was P<0.05).

Figure 4:
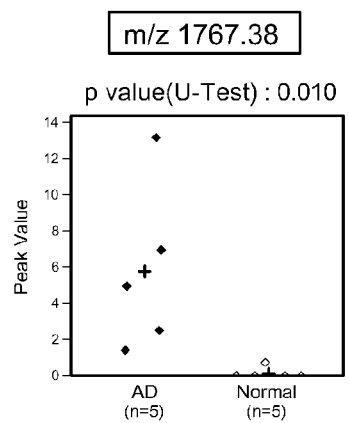
FIG. 4 shows a scatter plot of the results of a test of the abundance (peak values) in cerebrospinal fluids of a signal peptide corresponding to a peak detected at m/z 1767.38 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 5:
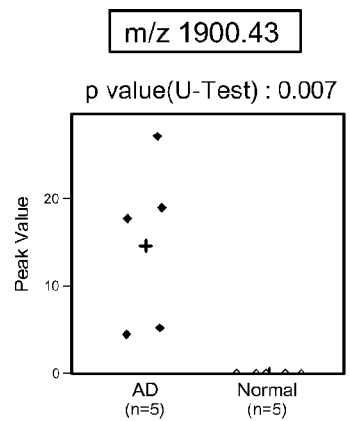
FIG. 5 shows a scatter plot of the results of a test of the abundance (peak values) in cerebrospinal fluids of a signal peptide corresponding to a peak detected at m/z 1900.43 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 6:
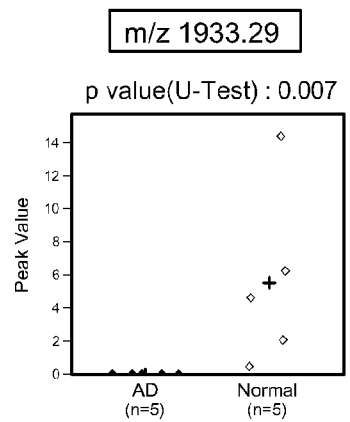
FIG. 6 shows a scatter plot of the results of a test of the abundance (peak values) in cerebrospinal fluids of a signal peptide corresponding to a peak detected at m/z 1933.29 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 7:
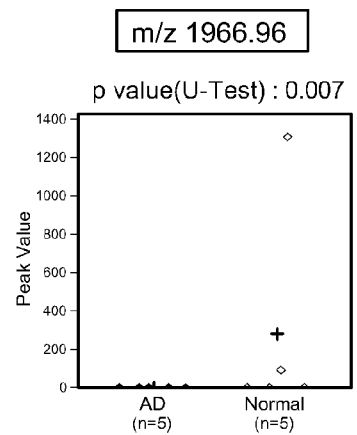
FIG. 7 shows a scatter plot of the results of a test of the abundance (peak values) in cerebrospinal fluids of a signal peptide corresponding to a peak detected at m/z 1966.96 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 8:
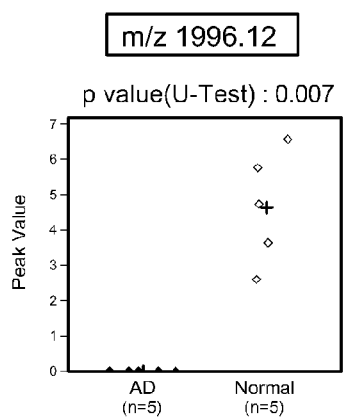
FIG. 8 shows a scatter plot of the results of a test of the abundance (peak values) in cerebrospinal fluids of a signal peptide corresponding to a peak detected at m/z 1996.12 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 9:
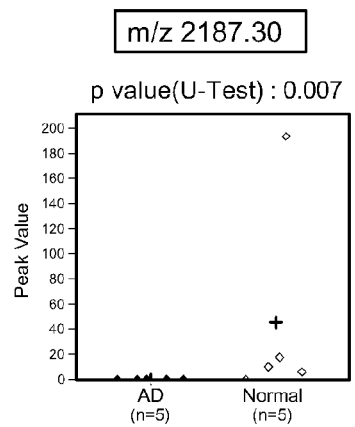
FIG. 9 shows a scatter plot of the results of a test of the abundance (peak values) in cerebrospinal fluids of a signal peptide corresponding to a peak detected at m/z 2187.30 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 10:
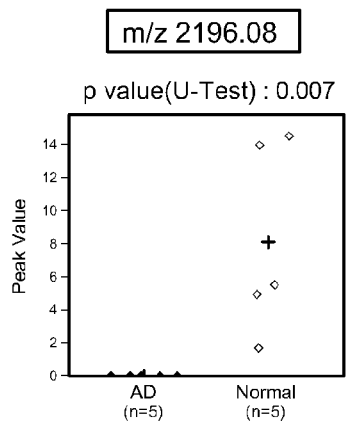
FIG. 10 shows a scatter plot of the results of a test of the abundance (peak values) in cerebrospinal fluids of a signal peptide corresponding to a peak detected at m/z 2196.08 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 11:
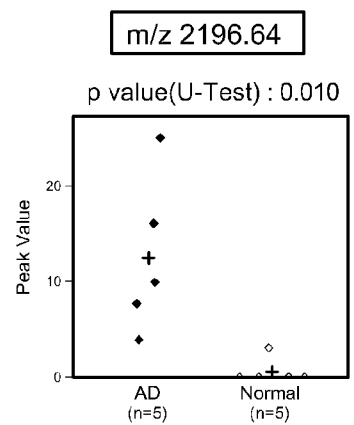
FIG. 11 shows a scatter plot of the results of a test of the abundance (peak values) in cerebrospinal fluids of a signal peptide corresponding to a peak detected at m/z 2196.64 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.
Figure 12:
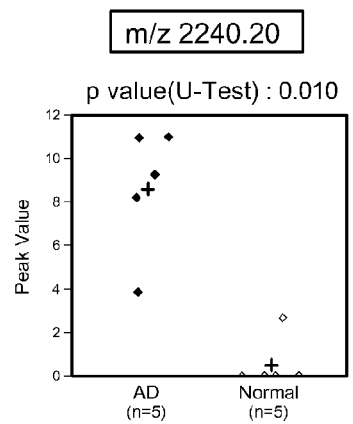
FIG. 12 shows a scatter plot of the results of a test of the abundance (peak values) in cerebrospinal fluids of a signal peptide corresponding to a peak detected at m/z 2240.20 in mass analysis in one example, with the cerebrospinal fluid donors separated into an Alzheimer's patient group and a healthy subject group. "AD" on the horizontal axis represents the Alzheimer's patient group, and "Normal" represents the healthy subject group. The peak values are shown on the vertical axis. The "+" in the figure represents the average of the abundance of the signal peptide (peak values) in each group, and the number given as "p value (U-Test)" indicates the P value calculated by a U test for both groups.

As a result, significant differences between the Alzheimer's patient group and the healthy subject group were found at 109 peaks. The results are shown in Tables 2 to 4. In addition, FIGS. 3 to 12 show scatter plots of the peak values of some of the peaks at which significant differences were found.

TABLE 2

| m/z of each peak | Alzheimer's patient group (n = 5) | | Healty subject group (n = 5) | | P value |
|---|---|---|---|---|---|
| | Average of Peak value | Standard Deviation of Peak value | Average of Peak value | Standard Deviation of Peak value | |
| 1424.73 | 12.37 | 8.64 | 2.92 | 4.29 | 0.034 |
| 1444.52 | 15.43 | 4.15 | 2.84 | 2.06 | 0.012 |
| 1470.78 | 0.00 | 0.00 | 2.50 | 3.75 | 0.025 |
| 1474.95 | 11.72 | 14.87 | 1.10 | 2.47 | 0.031 |
| 1497.91 | 10.54 | 7.58 | 1.13 | 2.53 | 0.045 |
| 1516.00 | 17.34 | 15.64 | 0.00 | 0.00 | 0.025 |
| 1528.84 | 0.79 | 1.76 | 7.25 | 6.57 | 0.031 |
| 1532.22 | 14.75 | 8.83 | 2.70 | 2.26 | 0.022 |
| 1534.67 | 13.30 | 12.18 | 2.39 | 2.29 | 0.037 |
| 1536.19 | 36.68 | 35.32 | 1.54 | 2.60 | 0.020 |
| 1544.01 | 11.35 | 7.21 | 1.98 | 3.26 | 0.036 |
| 1556.44 | 43.56 | 50.08 | 4.31 | 4.55 | 0.022 |
| 1559.85 | 21.21 | 30.08 | 1.57 | 1.59 | 0.012 |
| 1561.62 | 29.33 | 18.87 | 4.01 | 5.91 | 0.036 |
| 1591.89 | 15.50 | 20.98 | 0.01 | 0.02 | 0.045 |
| 1592.66 | 20.64 | 20.27 | 0.89 | 0.82 | 0.036 |
| 1611.67 | 27.87 | 9.90 | 6.74 | 7.75 | 0.021 |
| 1620.77 | 0.33 | 0.74 | 7.68 | 4.54 | 0.045 |
| 1622.09 | 29.59 | 31.75 | 4.53 | 5.69 | 0.036 |
| 1629.17 | 17.07 | 7.98 | 0.00 | 0.00 | 0.007 |
| 1632.48 | 18.79 | 12.32 | 4.24 | 5.35 | 0.021 |
| 1642.66 | 14.48 | 5.53 | 5.70 | 4.18 | 0.037 |
| 1675.65 | 27.84 | 23.83 | 2.70 | 2.01 | 0.022 |
| 1687.50 | 15.59 | 10.85 | 1.81 | 1.96 | 0.012 |
| 1690.86 | 11.11 | 10.02 | 0.69 | 1.55 | 0.045 |
| 1692.39 | 0.26 | 0.59 | 4.74 | 2.97 | 0.018 |
| 1694.78 | 0.00 | 0.00 | 2.58 | 2.45 | 0.025 |
| 1717.35 | 9.59 | 3.96 | 0.82 | 1.15 | 0.011 |
| 1724.64 | 10.75 | 10.37 | 0.84 | 1.89 | 0.018 |
| 1731.08 | 21.86 | 16.67 | 2.03 | 2.44 | 0.022 |
| 1736.78 | 35.83 | 33.19 | 8.51 | 9.99 | 0.037 |
| 1767.38 | 5.74 | 4.64 | 0.13 | 0.30 | 0.010 |
| 1779.67 | 16.09 | 24.28 | 0.00 | 0.00 | 0.025 |
| 1784.07 | 15.24 | 9.81 | 0.89 | 1.68 | 0.020 |
| 1786.71 | 22.11 | 30.85 | 1.45 | 1.87 | 0.036 |
| 1791.82 | 21.80 | 21.92 | 1.20 | 1.87 | 0.021 |
| 1800.02 | 32.83 | 18.82 | 5.83 | 6.66 | 0.037 |
| 1801.91 | 0.89 | 1.65 | 5.31 | 4.48 | 0.036 |
| 1821.62 | 10.26 | 9.64 | 0.63 | 1.41 | 0.045 |
| 1841.19 | 16.88 | 12.58 | 2.74 | 2.68 | 0.036 |
| 1860.98 | 8.09 | 4.22 | 0.97 | 1.43 | 0.011 |
| 1865.22 | 17.28 | 14.31 | 2.54 | 2.46 | 0.037 |

TABLE 2-continued

| m/z of each peak | Alzheimer's patient group (n = 5) | | Healty subject group (n = 5) | | |
|---|---|---|---|---|---|
| | Average of Peak value | Standard Deviation of Peak value | Average of Peak value | Standard Deviation of Peak value | P value |
| 1867.67 | 0.00 | 0.00 | 0.87 | 0.77 | 0.025 |
| 1868.76 | 0.00 | 0.00 | 4.44 | 5.60 | 0.025 |
| 1875.59 | 0.00 | 0.00 | 3.49 | 3.73 | 0.025 |
| 1876.11 | 13.51 | 14.59 | 0.84 | 1.45 | 0.034 |

TABLE 3

| m/z of each peak | Alzheimer's patient group (n = 5) | | Healty subject group (n = 5) | | |
|---|---|---|---|---|---|
| | Average of Peak value | Standard Deviation of Peak value | Average of Peak value | Standard Deviation of Peak value | P value |
| 1883.01 | 34.43 | 14.11 | 13.75 | 10.44 | 0.037 |
| 1900.43 | 14.60 | 9.72 | 0.00 | 0.00 | 0.007 |
| 1906.28 | 26.46 | 19.03 | 0.35 | 0.72 | 0.011 |
| 1933.29 | 0.00 | 0.00 | 5.52 | 5.42 | 0.007 |
| 1936.24 | 7.65 | 7.22 | 0.65 | 1.36 | 0.034 |
| 1958.71 | 25.14 | 15.86 | 3.99 | 7.69 | 0.020 |
| 1966.43 | 14.47 | 18.73 | 0.62 | 1.38 | 0.031 |
| 1966.96 | 0.00 | 0.00 | 279.06 | 573.15 | 0.007 |
| 1980.85 | 11.91 | 9.21 | 1.43 | 1.57 | 0.036 |
| 1994.59 | 20.12 | 6.55 | 3.25 | 5.35 | 0.022 |
| 1996.12 | 0.00 | 0.00 | 4.66 | 1.60 | 0.007 |
| 1996.79 | 22.86 | 19.65 | 3.62 | 7.16 | 0.036 |
| 2005.98 | 9.72 | 8.17 | 1.24 | 2.60 | 0.034 |
| 2084.90 | 7.67 | 7.13 | 0.30 | 0.66 | 0.018 |
| 2090.75 | 12.27 | 14.19 | 0.23 | 0.31 | 0.011 |
| 2102.82 | 8.23 | 10.13 | 0.23 | 0.51 | 0.045 |
| 2121.37 | 0.50 | 0.58 | 7.82 | 7.61 | 0.012 |
| 2133.94 | 0.00 | 0.00 | 4.66 | 7.02 | 0.025 |
| 2134.56 | 9.38 | 4.44 | 0.82 | 1.33 | 0.011 |
| 2135.18 | 0.00 | 0.00 | 2.89 | 1.96 | 0.025 |
| 2137.45 | 7.75 | 5.85 | 0.34 | 0.75 | 0.018 |
| 2159.33 | 7.15 | 4.68 | 0.33 | 0.36 | 0.012 |
| 2169.86 | 12.06 | 15.18 | 0.67 | 1.06 | 0.020 |
| 2187.30 | 0.00 | 0.00 | 45.41 | 82.64 | 0.007 |
| 2196.08 | 0.00 | 0.00 | 8.10 | 5.76 | 0.007 |
| 2196.64 | 12.49 | 8.25 | 0.59 | 1.32 | 0.010 |
| 2240.20 | 8.62 | 2.92 | 0.53 | 1.18 | 0.010 |
| 2257.07 | 9.49 | 5.65 | 1.01 | 1.34 | 0.022 |
| 2261.04 | 12.70 | 15.06 | 1.24 | 2.23 | 0.036 |
| 2269.26 | 0.00 | 0.00 | 3.95 | 4.89 | 0.025 |
| 2292.01 | 14.57 | 11.39 | 3.04 | 5.13 | 0.036 |
| 2302.72 | 5.39 | 5.94 | 0.36 | 0.50 | 0.034 |
| 2330.24 | 3.32 | 2.56 | 0.25 | 0.56 | 0.031 |
| 2331.10 | 0.08 | 0.17 | 8.32 | 10.16 | 0.045 |
| 2339.45 | 8.64 | 3.81 | 3.54 | 2.11 | 0.037 |
| 2340.89 | 5.55 | 2.84 | 1.19 | 1.44 | 0.021 |
| 2345.00 | 11.64 | 15.04 | 1.30 | 1.78 | 0.034 |
| 2385.34 | 5.56 | 3.57 | 0.56 | 1.25 | 0.045 |
| 2432.63 | 2.39 | 3.95 | 0.03 | 0.07 | 0.045 |
| 2452.57 | 7.71 | 4.68 | 1.01 | 2.15 | 0.036 |
| 2475.26 | 7.33 | 6.07 | 0.07 | 0.15 | 0.011 |
| 2497.02 | 13.49 | 12.79 | 0.95 | 0.96 | 0.012 |
| 2506.70 | 8.25 | 8.98 | 0.55 | 0.84 | 0.011 |
| 2515.58 | 9.95 | 15.01 | 0.00 | 0.00 | 0.025 |
| 2532.19 | 2.70 | 4.09 | 0.11 | 0.25 | 0.031 |
| 2539.62 | 0.00 | 0.00 | 5.09 | 7.54 | 0.025 |

TABLE 4

| m/z of each peak | Alzheimer's patient group (n = 5) | | Healty subject group (n = 5) | | |
|---|---|---|---|---|---|
| | Average of Peak value | Standard Deviation of Peak value | Average of Peak value | Standard Deviation of Peak value | P value |
| 2540.74 | 4.45 | 5.21 | 0.00 | 0.00 | 0.025 |
| 2543.60 | 12.02 | 12.68 | 0.03 | 0.07 | 0.045 |
| 2545.55 | 6.74 | 3.53 | 1.28 | 1.14 | 0.012 |
| 2553.90 | 3.97 | 4.96 | 0.03 | 0.06 | 0.045 |
| 2594.54 | 4.68 | 1.35 | 1.14 | 1.17 | 0.012 |
| 2620.55 | 0.00 | 0.00 | 1.70 | 1.53 | 0.025 |
| 2621.08 | 9.08 | 9.53 | 0.64 | 1.43 | 0.018 |
| 2629.71 | 3.25 | 2.74 | 0.22 | 0.33 | 0.020 |
| 2631.23 | 0.00 | 0.00 | 77.76 | 169.60 | 0.025 |
| 2635.51 | 6.20 | 4.35 | 0.05 | 0.12 | 0.018 |
| 2659.81 | 5.96 | 6.77 | 0.00 | 0.00 | 0.025 |
| 2673.96 | 0.03 | 0.07 | 8.03 | 8.17 | 0.045 |
| 2674.65 | 7.26 | 6.31 | 0.21 | 0.48 | 0.018 |
| 2698.27 | 14.08 | 20.66 | 0.45 | 0.93 | 0.034 |
| 3319.44 | 2.04 | 2.61 | 0.03 | 0.07 | 0.045 |
| 3353.34 | 0.09 | 0.20 | 1.65 | 1.76 | 0.045 |
| 3366.98 | 8.66 | 9.74 | 0.00 | 0.00 | 0.025 |

As shown in Tables 2 to 4 and FIGS. 3 to 12, 109 peaks were identified at which there were significant difference in the peak values between the Alzheimer's patient group and the healthy subject group (peaks of m/z 1424.73, 1444.52, 1470.78, 1474.95, 1497.91, 1516.00, 1528.84, 1532.22, 1534.67, 1536.19, 1544.01, 1556.44, 1559.85, 1561.62, 1591.89, 1592.66, 1611.67, 1620.77, 1622.09, 1629.17, 1632.48, 1642.66, 1675.65, 1687.50, 1690.86, 1692.39, 1694.78, 1717.35, 1724.64, 1731.08, 1736.78, 1767.38, 1779.67, 1784.07, 1786.71, 1791.82, 1800.02, 1801.91, 1821.62, 1841.19, 1860.98, 1865.22, 1867.67, 1868.76, 1875.59, 1876.11, 1883.01, 1900.43, 1906.28, 1933.29, 1936.24, 1958.71, 1966.43, 1966.96, 1980.85, 1994.59, 1996.12, 1996.79, 2005.98, 2084.90, 2090.75, 2102.82, 2121.37, 2133.94, 2134.56, 2135.18, 2137.45, 2159.33, 2169.86, 2187.30, 2196.08, 2196.64, 2240.20, 2257.07, 2261.04, 2269.26, 2292.01, 2302.72, 2330.24, 2331.10, 2339.45, 2340.89, 2345.00, 2385.34, 2432.63, 2452.57, 2475.26, 2497.02, 2506.70, 2515.58, 2532.19, 2539.62, 2540.74, 2543.60, 2545.55, 2553.90, 2594.54, 2620.55, 2621.08, 2629.71, 2631.23, 2635.51, 2659.81, 2673.96, 2674.65, 2698.27, 3319.44, 3353.34 and 3366.98). That is, these results show that the signal peptides with molecular weights corresponding to the m/z values of the 109 peaks with peak values that differed significantly between the Alzheimer's patient group and healthy subject group are Alzheimer's-associated signal peptides.

These results also show that the signal peptides with molecular weights corresponding to the m/z values of the 109 peaks with peak values that differed significantly between the Alzheimer's patient group and healthy subject group (that is, the Alzheimer's-associated signal peptides) are signal peptides that can be used to distinguish between Alzheimer's patients and healthy subjects by serving as indicators of the degree of abundance of these signal peptides in bodily fluid (that is, AD biomarkers).

These results also show that the signal peptide profiles of the Alzheimer's patients determined in Example 2 differ from the signal peptides profiles of the healthy subjects at all of the m/z values of the 109 peaks (or the molecular weights corresponding to the m/z values of these peaks). That is, these results confirm that data indicating whether there is a strong likelihood that a test subject suffers from or has developed Alzheimer's can be obtained by determining a profile of signal peptides present in bodily fluid collected from the test subject, and comparing any of the m/z values of these 109 peaks (or the molecular weights corresponding to the m/z values of these peaks) in the signal peptide profile of the test subject and the signal peptide profile of a healthy subject.

These results also confirm that data indicating whether there is a strong likelihood that a test subject suffers from or has developed Alzheimer's can be obtained by testing the degree of abundance of any signal peptide with a molecular weight corresponding to any of these 109 peak m/z values in bodily fluid collected from a test subject, and comparing this with the degree of abundance of the same signal peptide in a bodily fluid from a healthy subject.

Moreover, as shown in Tables 2 to 4 and FIGS. 3 to 12, the peak values of the peaks at the following m/z values (85 peaks) were significantly higher in the Alzheimer's patient group than in the healthy subject group. These results indicate the signal peptides having molecular weights corresponding to the m/z values of these 85 peaks are Alzheimer's positive signal peptides (that is, positive biomarkers): 1424.73, 1444.52, 1474.95, 1497.91, 1516.00, 1532.22, 1534.67, 1536.19, 1544.01, 1556.44, 1559.85, 1561.62, 1591.89, 1592.66, 1611.67, 1622.09, 1629.17, 1632.48, 1642.66, 1675.65, 1687.50, 1690.86, 1717.35, 1724.64, 1731.08, 1736.78, 1767.38, 1779.67, 1784.07, 1786.71, 1791.82, 1800.02, 1821.62, 1841.19, 1860.98, 1865.22, 1876.11, 1883.01, 1900.43, 1906.28, 1936.24, 1958.71, 1966.43, 1980.85, 1994.59, 1996.79, 2005.98, 2084.90, 2090.75, 2102.82, 2134.56, 2137.45, 2159.33, 2169.86, 2196.64, 2240.20, 2257.07, 2261.04, 2292.01, 2302.72, 2330.24, 2339.45, 2340.89, 2345.00, 2385.34, 2432.63, 2452.57, 2475.26, 2497.02, 2506.70, 2515.58, 2532.19, 2540.74, 2543.60, 2545.55, 2553.90, 2594.54, 2621.08, 2629.71, 2635.51, 2659.81, 2674.65, 2698.27, 3319.44, 3366.98.

Furthermore, as shown in Tables 2 to 4 and FIGS. 3 to 12, the peak values of the peaks at the following m/z values (24 peaks) were significantly lower in the Alzheimer's patient group than in the healthy subject group. These results indicate the signal peptides having molecular weights corresponding to the m/z values of these 24 peaks are Alzheimer's negative signal peptides (that is, negative biomarkers): 1470.78, 1528.84, 1620.77, 1692.39, 1694.78, 1801.91, 1867.67, 1868.76, 1875.59, 1933.29, 1966.96, 1996.12, 2121.37, 2133.94, 2135.18, 2187.30, 2196.08, 2269.26, 2331.10, 2539.62, 2620.55, 2631.23, 2673.96, 3353.34.

Moreover, as shown in Tables 2 to 4 and FIGS. 3 to 12, the peak values of the peaks at m/z values of 1629.17, 1767.38, 1900.43, 1933.29, 1966.96, 1996.12, 2196.08, 2196.64 and 2240.20 (10 peaks) were dramatically different (p≤0.01) in the Alzheimer's patient group in comparison with the healthy subject group. These results indicate that the signal peptides having molecular weights corresponding to the m/z values of these 10 peaks are signal peptides that can distinguish Alzheimer's patients from healthy subjects with a high degree of accuracy (reliability) when the degree of abundance of the signal peptides in bodily fluid is used as an indicator.

That is, these results confirm that highly reliable (highly accurate) data indicating a strong possibility that a test subject suffers from or has developed Alzheimer's can be obtained if the signal peptide profile of the test subject differs from the signal peptide profile of a healthy subject at a m/z value at any of these 20 peaks (or a molecular weight corresponding to any of these peak m/z values) in a signal peptide profile determined from bodily fluid collected from the test subject.

In other words, we confirmed that highly reliable (highly accurate) data indicating whether or not there is a strong likelihood that a test subject suffers from or has developed Alzheimer's can be obtained by testing the degree of abundance of any of the signal peptides with molecular weights corresponding to these 10 peak m/z values in a bodily fluid collected from a test subject, and comparing it with the degree of abundance of the same signal peptide in a bodily fluid from a healthy subject.

Example 3: Specifying Signal Peptides

Signal peptides were specified corresponding to each of the 109 peaks identified in Example 2 having peak values that were significantly different between the Alzheimer's patient group and the healthy subject group. That is, the m/z values of each peak were compared with the molecular weights of known signal peptides, and if the molecular weight of a signal peptide was within m/z±2 of a target peak, it was specified as a signal peptide corresponding to the target peak. The results are shown in Tables 5 to 20.

As shown in Tables 5 to 20, the signal peptides comprising the amino acid sequences represented by SEQ ID NOS: 1 to 624 were specified as the Alzheimer's-associated signal peptides (that is, AD biomarkers) disclosed here.

These results indicate that data for aiding Alzheimer's detection (diagnosis) can be obtained (typically, Alzheimer's can be diagnosed) by using as an indicator the degree of abundance of a signal peptide comprising any of the amino acid sequences represented by SEQ ID NOS: 1 to 624.

TABLE 5

| Signal Peptide | | | m/z |
|---|---|---|---|
| Amino acid sequence | SEQ ID No. | MW | of the corresponding peak |
| MLTVALLALLCASASG | 76 | 1533.90 | 1532.22, 1534.67 |
| MKVLILACLVALALA | 77 | 1542.06 | 1544.01 |
| MNPLLILTFVAAALA | 78 | 1557.95 | 1556.44 |
| MNLLLILTFVAAAVA | 79 | 1559.97 | 1559.85, 1561.62 |
| MLLPLLLLLPMCWA | 1 | 1627.18 | 1629.17 |
| MLLILLSVALLALSSA | 2 | 1628.09 | 1629.17 |
| MLLILLSVALLALSSA | 3 | 1628.09 | 1629.17 |

TABLE 5-continued

| Signal Peptide | | | m/z |
|---|---|---|---|
| Amino acid sequence | SEQ ID No. | MW | of the corresponding peak |
| MKVSAVLLCLLLMTAA | 80 | 1677.20 | 1675.65 |
| MALFGALFLALLAGAHA | 81 | 1687.08 | 1687.50 |
| MKWLLLLGLVALSEC | 82 | 1689.15 | 1690.86, 1687.50 |
| MLLSVPLLLGLLGLAVA | 83 | 1693.20 | 1692.39, 1694.78 |
| MGAPRSLLLALAAGLAVA | 84 | 1695.10 | 1694.78 |
| MALRVLLLTALTLCHG | 85 | 1725.18 | 1724.64 |
| MLQNSAVLLVLVISASA | 86 | 1729.11 | 1731.08 |
| MLALLCSCLLLAAGASDA | 87 | 1736.13 | 1736.78 |
| MKRVLVLLLAVAFGHA | 88 | 1738.21 | 1736.78 |
| MISPFLVLAIGTCLTNS | 89 | 1780.17 | 1779.67 |
| MPLLLLLLLLPSPLHP | 90 | 1780.33 | 1779.67 |
| MLPGLALLLLAAWTARA | 91 | 1781.23 | 1779.67 |
| MSLSAFTLFLALIGGTSG | 92 | 1786.12 | 1786.71 |
| MLCLLLTLGVALVCGVPA | 93 | 1786.32 | 1786.71 |
| MFRLWLLLAGLCGLLA | 94 | 1790.30 | 1791.82 |
| MWFLTTLLLWVPVDG | 95 | 1791.18 | 1791.82 |
| MRSTILLFCLLGSTRS | 96 | 1798.19 | 1800.02 |
| MARILLLFLPGLVAVCA | 97 | 1800.34 | 1800.02, 1801.91 |
| MVAAVLLGLSWLCSPLGA | 98 | 1801.24 | 1801.91, 1800.02 |
| MKPLLLAVSLGLIAALQA | 99 | 1822.32 | 1821.62 |
| MLRRALLCLAVAALVRA | 100 | 1840.37 | 1841.19 |
| MALLFLLPLVMQGVSRA | 101 | 1859.36 | 1860.98 |
| MEKILILLLVALSVAYA | 102 | 1860.37 | 1860.98 |
| MTTLLWVFVTLRVITA | 103 | 1864.32 | 1865.22 |
| MGSGLPLVLLLTLLGSSHG | 104 | 1865.26 | 1865.22 |
| MGTQEGWCLLLCLALSGA | 105 | 1866.24 | 1865.22, 1867.67 |
| MKLLTGLVFCSLVLGVSS | 106 | 1867.34 | 1867.67, 1868.76 |
| MAVFLQLLPLLLSRAQG | 107 | 1870.33 | 1868.76 |
| MSALGAVIALLLWGQLFA | 108 | 1874.31 | 1875.59, 1876.11 |
| MKWMVVVLVCLQLLEA | 109 | 1875.42 | 1875.59, 1876.11 |
| MRSLGALLLLLSACLAVSA | 4 | 1902.38 | 1900.43 |
| MGLAWGLGVLFLMHVCGT | 110 | 1905.36 | 1906.28 |
| MWSGWWLWPLVAVCTA | 111 | 1906.29 | 1906.28 |
| MFALGLPFLVLLVASVES | 112 | 1906.35 | 1906.28 |
| MKLASGFLVLWLSLGGGLA | 5 | 1933.38 | 1933.29 |
| MKVLLRLICFIALLISS | 6 | 1933.53 | 1933.29 |
| MKVLWAALLVTFLAGCQA | 113 | 1935.42 | 1936.24 |

TABLE 5-continued

| Signal Peptide | | | m/z |
|---|---|---|---|
| Amino acid sequence | SEQ ID No. | MW | of the corresponding peak |
| MKALIAALLLITLQYSCA | 114 | 1936.44 | 1936.24 |
| MNSGVCLCVLMAVLAAGALT | 115 | 1937.42 | 1936.24 |

TABLE 6

| Signal Peptide | | | m/z |
|---|---|---|---|
| Amino acid sequence | SEQ ID No. | MW | of the corresponding peak |
| MIWYILIIGILLPQSLA | 116 | 1957.49 | 1958.71 |
| MWRSLGLALALCLLPSGGT | 117 | 1959.40 | 1958.71 |
| MPALGWAVAAILMLQTAMA | 118 | 1959.45 | 1958.71 |
| MWLRAFILATLSASAAWG | 7 | 1965.34 | 1966.96, 1966.43 |
| MMREWVLLMSVLLCGLA | 8 | 1965.52 | 1966.96, 1966.43 |
| MRTALLLAALAVATGPALT | 9 | 1967.44 | 1966.96, 1966.43 |
| MQPTLLLSLLGAVGLAAVNS | 10 | 1968.38 | 1966.96, 1966.43 |
| MRTLAILAAILLVALQAQA | 119 | 1980.48 | 1980.85 |
| MRTLAILAAILLVALQAQA | 120 | 1980.48 | 1980.85 |
| MKAVLLALLMAGLALQPGTA | 121 | 1982.51 | 1980.85 |
| MRPLLLLALLGWLLLAEA | 122 | 2006.56 | 2005.98 |
| MTRTRAALLLFTALATSLG | 123 | 2007.42 | 2005.98 |
| MSRGLQLLLLSCAYSLAPA | 124 | 2007.44 | 2005.98 |
| MATPRGLGALLLLLLLPTSG | 125 | 2007.51 | 2005.98 |
| MTSKLAVALLAAFLISAALC | 126 | 2007.52 | 2005.98 |
| MLLLFLLFEGLCCPGENTA | 127 | 2084.53 | 2084.90 |
| MWLCPLALNLILMAASGAVC | 128 | 2090.65 | 2090.75 |
| MGRLQLVVLGLTCCWAVASA | 129 | 2091.58 | 2090.75 |
| MKVSVAALSCLMLVAVLGSQA | 130 | 2091.61 | 2090.75 |
| MRLLPRLLLLLLVFPAT | 131 | 2092.74 | 2090.75 |
| MIFLYQVVHFILFTSVSG | 132 | 2101.53 | 2102.82 |
| MTILGTTFGMVFSLLQVVSG | 133 | 2101.55 | 2102.82 |
| MKFLVFAFILALMVSMIGA | 134 | 2102.73 | 2102.82 |
| MKFFVFALILALMLSMTGA | 135 | 2104.70 | 2102.82 |
| MKFFVFALVLALMISMISA | 136 | 2132.75 | 2133.94, 2134.56 |
| MKFQGPLACLLLALCLGSGEA | 137 | 2135.63 | 2135.18, 2133.94, 2137.45 |
| MARPHPWWLCVLGTLVGLS | 138 | 2136.60 | 2135.18, 2137.45 |
| MSAVLLLALLGFILPLPGVQA | 139 | 2136.71 | 2137.45, 2135.18 |
| MARGAALALLLFGLLGVLVAAP | 140 | 2137.70 | 2137.45 |
| MKILILGIFLFLCSTPAWA | 141 | 2137.71 | 2137.45 |
| MDCQLSILLLLSCSVLDSFG | 142 | 2157.58 | 2159.33 |

TABLE 6-continued

| Signal Peptide Amino acid sequence | SEQ ID No. | MW | m/z of the corresponding peak |
|---|---|---|---|
| MRALLARLLLCVLVVSDSKG | 143 | 2157.70 | 2159.33 |
| MAWTPLFLFLLTCCPGGSNS | 144 | 2158.58 | 2159.33 |
| MRLLLALLGVLLSVPGPPVLS | 145 | 2158.76 | 2159.33 |
| MSGARSKLALFLCGCYVVALG | 146 | 2159.65 | 2159.33 |
| MEPWPLLLLFSLCSAGLVLG | 147 | 2159.67 | 2159.33 |
| MSRLPVLLLLQLLVRPGLQ | 148 | 2159.75 | 2159.33 |
| MDWTWRVFCLLAVAPGAHS | 149 | 2160.54 | 2159.33 |
| MEMLQGLLLLLLSMGGAWA | 150 | 2160.72 | 2159.33 |
| MKSFLLVVNALALTLPFLAV | 151 | 2160.73 | 2159.33 |
| MKLMVLVFTIGLTLLLGVQA | 152 | 2160.79 | 2159.33 |
| MLPCLVVLLAALLSLRLGSDA | 153 | 2168.72 | 2169.86 |
| MARGSAVAWAALGPLLWGCALG | 154 | 2171.61 | 2169.86 |
| MMLHSALGLCLLLVTVSSNLA | 11 | 2186.71 | 2187.30 |
| MRLFLWNAVLTLFVTSLIG | 12 | 2194.71 | 2196.08, 2196.64 |
| MALPVTALLLPLALLLHAARP | 13 | 2194.79 | 2196.08, 2196.64 |

TABLE 7

| Signal Peptide Amino acid sequence | SEQ ID No. | MW | m/z of the corresponding peak |
|---|---|---|---|
| MIFLLLMLSLELQLHQIAA | 14 | 2197.77 | 2196.08, 2196.64 |
| MRGMKLLGALLALAALLQGAVS | 15 | 2197.77 | 2196.08, 2196.64 |
| MVLQTQVFISLLLWISGAYG | 16 | 2239.70 | 2240.20 |
| MVLQTQVFISLLLWISGAYG | 17 | 2239.70 | 2240.20 |
| MVLQTQVFISLLLWISGAYG | 18 | 2239.70 | 2240.20 |
| MMWPMHTPLLLLTALMVAVA | 19 | 2239.88 | 2240.20 |
| MSPFLYLVLLVLGLHATIHC | 20 | 2240.79 | 2240.20 |
| MRPAFALCLLWQALWPGPGGG | 21 | 2241.70 | 2240.20 |
| MNLQPIFWIGLISSVCCVFA | 22 | 2241.75 | 2240.20 |
| MILNKALLLGALALTAVMSPCGG | 155 | 2257.84 | 2257.07 |
| MWRCPLGLLLLLPLAGHLALG | 156 | 2257.87 | 2257.07 |
| MVDGTLLLLLSEALALTQTWA | 157 | 2259.69 | 2261.04 |
| MRPADLLQLVLLLDLPRDLG | 158 | 2261.75 | 2261.04 |
| MKASAALLCLLLTAAAFSPQGLA | 159 | 2261.77 | 2261.04 |
| MRLLILALLGICSLTAYIVEG | 160 | 2262.84 | 2261.04 |
| MKVVPSLLLSVLLAQVWLVPG | 161 | 2262.87 | 2261.04 |
| MRLLWGLIWASSFFTLSLQ | 162 | 2269.73 | 2269.26 |
| MRLLWGLIWASSFFTLSLQ | 163 | 2269.73 | 2269.26 |
| MMGLSLASAVLLASLLSLHLGTA | 164 | 2269.79 | 2269.26 |

TABLE 7-continued

| Signal Peptide | | | m/z |
|---|---|---|---|
| Amino acid sequence | SEQ ID No. | MW | of the corresponding peak |
| MSLLVVSMACVGFFLLQGAWP | 165 | 2269.81 | 2269.26 |
| MSDLLSVFLHLLLLFKLVAP | 166 | 2269.86 | 2269.26 |
| MAELPGPFLCGALLGFLCLSGLA | 167 | 2293.83 | 2292.01 |
| MGLFMIIAILLFQKPTVTEQ | 168 | 2293.85 | 2292.01 |
| MVYKTLFALCILTAGWRVQS | 169 | 2300.81 | 2302.72 |
| MQIELSTCFFLCLLRFCFS | 170 | 2301.82 | 2302.72 |
| MVPPKLHVLFCLCGCLAVVYP | 171 | 2302.94 | 2302.72 |
| MASRLTLLTLLLLLAGDRASS | 172 | 2328.84 | 2330.24 |
| MQRLCVYVLIFALALAAFSEA | 173 | 2329.84 | 2330.24, 2331.10 |
| MKVLISSLLLLLPLMLMSMVS | 174 | 2333.09 | 2331.10 |
| MEPGPALAWLLLLSLLADCLKA | 175 | 2338.89 | 2339.45 |
| MLLAWVQAFLVSNMLLAEAYG | 176 | 2340.82 | 2339.45, 2340.89 |
| MRLSVCLLLLTLALCCYRANA | 177 | 2340.95 | 2339.45, 2340.89 |
| MTSSRLWFSLLLAAAFAGRATA | 178 | 2341.76 | 2340.89 |
| MEAPAQLLFLLLLWLPDTTR | 179 | 2341.84 | 2340.89 |
| MKWKALFTAAILQAQLPITEA | 180 | 2344.84 | 2345.00 |
| MEIKHLLFLVAAACLLPMLSM | 181 | 2345.02 | 2345.00 |
| MEGPRGWLVLCVLAISLASMVT | 182 | 2346.89 | 2345.00 |
| MALGVPISVYLLFNAMTALTEE | 183 | 2383.84 | 2385.34 |
| MKVSAALLWLLLIAAAFSPQGLA | 184 | 2384.95 | 2385.34 |
| MLKPSLPFTSLLFLQLPLLGVG | 185 | 2384.99 | 2385.34 |
| MWVSWAPGLWLLGLWATFGHG | 186 | 2385.81 | 2385.34 |
| MQVSTAALAVLLCTMALCNQFSA | 187 | 2386.88 | 2385.34 |
| MAKVFSFILVTTALTMGREISA | 188 | 2386.89 | 2385.34 |
| MGTRLLPALFLVLLVLGFEVQG | 189 | 2386.96 | 2385.34 |
| MAQHHLWILLLCLQTWPEAAG | 190 | 2431.90 | 2432.63 |
| MSRTAYTVGALLLLLGTLLPAAEG | 191 | 2431.92 | 2432.63 |

TABLE 8

| Signal Peptide | | | m/z of the |
|---|---|---|---|
| Amino acid sequence | SEQ ID No. | MW | corresponding peak |
| MGVPRPQPWALGLLLLFLLPGSLG | 192 | 2433.00 | 2432.63 |
| MPSPGTVCSLLLLGMLWLDLAMA | 193 | 2433.04 | 2432.63 |
| MDMRVLAQLLGLLLLCFPGARC | 194 | 2434.08 | 2432.63 |
| MAQTSSYFMLISCLMFLSQSQG | 195 | 2473.92 | 2475.26 |
| MAQHGAMGAFRALCGLALLCALSLG | 196 | 2476.03 | 2475.26 |
| MAMTWIVFSLWPLTVFMGHIGG | 197 | 2495.06 | 2497.02 |

TABLE 8-continued

| Signal Peptide Amino acid sequence | SEQ ID No. | MW | m/z of the corresponding peak |
|---|---|---|---|
| MGLGARGAWAALLLGTLQVLALLGAA | 198 | 2508.06 | 2506.70 |
| MARLQTALLVVLVLLAVALQATEA | 199 | 2508.10 | 2506.70 |
| MAGPPRLLLLPLLLALARGLPGALA | 200 | 2508.19 | 2506.70 |
| MLTLQTWLVQALFIFLTTESTG | 201 | 2513.97 | 2515.58 |
| MERGAGAKLLPLLLLLRATGFTCA | 202 | 2516.10 | 2515.58 |
| MKSIILFVLSLLLILEKQAAVMG | 203 | 2531.24 | 2532.19 |
| MAVMAPRTLLLLLLGALALTQTRA | 204 | 2538.19 | 2539.62 |
| MKLSGMFLLLSLALFCFLTGVFS | 205 | 2539.19 | 2539.62, 2540.74 |
| MVMRPLWSLLLWEALLPITVTG | 206 | 2540.16 | 2539.62, 2540.74 |
| MAIMAPRTLVLLLSGALALTQTWA | 207 | 2542.14 | 2540.74, 2543.60 |
| MAVMAPRTLLLLLSGALALTQTWA | 208 | 2542.14 | 2540.74, 2543.60 |
| MAVMAPRTLLLLLSGALALTQTWA | 209 | 2542.14 | 2540.74, 2543.60 |
| MAVMAPRTLLLLLSGALALTQTWA | 210 | 2542.14 | 2540.74, 2543.60 |
| MAVMAPRTLLLLLSGALALTQTWA | 211 | 2542.14 | 2540.74, 2543.60 |
| MAVMAPRTLLLLLSGALALTQTWA | 212 | 2542.14 | 2540.74, 2543.60 |
| MKPNIIFVLSLLLILEKQAAVMG | 213 | 2542.22 | 2540.74, 2543.60 |
| MGIQGGSVLFGLLLVLAVFCHSGHS | 214 | 2543.04 | 2543.60 |
| MSAFRLWPGLLIMLGSLCHRGSP | 215 | 2543.10 | 2543.60 |
| MGRGLLRGLWPLHIVLWTRIAS | 216 | 2546.12 | 2545.55 |
| MGLTSQLLPPLFFLLACAGNFVHG | 217 | 2547.07 | 2545.55 |
| MRIHYLLFALLFLFLVPVPGHG | 218 | 2554.18 | 2553.90 |
| MQTPRASPPRPALLLLLLLGGAHG | 219 | 2593.17 | 2594.54 |
| MGSRAELCTLLGGFSFLLLLIPGEG | 220 | 2595.11 | 2594.54 |
| MEKKCTLYFLVLLPFFMILVTA | 221 | 2621.34 | 2621.08, 2620.55 |
| MAPSSPRPALPALLVLLGALFPGPGNA | 222 | 2628.17 | 2629.71 |
| MRQSHQLPLVGLLLFSFIPSQLC | 223 | 2628.19 | 2629.71 |
| MRVMAPRTLILLLSGALALTETWA | 224 | 2628.23 | 2629.71 |
| MRVMAPRTLILLLSGALALTETWA | 225 | 2628.23 | 2629.71 |
| MRVMAPRTLILLLSGALALTETWA | 226 | 2628.23 | 2629.71 |
| MRVMAPRTLILLLSGALALTETWA | 227 | 2628.23 | 2629.71 |
| MRVMAPRTLLLLLSGALALTETWA | 228 | 2628.23 | 2629.71 |
| MRVMAPRTLILLLSGALALTETWA | 229 | 2628.23 | 2629.71 |
| MRVMAPRTLILLLSGALALTETWA | 230 | 2628.23 | 2629.71 |
| MRVMAPRTLILLLSGALALTETWA | 231 | 2628.23 | 2629.71 |
| MRVMAPRTLILLLSGALALTETWA | 232 | 2628.23 | 2629.71 |
| MAAVVAATRWWQLLLVLSAAGMGASG | 233 | 2631.15 | 2631.23 |
| MAGPAIHTAPMLFLVLLLPLELSLA | 234 | 2632.30 | 2631.23 |
| MKDSCITVMAMALLSGFFFFAPASS | 235 | 2673.21 | 2673.96, 2674.65 |

TABLE 8-continued

| Signal Peptide Amino acid sequence | SEQ ID No. | MW | m/z of the corresponding peak |
|---|---|---|---|
| MRVTAPRTLLLLLWGALALTETWA | 236 | 2697.28 | 2698.27 |
| MRVTAPRTLLLLLWGALALTETWA | 237 | 2697.28 | 2698.27 |

TABLE 9

| Signal Peptide Amino acid sequence | SEQ ID No. | MW | m/z of the corresponding peak |
|---|---|---|---|
| MRVTAPRTLLLLLWGALALTETWA | 238 | 2697.28 | 2698.27 |
| MRVTAPRTLLLLLWGALALTETWA | 239 | 2697.28 | 2698.27 |
| MRVTAPRTLLLLLWGALALTETWA | 240 | 2697.28 | 2698.27 |
| MAAASRSASGWALLLLVALWQQRAAG | 241 | 2699.17 | 2698.27 |
| MHSKVTIICIRFLFWFLLLCMLIGKSHT | 242 | 3352.22 | 3353.34 |
| MAFPPRRRLRLGPRGLPLLLSGLLLPLCRA | 243 | 3354.22 | 3353.34 |

TABLE 10

| Signal Peptide Amino acid sequence | SEQ ID No. | MW | m/z of the corresponding peak |
|---|---|---|---|
| MRALAVLSVTLVMA | 244 | 1474.90 | 1474.95 |
| MALLLLSLGLSLIAA | 245 | 1498.94 | 1497.91 |
| MNRVLCAPAAGAVRA | 246 | 1499.83 | 1497.91 |
| MNPLLILAFVGAAVA | 247 | 1499.88 | 1497.91 |
| MKLGLLCALLSLLAG | 248 | 1515.99 | 1516.00 |
| MLGITVLAALLACASS | 249 | 1533.92 | 1532.22, 1534.67 |
| MRTLLTILTVGSLAA | 250 | 1559.94 | 1559.85, 1561.62 |
| MRLLTLLGLLCGSVA | 251 | 1560.00 | 1559.85, 1561.62 |
| MKIIILLGFLGATLS | 252 | 1590.05 | 1591.89 |
| MKVLLLTGLGALFFA | 253 | 1594.04 | 1592.66 |
| MAMGLFRVCLVVVTA | 254 | 1610.09 | 1611.67 |
| MLLPLLLSSLLGGSQA | 255 | 1613.00 | 1611.67 |
| MLLLPLLLPVLGAGSL | 256 | 1620.12 | 1620.77, 1622.09 |
| LTVTLMVLSSRLAFA | 257 | 1622.01 | 1622.09, 1620.77 |
| MAQVLIVGAGMTGSLCA | 258 | 1622.01 | 1622.09, 1620.77 |
| MLLLLLLAPLFLRP | 259 | 1623.17 | 1622.09, 1620.77 |
| MLLILLSVALLALSSA | 23 | 1628.09 | 1629.17 |
| MLLILLSVALLALSSA | 24 | 1628.09 | 1629.17 |
| MTLRLLVAALCAGILA | 25 | 1629.11 | 1629.17 |

TABLE 10-continued

| Signal Peptide Amino acid sequence | SEQ ID No. | MW | m/z of the corresponding peak |
|---|---|---|---|
| MMLRLLSSLLLVAVA | 26 | 1630.14 | 1629.17 |
| MMLRLLSSLLLVAVA | 27 | 1630.14 | 1629.17 |
| MVLLLLVAIPLLVHS | 28 | 1631.14 | 1632.48, 1629.17 |
| MRVLACLLAALVGIQA | 260 | 1642.11 | 1642.66 |

TABLE 11

| Signal Peptide Amino acid sequence | SEQ ID No. | MW | m/z of the corresponding peak |
|---|---|---|---|
| MLLVLLSVVLLALSSA | 261 | 1642.12 | 1642.66 |
| MVAAAAATEARLRRR | 262 | 1642.95 | 1642.66 |
| MKEYVLLLFLALCS | 263 | 1643.09 | 1642.66 |
| MAAGAVFLALSAQLLQA | 264 | 1675.03 | 1675.65 |
| MAAGAVFLALSAQLLQA | 265 | 1675.03 | 1675.65 |
| MWRLALGGVFLAAAQA | 266 | 1675.03 | 1675.65 |
| MLWLLFFLVTAIHA | 267 | 1675.12 | 1675.65 |
| MGSRCALALAVLSALLC | 268 | 1692.15 | 1690.86, 1692.39 |
| MACAAVMIPGLLRCSVG | 269 | 1692.17 | 1690.86, 1692.39 |
| MKRLVCVLLVCSSAVA | 270 | 1692.19 | 1690.86, 1692.39 |
| MGGAGILLLLLAGAGVVVA | 271 | 1695.15 | 1694.78 |
| MLLLGILTLAFAGRTAG | 272 | 1718.14 | 1717.35 |
| MDVLFVAIFAVPLILG | 273 | 1718.18 | 1717.35 |
| MARTRDRVRLLLLL | 274 | 1726.17 | 1724.64 |
| MKRSVAVWLLVGLSLG | 275 | 1729.17 | 1731.08 |
| MTPIVTVLICLRLSLG | 276 | 1729.23 | 1731.08 |
| METFPLLLLSLGLVLA | 277 | 1730.19 | 1731.08 |
| MRGLGLWLLGAMMLPA | 278 | 1730.24 | 1731.08 |
| MGRLLALVVGAALVSSAC | 279 | 1731.16 | 1731.08 |
| MLFSALLLEVIWILA | 280 | 1732.21 | 1731.08 |
| MEPGLWLLFGLTVTSA | 281 | 1735.08 | 1736.78 |
| MSSSSWLLLSLVAVTAA | 282 | 1736.06 | 1736.78 |
| MAPKLITVLCLGFCLN | 283 | 1736.24 | 1736.78 |
| MAVLFLLLFLCGTPQA | 284 | 1737.21 | 1736.78 |
| MAVVPLLLLGGLWSAVGA | 29 | 1767.21 | 1767.38 |
| MLLRLLLAWAAAGPTLG | 30 | 1767.21 | 1767.38 |
| MPLSPGLLLLLLSGATAT | 31 | 1768.19 | 1767.38 |
| MGWLFLKVLLAGVSFS | 32 | 1768.20 | 1767.38 |
| MGAAGLLGVFLALVAPGVL | 33 | 1769.23 | 1767.38 |
| MGLLLLVPLLLLPGSYG | 34 | 1769.27 | 1767.38 |
| MGLSIFLLLCVLGLSQA | 285 | 1778.26 | 1779.67 |
| MRRLLIPLALWLGAVG | 286 | 1779.27 | 1779.67 |
| MLIATSFFLFFSSVVA | 287 | 1780.16 | 1779.67 |
| MRWILFIGALIGSSIC | 288 | 1780.23 | 1779.67 |
| MIPLLLAALLCVPAGALT | 289 | 1780.31 | 1779.67 |
| MVTKAFVLLAIFAEASA | 290 | 1782.18 | 1784.07 |
| MWQLLLPTALLLLVSA | 291 | 1782.27 | 1784.07 |
| MWQLLLPTALLLLVSA | 292 | 1782.27 | 1784.07 |
| MVPVLLSLLHLLGPAIP | 293 | 1783.30 | 1784.07 |
| MGPEALSSLLLLLLVASG | 294 | 1784.19 | 1784.07 |
| MSQVMSSPLLAGGHAVSL | 295 | 1785.12 | 1784.07, 1786.71 |
| MLLPALLFGMAWALADG | 296 | 1790.23 | 1791.82 |
| MVLLCLFLASLAATPRA | 297 | 1790.27 | 1791.82 |
| MWFLTTLLLWVPVDG | 298 | 1791.19 | 1791.82 |

TABLE 12

| Signal Peptide Amino acid sequence | SEQ ID No. | MW | m/z of the corresponding peak |
|---|---|---|---|
| MWFLTTLLLWVPVDG | 299 | 1791.19 | 1791.82 |
| MWLFFGITGLLTAALSG | 300 | 1798.18 | 1800.02 |
| MAVPARTCGASRPGPART | 301 | 1799.11 | 1800.02 |

TABLE 12-continued

| Signal Peptide Amino acid sequence | SEQ ID No. | MW | m/z of the corresponding peak |
|---|---|---|---|
| MWAQLLLGMLALSPAIA | 302 | 1799.28 | 1800.02 |
| MDFGLALLLAGLLGLLLG | 303 | 1800.28 | 1800.02, 1801.91 |
| MRTLLLVLWLATRGSA | 304 | 1801.23 | 1801.91, 1800.02 |
| MVPHLLLLCLLPLVRA | 305 | 1801.38 | 1801.91, 1800.02 |
| MFLLLALLTELGRLQA | 306 | 1802.26 | 1801.91 |
| MITFLPLLLGLSLGCTGA | 307 | 1820.29 | 1821.62 |
| MLAVLYLLVKTAKLGTS | 308 | 1821.30 | 1821.62 |
| MAPPAARLALLSAAALTLA | 309 | 1822.25 | 1821.62 |
| MRPLLGLLLVFAGCTFA | 310 | 1822.31 | 1821.62 |
| MLSLLVWILTLSDTFS | 311 | 1839.23 | 1841.19 |
| MVPPVWTLLLLVGAALF | 312 | 1840.35 | 1841.19 |
| MAPKLLLLLCLFSGLHA | 313 | 1840.37 | 1841.19 |
| MRDLPLTSLALVLSALGA | 314 | 1841.25 | 1841.19 |
| MPMDLILVVWFCVCTA | 315 | 1841.36 | 1841.19 |
| MKGILVAGITAVLVAAVES | 316 | 1842.28 | 1841.19 |
| MARGSALLLASLLLAAALS | 317 | 1842.28 | 1841.19 |
| MNYSLHLAFVCLSLFT | 318 | 1859.25 | 1860.98 |
| MTAPWVALALLWGSLCAG | 319 | 1860.28 | 1860.98 |
| MGVMAMLMLPLLLLGISG | 320 | 1860.49 | 1860.98 |
| MRLLLLVPLLLAPAPGSS | 321 | 1861.37 | 1860.98 |
| MLKMLSFKLLLLAVALG | 322 | 1861.48 | 1860.98 |
| MAPAPVTLLAPGAASSMSCS | 323 | 1862.22 | 1860.98 |
| MTSSLLLAFLLLAPTTVA | 324 | 1862.31 | 1860.98 |
| MGSCARLLLLWGCTVVAA | 325 | 1864.33 | 1865.22 |
| MAAAGAAVARSPGIGAGPALR | 326 | 1865.19 | 1865.22 |
| MKILCIFLTFVFTVSC | 327 | 1865.40 | 1865.22 |
| MRLLVAPLLLAWVAGATA | 328 | 1866.35 | 1865.22, 1867.67 |
| MKPLLLAISLSLIAALQA | 329 | 1866.38 | 1865.22, 1867.67 |
| MLFLQFLLLALLLPGGD | 330 | 1874.36 | 1875.59, 1876.11 |
| MAGSLTGLLLLQAVSWASG | 331 | 1875.22 | 1875.59, 1876.11 |
| LGLCWVFLVALLRGVLC | 332 | 1875.42 | 1875.59, 1876.11 |
| MKLFWLLFTIGFCWA | 333 | 1876.36 | 1875.59, 1876.11 |
| MALRRLGAALLLLPLLAA | 334 | 1876.43 | 1875.59, 1876.11 |
| MIPAVVLLLLLVEQAAA | 335 | 1877.41 | 1875.59, 1876.11 |
| MARARAGALLALWVLGAAA | 336 | 1882.31 | 1883.01 |
| MKALCLLLLPVLGLLVSS | 337 | 1883.48 | 1883.01 |
| MLSLLLLALPVLASPAYV | 338 | 1884.40 | 1883.01 |
| MVRLCQALLLLVATVALA | 35 | 1898.45 | 1900.43 |

TABLE 12-continued

| Signal Peptide | | | m/z of |
|---|---|---|---|
| Amino acid sequence | SEQ ID No. | MW | the corresponding peak |
| MALQLWALTLLGLLGAGAS | 36 | 1899.33 | 1900.43 |
| MAFVLILVLSFYELVSG | 37 | 1901.34 | 1900.43 |
| MRLILFFGALFGHIYC | 38 | 1901.37 | 1900.43 |

TABLE 13

| Signal Peptide | | | m/z of |
|---|---|---|---|
| Amino acid sequence | SEQ ID No. | MW | the corresponding peak |
| MLPWLLVFSALGIQAWG | 39 | 1902.34 | 1900.43 |
| MKASVVLSLLGYLVVPSGA | 339 | 1904.35 | 1906.28 |
| MLLLLLLLPPLLCGRVGA | 340 | 1905.53 | 1906.28 |
| MKTLAGLVLGLVIFDAAVT | 40 | 1932.40 | 1933.29 |
| MGPGVLLLLLVATAWHGQG | 41 | 1933.35 | 1933.29 |
| MARVPPVGALLLLRGSRQ | 42 | 1934.39 | 1933.29, 1936.24 |
| MLLLFSVILISWVSTVGG | 341 | 1935.40 | 1936.24 |
| MWQLWASLCCLLVLANA | 342 | 1935.41 | 1936.24 |
| MLMLFVFGVLLHEVSLS | 343 | 1935.43 | 1936.24 |
| MRSLLLLSAFCLLEAALA | 344 | 1935.43 | 1936.24 |
| MQQRGLAIVALAVCAALHA | 345 | 1936.38 | 1936.24 |
| MGARGALLLALLLARAGLR | 346 | 1936.44 | 1936.24 |
| MPLALTLLLLSGLGAPGGWG | 347 | 1937.38 | 1936.24 |
| MAAAGLVAVAAAAEYSGTVASG | 348 | 1938.19 | 1936.24 |
| MSTMRLLTLALLFSCSVA | 349 | 1957.46 | 1958.71 |
| MSISSALAMVFMGAKGNTAA | 350 | 1958.36 | 1958.71 |
| MKLHCCLFTLVASIIVPA | 351 | 1959.52 | 1958.71 |
| MLTPPLLLLLPLLSALVAA | 352 | 1959.55 | 1958.71 |
| MPARRLLLLLTLLLPGLG | 353 | 1960.55 | 1958.71 |
| MFLLLTALQVLAIAMTQS | 354 | 1964.47 | 1966.43 |
| MGRGVRVLLLLSLLHCAGG | 43 | 1965.46 | 1966.43, 1966.96 |
| MKMLLLLHCLGVFLSCSG | 44 | 1965.55 | 1966.43, 1966.96 |
| MASLLPLLCLCVVAAHLAGA | 45 | 1966.51 | 1966.43, 1966.96 |
| MALLVLGLVSCTFFLAVNG | 46 | 1968.46 | 1966.96 |
| MSLLLLLLVSYYVGTLG | 47 | 1968.47 | 1966.96 |
| MLLLLLPLLWGRERAEG | 355 | 1980.45 | 1980.85 |
| MRTIAILAAILLVALQAQA | 356 | 1980.49 | 1980.85 |
| MSLSFLLLLFFSHLILS | 357 | 1981.47 | 1980.85 |
| MGRVPLAWCLALCGWACM | 358 | 1981.53 | 1980.85 |
| MGLLGILCFLIFLGKTWG | 359 | 1982.53 | 1980.85 |
| MAFLIILITCFVIILATS | 360 | 1982.57 | 1980.85 |

TABLE 13-continued

| Signal Peptide Amino acid sequence | SEQ ID No. | MW | m/z of the corresponding peak |
|---|---|---|---|
| MWLPLVLLLAVLLLAVLC | 361 | 1993.68 | 1994.59 |
| MRAGPGPTVTLALVLAVAWA | 48 | 1994.43 | 1996.12, 1994.59 |
| MAGIPGLLFLLFFLLCAVG | 49 | 1995.57 | 1996.12, 1994.59, 1996.79 |
| MVLSLTGLIAFSFLQATLA | 50 | 1996.44 | 1996.12, 1994.59, 1996.79 |
| MLLWLLLLILTPGREQS | 51 | 1996.49 | 1996.12, 1994.59, 1996.79 |
| MVLLLVILIPVLVSSAGTSA | 52 | 1996.53 | 1996.12, 1996.79, 1994.59 |
| MVCGCSALLPLPNPRPTMP | 53 | 1997.50 | 1996.12, 1996.79 |
| MGGLLLAAFLALVSVPRAQA | 362 | 1998.47 | 1996.79 |
| MVTLAELLVLLAALLATVSG | 363 | 1998.50 | 1996.79 |
| MQLTGKVVLSAAALLLVTVA | 364 | 1998.50 | 1996.79 |
| MMWLLLTTTCLICGTLNA | 365 | 1998.53 | 1996.79 |
| MRPVALLLLPSLLALLAHG | 366 | 1998.55 | 1996.79 |
| MGPAGCAFTLLLLLGSCLHS | 367 | 2004.47 | 2005.98 |

TABLE 14

| Signal Peptide Amino acid sequence | SEQ ID No. | MW | m/z of the corresponding peak |
|---|---|---|---|
| MLPQIPFLLLVSLNLVHG | 368 | 2004.51 | 2005.98 |
| MEVVLIFVYSLLVPVVLA | 369 | 2004.55 | 2005.98 |
| MDLSAAAALCLWLLSACRP | 370 | 2005.46 | 2005.98 |
| MWLLRCVLLCVSLSLAVS | 371 | 2006.57 | 2005.98 |
| MLSSVVFWGLIALIGTSRG | 372 | 2007.43 | 2005.98 |
| MPGAAGVLLLLLSGGLGGVQA | 373 | 2007.47 | 2005.98 |
| MELLQVTILFLLPSICSS | 374 | 2007.49 | 2005.98 |
| MTPACPLLLSVILSLRLATA | 375 | 2083.63 | 2084.90 |
| MLLALALLLAFLPPASQKSS | 376 | 2084.60 | 2084.90 |
| MGRPLLLPLLPLLLPPAFL | 377 | 2084.73 | 2084.90 |
| MAFLPSWVCVLVGSFSASLA | 378 | 2085.52 | 2084.90 |
| MGPHFTLLCAALAGCLLPAEG | 379 | 2085.55 | 2084.90 |
| MGVLGRVLLWLQLCALTQA | 380 | 2085.61 | 2084.90 |
| MAGIFYFALFSCLFGICDA | 381 | 2089.53 | 2090.75 |
| MELLPLWLCLGFHFLTVG | 382 | 2089.60 | 2090.75 |
| MTWLVLLGTLLCMLRVGLG | 383 | 2089.71 | 2090.75 |
| MSDLGAVISLLLWGRQLFA | 384 | 2090.52 | 2090.75 |
| MIVFIFLAMGLSLENEYT | 385 | 2091.52 | 2090.75 |
| MFGTLLLYCFFLATVPALA | 386 | 2091.61 | 2090.75 |
| MWPLTVPPPLLLLLCSGLAG | 387 | 2091.66 | 2090.75 |

TABLE 14-continued

| Signal Peptide Amino acid sequence | SEQ ID No. | MW | m/z of the corresponding peak |
|---|---|---|---|
| MPVIAGGILAALLLLIVVVLC | 388 | 2091.78 | 2090.75 |
| MAWTPLFLFLLTCCPGSNS | 389 | 2101.54 | 2102.82 |
| MLLLINVILTLWVSCANGQ | 390 | 2101.61 | 2102.82 |
| MLLLINVILTLWVSCANGQ | 391 | 2101.61 | 2102.82 |
| MKGLLPLAWFLACSVPAVQG | 392 | 2101.61 | 2102.82 |
| MTLARFVLALMLGALPEVVG | 393 | 2101.65 | 2102.82 |
| MRPPPALALAGLCLLALPAAAA | 394 | 2101.65 | 2102.82 |
| MDTIFLWSLLLLFFGSQA | 395 | 2102.53 | 2102.82 |
| MSILFYVIFLAYLRGIQG | 396 | 2104.59 | 2102.82 |
| MGWTWRILFLVVIAAGAQS | 397 | 2119.56 | 2121.37 |
| MAAPVPWACCAVLAAAAAVVYA | 398 | 2119.61 | 2121.37 |
| MWGLVRLLLAWLGGWGCMG | 399 | 2119.65 | 2121.37 |
| MLGVLELLLLGAAWLAGPARG | 400 | 2121.62 | 2121.37 |
| MLLLLLLPLLWGRERVEG | 401 | 2121.66 | 2121.37 |
| MRPGLSFLLALLFFLGQAAG | 402 | 2122.61 | 2121.37 |
| MHWKMLLLLLLYYNAEA | 403 | 2122.63 | 2121.37 |
| MAVKLGTLLLALALGLAQPASA | 404 | 2122.65 | 2121.37 |
| MQKVTLGLLVFLAGFPVLDA | 405 | 2132.64 | 2133.94, 2134.56 |
| MAQLWLSCFLLPALVVSVAA | 406 | 2132.66 | 2133.94, 2134.56 |
| MPAIAVLAAAAAAWCFLQVES | 407 | 2133.57 | 2133.94, 2135.18, 2134.56 |
| MAMVSAMSWVLYLWISACA | 408 | 2133.65 | 2133.94, 2135.18, 2134.56 |
| MGSAPWAPVLLLALGLRGLQA | 409 | 2134.62 | 2133.94, 2135.18, 2134.56 |
| MHRLIFVYTLICANFCSC | 410 | 2134.64 | 2133.94, 2135.18, 2134.56 |
| MLLLWVSVVAALALAVLAPGAG | 411 | 2135.69 | 2135.18, 2133.94, 2137.45 |

TABLE 15

| Signal Peptide Amino acid sequence | SEQ ID No. | MW | m/z of the corresponding peak |
|---|---|---|---|
| MACLGFLLPVGFLLLISTVAG | 412 | 2135.71 | 2135.18, 2133.94, 2137.45 |
| MASLGLLLLLLLTALPPLWS | 413 | 2135.73 | 2135.18, 2133.94, 2137.45 |
| MVLLSILRILFLCELVLF | 414 | 2135.80 | 2135.18, 2133.94, 2137.45 |
| MSPAPRPSRCLLLPLLTLGT | 415 | 2136.66 | 2135.18, 2137.45 |
| MRLLWKLVILLPLINSSAG | 416 | 2137.71 | 2137.45 |
| MRFVVALVLLNVAAAGAVPLL | 417 | 2137.71 | 2137.45 |
| MHPGVLAAFLFLSWTHCRA | 418 | 2157.60 | 2159.33 |
| MSEFLLALLTLSGLLPIARV | 419 | 2157.69 | 2159.33 |
| MNAKVVVVLVLVLTALCLSDG | 420 | 2157.71 | 2159.33 |
| METLGALLVLEFLLLSPVEA | 421 | 2158.63 | 2159.33 |

TABLE 15-continued

| Signal Peptide Amino acid sequence | SEQ ID No. | MW | m/z of the corresponding peak |
|---|---|---|---|
| MASSLTCTGVIWALLSFLCAA | 422 | 2158.64 | 2159.33 |
| MAVGKFLLGSLLLLSLQLGQG | 423 | 2158.68 | 2159.33 |
| MWQLLAAACWMLLLGSMYG | 424 | 2158.71 | 2159.33 |
| MGTGGSLLCGCSLVLSCLCPSAS | 425 | 2159.62 | 2159.33 |
| MWLYLAAFVGLYYLLHW | 426 | 2159.63 | 2159.33 |
| MDWTWRILFLVAAATGTHA | 427 | 2160.53 | 2159.33 |
| DLRVATVTLMLAILSSSLAEG | 428 | 2160.56 | 2159.33 |
| MGGRVFLAFCVWLTLPGAET | 429 | 2168.61 | 2169.86 |
| MEFGLSWVFLVALLRGVQC | 430 | 2168.66 | 2169.86 |
| MRVGGAFHLLLVCLSPALLSA | 431 | 2168.70 | 2169.86 |
| MAQSRVLLLLLLLPPQLHL | 432 | 2168.76 | 2169.86 |
| MALRAPALLPLLLLLLPLRA | 433 | 2168.85 | 2169.86 |
| MDPKGLLSLTFVLFLSLAFG | 434 | 2169.66 | 2169.86 |
| MVWRLVLLALWVWPSTQA | 435 | 2169.67 | 2169.86 |
| MDLLWMPLLLVAACVSAVHS | 436 | 2169.71 | 2169.86 |
| MKFLLDILLLLPLLIVCSL | 437 | 2170.88 | 2169.86 |
| MNTLLLVSLSFLYLKEVMG | 438 | 2171.70 | 2169.86 |
| MKAFHTFCVVLLVFGSVSEA | 54 | 2185.64 | 2187.30 |
| MGGTLAWTLLLPLLLRESDS | 55 | 2186.60 | 2187.30 |
| MEFVRALWLGLALALGPGSAGG | 56 | 2186.61 | 2187.30 |
| MRTLFNLLWLALACSPVHT | 57 | 2186.68 | 2187.30 |
| MKILVAFLVVLTIFGIQSHG | 58 | 2186.74 | 2187.30 |
| MEPHLLGLLLGLLLGGTRVLA | 59 | 2186.74 | 2187.30 |
| MRRCRWAALALGLLRLCLA | 60 | 2186.79 | 2187.30 |
| MKFLIFAFFGGVHLLSLCSG | 61 | 2187.70 | 2187.30 |
| MMLLILFLVIICSHISVNQ | 62 | 2187.81 | 2187.30 |
| MTCSPLLLTLLIHCTGSWAQ | 63 | 2188.67 | 2187.30 |
| MVFLKFFCMSFFCHLCQG | 64 | 2188.76 | 2187.30 |
| MLMPLCGLLWWWCCCSG | 65 | 2188.78 | 2187.30 |
| MFQQFQASCLVLFFLVGFA | 66 | 2196.67 | 2196.08, 2196.64 |
| MALAALMIALGSLGLHTWQAQ | 67 | 2196.67 | 2196.08, 2196.64 |
| MAGAVSLLGVVGLLLVSALSGVLG | 68 | 2196.73 | 2196.08, 2196.64 |
| MDTSRLGVLLSLPVLLQLATG | 69 | 2197.67 | 2196.08, 2196.64 |
| MSPSGRLCLLTIVGLILPTRG | 70 | 2197.74 | 2196.08, 2196.64 |

TABLE 16

| Signal Peptide Amino acid sequence | SEQ ID No. | MW | m/z of the corresponding peak |
|---|---|---|---|
| MAAAAWLQVLPVILLLLGAHP | 71 | 2197.76 | 2196.08, 2196.64 |
| MRRLLLVTSLVVVLLWEAGA | 72 | 2239.80 | 2240.20 |
| MAPSAWAICWLLGGLLLHGGSS | 73 | 2240.68 | 2240.20 |
| MVTRAGAGTAVAGAVVVALLSAALA | 74 | 2240.70 | 2240.20 |
| MWPLWRLVSLLALSQALPF | 75 | 2241.77 | 2240.20 |
| MAGVRARAPLPLALLLSLPAAPG | 439 | 2255.80 | 2257.07 |
| MLLPQLCWLPLLAGLLPPVPA | 440 | 2255.91 | 2257.07 |
| MQIPRAALLPLLLLLAAPASA | 441 | 2256.87 | 2257.07 |
| MRLLCGLWLWLSLLKVLQA | 442 | 2256.90 | 2257.07 |
| MSLTVVSMACVGFFLLQGAWP | 443 | 2257.77 | 2257.07 |
| MKLLFPIFASLMLQYQVNT | 444 | 2257.79 | 2257.07 |
| MVPSAGQLALFALGIVLAACQAL | 445 | 2257.79 | 2257.07 |
| MLRLGLCAAALLCVCRPGAVRA | 446 | 2257.89 | 2257.07 |
| MTWKGGGGWMAAVTHGPGITWG | 447 | 2258.61 | 2257.07 |
| MGSLFPLSLLFFLAAAYPGVGS | 448 | 2258.71 | 2257.07 |
| MKSYTPYFILLWSAVGIAKA | 449 | 2259.74 | 2261.04 |
| MKGICSDAILVLATSMWMAFA | 450 | 2259.81 | 2261.04 |
| MSPLLRRLLLAALLQLAPAQA | 451 | 2259.83 | 2261.04 |
| MVFSLKVILFLSLLLSPVLK | 452 | 2260.94 | 2261.04 |
| MLMLMLVAAVTMWLRPLVTA | 453 | 2260.97 | 2261.04 |
| MTSQRSPLAPLLLLSLHGVAAS | 454 | 2262.70 | 2261.04 |
| MAARGSGPRALRLLLLVQLVAG | 455 | 2262.80 | 2261.04 |
| MLGARAWLGRVLLLPRAGAGLA | 456 | 2262.80 | 2261.04 |
| MRLLILALLGICSLTAYIVEG | 457 | 2262.85 | 2261.04 |
| MPLSSHLLPALVLFLAGSSGWA | 458 | 2267.72 | 2269.26 |
| MALAALMIALGSLGLHTWQAQA | 459 | 2267.75 | 2269.26 |
| MPRGFTWLRYLGIFLGVALG | 460 | 2267.77 | 2269.26 |
| MSLASGPGPGWLLFSFGMGLVSG | 461 | 2268.69 | 2269.26 |
| MKMHLQRALVVLALLNFATV | 462 | 2268.87 | 2269.26 |
| MKIATVSVLLPLALCLIQDAAS | 463 | 2270.83 | 2269.26 |
| MKLSVCLLLVTLALCCYQANA | 464 | 2270.88 | 2269.26 |
| MPPWGAALALILAVLALLGLLGP | 465 | 2270.90 | 2269.26 |
| MSGNWVHPGQILIWAIWVLA | 466 | 2291.75 | 2292.01 |
| MRRWAWAAVVVLLGPQLVLL | 467 | 2291.88 | 2292.01 |
| MRLPDVQLWLVLLWALVRA | 468 | 2292.87 | 2292.01 |
| MRCALALSALLLLLSTPPLLPS | 469 | 2293.91 | 2292.01 |
| MDWPHNLLFLLTISIFLGLG | 470 | 2300.80 | 2302.72 |
| MTARGLALGLLLLLLCPAQVFS | 471 | 2300.90 | 2302.72 |

TABLE 16-continued

| Signal Peptide | | | m/z of the |
|---|---|---|---|
| Amino acid sequence | SEQ ID No. | MW | corresponding peak |
| MNCVCRLVLVVLSLWPDTAVA | 472 | 2302.86 | 2302.72 |
| MSRSATLLLCLLGCHVWKAVT | 473 | 2302.86 | 2302.72 |
| MATWALLLLAAMLLGNPGLVFS | 474 | 2302.88 | 2302.72 |
| MPSWIGAVILPLLGLLLSLPAGA | 475 | 2302.90 | 2302.72 |
| MAGRGGSALLALCGALAACGWLLGA | 476 | 2303.81 | 2302.72 |
| MPLWVFFFVILTLSNSSHCS | 477 | 2328.79 | 2330.24 |

TABLE 17

| Signal Peptide | | | m/z of the |
|---|---|---|---|
| Amino acid sequence | SEQ ID No. | MW | corresponding peak |
| MVGQRVLLLVAFLLSGVLLSEA | 478 | 2328.89 | 2330.24 |
| MVLLHWCLLWLLFPLSSRT | 479 | 2328.92 | 2330.24 |
| MVPGVPGAVLTLCLWLAASSGCLA | 480 | 2329.88 | 2330.24, 2331.1 |
| MNRFLLLMSLYLLGSARGTSS | 481 | 2330.80 | 2330.24, 2331.1 |
| MEAAVAAPRPRLLLLVLAAAAAA | 482 | 2330.87 | 2330.24, 2331.1 |
| MGRLVLLWGAAVFLLGGWMALG | 483 | 2331.92 | 2330.24, 2331.1 |
| MAAWGCVAALGAARGLCWRAARA | 484 | 2332.81 | 2331.10 |
| MEALTLWLLPWICQCVSVRA | 485 | 2332.89 | 2331.10 |
| MIHGRSVLHIVASLIILHLSGA | 486 | 2337.86 | 2339.45 |
| MIIKHFFGTVLVLLASTTIFS | 487 | 2338.89 | 2339.45 |
| MPAAMLPYACVLVLLGAHTAPAAG | 488 | 2338.89 | 2339.45, 2340.89 |
| MRIISRQIVLLFSGFWGLAM | 489 | 2338.92 | 2339.45, 2340.89 |
| MGSPRSALSCLLLHLLVLCLQA | 490 | 2338.93 | 2339.45, 2340.89 |
| MTDKSIVILSLMVFHSSFING | 491 | 2339.81 | 2339.45, 2340.89 |
| MPFRLLIPLGLLCALLPQHHG | 492 | 2339.95 | 2339.45, 2340.89 |
| MSLMVVSMARVGFFLLQGAWP | 493 | 2340.91 | 2339.45, 2340.89 |
| MDSWTFCCVSLCILVAKHTDA | 494 | 2343.80 | 2345.00 |
| MAGASRLLFLWLGCFCVSLAQG | 495 | 2343.87 | 2345.00 |
| MEASRWWLLVTVLMAGAHCVA | 496 | 2344.86 | 2345.00 |
| MDPKQTTLLCLVLCLGQRIQA | 497 | 2344.90 | 2345.00 |
| MKLLYLFLAILLAIEEPVISG | 498 | 2346.95 | 2345.00 |
| MRWCLLLIWAQGLRQAPLASG | 499 | 2383.92 | 2385.34 |
| MRLRLRLLALLLLLAPPARA | 500 | 2384.11 | 2385.34 |
| MASHSGPSTSVLFLFCCLGGWLA | 501 | 2384.83 | 2385.34 |
| MDRGPAAVACTLLLALVACLAPASG | 502 | 2384.92 | 2385.34 |
| MRFAWTVLLLGPLQLCALVHC | 503 | 2385.01 | 2385.34 |
| MRGFNLLLFWGCCVMHSWEG | 504 | 2386.88 | 2385.34 |
| MNLRLCVQALLLLWLSLTAVCG | 505 | 2431.07 | 2432.63 |

TABLE 17-continued

| Signal Peptide Amino acid sequence | SEQ ID No. | MW | m/z of the corresponding peak |
|---|---|---|---|
| MPGPWLLLALALTLNLTGVPGGRA | 506 | 2431.97 | 2432.63 |
| MAGGSATTWGYPVALLLLVATLGLG | 507 | 2432.91 | 2432.63 |
| MECLYYFLGFLLLAARLPLDA | 508 | 2432.98 | 2432.63 |
| MKMRFLGLVVCLVLWTLHSEG | 509 | 2433.05 | 2432.63 |
| MKGRGMLVLLLHAVVLGLPSAWA | 510 | 2433.07 | 2432.63 |
| MTPILTVLICLGLSLGPRTHVQA | 511 | 2434.01 | 2432.63 |
| MTPILTVLICLGLSLGPRTHVQA | 512 | 2434.01 | 2432.63 |
| MKDMPLRIHVLLGLAITTLVQA | 513 | 2434.05 | 2432.63 |
| MTCWLCVLSLPLLLLPAAPPPAGG | 514 | 2434.08 | 2432.63 |
| MRSRLPPALAALGAALLLSSIEAE | 515 | 2450.93 | 2452.57 |
| MEQRPRGCAAVAAALLLVLLGARA | 516 | 2451.00 | 2452.57 |
| MSRLSRSLLWAATCLGVLCVLSA | 517 | 2451.02 | 2452.57 |
| MVCSAAPLLLLATTLPLLGSPVAQA | 518 | 2451.04 | 2452.57 |
| MILNWKLLGILVLCLHTRGISG | 519 | 2451.09 | 2452.57 |
| MAPYPCGCHILLLLFCCLAAARA | 520 | 2451.11 | 2452.57 |
| MIIMVIIFLVLLFWENEVND | 521 | 2452.02 | 2452.57 |

TABLE 18

| Signal Peptide Amino acid sequence | SEQ ID No. | MW | m/z of the corresponding peak |
|---|---|---|---|
| MKLHSLISVLLLFVTLIPKGKT | 522 | 2452.13 | 2452.57 |
| MIMFPLFGKISLGILIFVLIEG | 523 | 2452.15 | 2452.57 |
| MTPILTVLICLGLSLGPRTRVQA | 524 | 2453.06 | 2452.57 |
| MAKPRLLVLYFALIVVPAWVSS | 525 | 2474.10 | 2475.26 |
| MEKMLAGCFLLILGQIVLLPAEA | 526 | 2474.14 | 2475.26 |
| MELPFVTHLFLPLVFLTGLCSP | 527 | 2475.06 | 2475.26 |
| MKICSLTLLSFLLLAAQVLLVEG | 528 | 2476.13 | 2475.26 |
| MQRLMMLLATSGACLGLLAVAAVAA | 529 | 2476.14 | 2475.26 |
| MRGAARLGRPGRSCLPGPALRAAAA | 530 | 2476.97 | 2475.26 |
| MERIVICLMVIFLGTLVHKSSS | 531 | 2477.10 | 2475.26 |
| MGRHVATSCHVAWLLVLISGCWG | 532 | 2497.01 | 2497.02 |
| MLLWVQQALLALLLPTLLAQGEA | 533 | 2506.09 | 2506.70 |
| MRRRLWLGLAWLLLARAPDAAG | 534 | 2507.05 | 2506.70 |
| MRKTRLWGLLWMLFVSELRA | 535 | 2507.11 | 2506.70 |
| MKFYSLLLCSLLFSFPFLCHP | 536 | 2507.13 | 2506.70 |
| MAVESQGGRPLVLGLLLCVLGPVVS | 537 | 2508.09 | 2506.70 |
| MAAATRGCRPWGSLLGLLGLVSAAAA | 538 | 2514.02 | 2515.58 |

TABLE 18-continued

| Signal Peptide Amino acid sequence | SEQ ID No. | MW | m/z of the corresponding peak |
|---|---|---|---|
| MAAATRGCRPWGSLLGLLGLVSAAAA | 539 | 2514.02 | 2515.58 |
| MGAPSACRTLVLALAAMLVVPQAET | 540 | 2514.08 | 2515.58 |
| MAGLGASLHVWGWLMLGSCLLARA | 541 | 2514.08 | 2515.58 |
| MASLGQILFWSIISIIIILAGAIA | 542 | 2515.14 | 2515.58 |
| MGQLCWLPLLAPLLLLRPPGVQS | 543 | 2516.16 | 2515.58 |
| MCLTDEWGFLFFFFFLGVPEA | 544 | 2516.97 | 2515.58 |
| MRTHTRGAPSVFFIYLLCFVSA | 545 | 2517.02 | 2515.58 |
| MSDLLSIYSAPVVVSTVLHMLQI | 546 | 2517.05 | 2515.58 |
| MFLSKPSVYICLFTCVLQLSHS | 547 | 2517.08 | 2515.58 |
| MRLHLLLLILLLFSILLSPVRG | 548 | 2531.28 | 2532.19 |
| MLSQLAMLQGSLLLVVATMSVAQQ | 549 | 2533.12 | 2532.19 |
| MPAGVPMSTYLKMFAASLLAMCAGA | 550 | 2533.17 | 2532.19 |
| MDLWNLSWFLFLDALLVISGLA | 551 | 2538.05 | 2539.62 |
| MGLSAAAPLWGPPGLLLAIALHPALS | 552 | 2538.10 | 2539.62 |
| MWGLAGGRLFGIFSAPVLVAVVCCA | 553 | 2538.15 | 2539.62 |
| MRVAGAAKLVVAVAVFLLTFYVIS | 554 | 2539.17 | 2539.62, 2540.74 |
| MDMRVPAQLLGLLLLWLPGVRF | 555 | 2539.20 | 2539.62, 2540.74 |
| MHLARLVGSCSLLLLLGALSGWAAS | 556 | 2540.10 | 2539.62, 2540.74 |
| MGLPRGPLASLLLLQVCWLQCAAS | 557 | 2541.15 | 2540.74, 2539.62 |
| GGIPGDLRVATVTLMLAILSSSLAEG | 558 | 2542.00 | 2543.60, 2540.74 |
| MAVMAPRTLLLLLSGALALTQTWA | 559 | 2542.15 | 2543.60, 2540.74 |
| MAVMAPRTLLLLLSGALALTQTWA | 560 | 2542.15 | 2543.60, 2540.74 |
| MAVMAPRTLLLLLSGALALTQTWA | 561 | 2542.15 | 2543.60, 2540.74 |
| MKHTLALLAPLLGLGLALSQLAAG | 562 | 2543.16 | 2543.60 |
| MELLPPLPQSFLLLLLLPAKPAAG | 563 | 2543.20 | 2543.60 |
| MQSPWKILTVAPLFLLLSLQSSA | 564 | 2544.10 | 2543.60, 2545.55 |
| MQPPSLLLLLLLLLLLCVSVVRP | 565 | 2544.34 | 2543.60, 2545.55 |

TABLE 19

| Signal Peptide Amino acid sequence | SEQ ID No. | MW | m/z of the corresponding peak |
|---|---|---|---|
| MRTPQLALLQVFFLVFPDGVRP | 566 | 2545.09 | 2545.55, 2543.6 |
| MARQPPPPWVHAAFLLCLLSLGGA | 567 | 2546.10 | 2545.55 |
| MDVCVRLALWLLWGLLLHQGQS | 568 | 2552.11 | 2553.90 |
| MQFRLFSFALIILNCMDYSHC | 569 | 2553.09 | 2553.90 |
| MGSRGQGLLLAYCLLLAFASGLVLS | 570 | 2554.12 | 2553.90 |
| MFLATLYFALPLLDLLLSAEVSGG | 571 | 2555.08 | 2553.90 |
| MQRLVLLLAISLLLYQDLPVRS | 572 | 2555.17 | 2553.90 |

TABLE 19-continued

| Signal Peptide Amino acid sequence | SEQ ID No. | MW | m/z of the corresponding peak |
|---|---|---|---|
| MRLWKAVVVTLAFMSVDICVTTA | 573 | 2555.17 | 2553.90 |
| MRQKAVSLFLCYLLLFTCSGVEA | 574 | 2593.18 | 2594.54 |
| MPPPRTGRGLLWLGLVLSSVCVALG | 575 | 2593.20 | 2594.54 |
| MLFRNRFLLLLALAALLAFVSLS | 576 | 2593.26 | 2594.54 |
| MLPLPSCSLPILLLFLLPSVPIES | 577 | 2593.28 | 2594.54 |
| MKAMPWNWTCLLSHLLMVGMGSS | 578 | 2594.21 | 2594.54 |
| MALGKVLAMALVLALAVLGSLSPGARA | 579 | 2594.27 | 2594.54 |
| MVPSSPRALFLLLLILACPEPRAS | 580 | 2595.22 | 2594.54 |
| MCRIAGALRTLLPLLAALLQASVEA | 581 | 2595.22 | 2594.54 |
| MNNFRATILFWAAAAWAKSGKPSG | 582 | 2596.01 | 2594.54 |
| MAVWLAQWLGPLLLVSLWGLLAPA | 583 | 2619.26 | 2620.55, 2621.08 |
| MEAARALRLLLVVCGCLALPPLAEP | 584 | 2620.29 | 2620.55, 2621.08 |
| MDLGKPMKSVLVVALLVIFQVCLC | 585 | 2620.39 | 2620.55, 2621.08 |
| MPSLPAPPAPLLLLGLLLLGSRPARG | 586 | 2621.28 | 2620.55, 2621.08 |
| MRVMAPRTLILLLSGALALTETWA | 587 | 2628.25 | 2629.71 |
| MRVMAPRTLILLLSGALALTETWA | 588 | 2628.25 | 2629.71 |
| MRVMAPRTLILLLSGALALTETWA | 589 | 2628.25 | 2629.71 |
| MRVMAPRTLILLLSGALALTETWA | 590 | 2628.25 | 2629.71 |
| MRVMAPRTLILLLSGALALTETWA | 591 | 2628.25 | 2629.71 |
| MTSCGQQSLNVLAVLFSLLFSAVLS | 592 | 2629.14 | 2629.71 |
| MATRSVLLALVVLNLLFYVPPGRS | 593 | 2630.24 | 2629.71, 2631.23 |
| MARFLTLCTWLLLLGPGLLATVRA | 594 | 2630.31 | 2629.71, 2631.23 |
| MHTLTGFSLVSLLSFGYLSWDWA | 595 | 2632.04 | 2631.23 |
| MHWGTLCGFLWLWPYLFYVQA | 596 | 2632.15 | 2631.23 |
| MVVMAPRTLFLLLSGALTLTETWA | 597 | 2635.23 | 2635.51 |
| MISSVKLNLILVLSLSTMHVFWC | 598 | 2635.30 | 2635.51 |
| MQGRVAGSCAPLGLLLVCLHLPGLFA | 599 | 2637.28 | 2635.51 |
| MTPPKLRASLSPSLLLLLSGCLLAAA | 600 | 2637.29 | 2635.51 |
| MNYSSFLRIWVSFIFALVQHQA | 601 | 2658.12 | 2659.81 |
| MRPRAPACAAAALGLCSLLLLLAPGHA | 602 | 2658.30 | 2659.81 |
| MMSPSQASLLFLNVCIFICGEAVQG | 603 | 2659.21 | 2659.81 |
| MAVSQGDGTLCFVLLLCCWQETEL | 604 | 2660.16 | 2659.81 |
| MKMQKGNVLLMFGLLLHLEAATNS | 605 | 2660.27 | 2659.81 |
| MPSSTAMAVGALSSSLLVTCCLMVALC | 606 | 2660.33 | 2659.81 |
| MAQRMTTQLLLLLVWVAVVGEAQT | 607 | 2672.25 | 2673.96 |
| MRLLVLSSLLCILLLCFSIFSTEG | 608 | 2672.36 | 2673.96 |
| MAAAAIPALLLCLPLLFLLFGWSRA | 609 | 2672.39 | 2673.96 |

TABLE 20

| Signal Peptide | | | m/z of the |
|---|---|---|---|
| Amino acid sequence | SEQ ID No. | MW | corresponding peak |
| MERPLCSHLCSCLAMLALLSPLSLA | 610 | 2673.35 | 2673.96, 2674.65 |
| MPALRPALLWALLALWLCCAAPAHA | 611 | 2673.36 | 2673.96, 2674.65 |
| MESGHLLWALLFMQSLWPQLTDG | 612 | 2674.14 | 2673.96, 2674.65 |
| MGGCTVKPQLLLLALVLHPWNPCLG | 613 | 2674.34 | 2673.96, 2674.65 |
| MALSSAWRSVLPLWLLWSAACSRA | 614 | 2676.21 | 2674.65 |
| MWGFRLLRSPPLLLLLPQLGIGNA | 615 | 2676.31 | 2674.65 |
| MATSTGRWLLLRLALFGFLWEASG | 616 | 2697.20 | 2698.27 |
| MAWGGVHTCCFHLCCCCSWPQGAVP | 617 | 2697.26 | 2698.27 |
| MRVTAPRTLLLLLWGALALTETWA | 618 | 2697.29 | 2698.27 |
| MGGPAAPRGAGRLRALLLALVVAGIPAGA | 619 | 2697.29 | 2698.27 |
| MLAASIFRPTLLLCWLAAPWPTQP | 620 | 2697.31 | 2698.27 |
| MRQRLLPSVTSLLLVALLFPGSSQA | 621 | 2698.27 | 2698.27 |
| MEAGEGKERVPKQRQVLIFFVLLGIAQASC | 622 | 3318.96 | 3319.44 |
| MARFPKADLAAAGVMLLCHFFTDQFQFADG | 623 | 3319.88 | 3319.44 |
| MDYHWRGELGSWRLLLLLLLLAAWKVGSG | 624 | 3355.02 | 3353.34 |

Example 3: Peptide Synthesis

Synthetic peptides comprising the amino acid sequences represented by SEQ ID NOS: 1 to 75 described above were synthesized by solid-phase synthesis (Fmoc method) using a commercial peptide synthesizer (made by Intavis AG) according to the manual. In the explanations below, these synthetic peptides are called peptides 1 to 75. The mode of use of the peptide synthesizer is not explained in detail because it is not a feature of the present invention.

Example 4: Preparation of Liquid Composition

The synthetic peptides (synthetic marker peptides) of peptides 1 to 75 above were each dissolved in 0.1% TFA/50% ACN aqueous solution to a peptide concentration of 1 µmol/mL, to obtain liquid compositions (Alzheimer's testing compositions) having the synthetic marker peptides disclosed here as principal components.

Example 5: Preparation of Alzheimer's Testing Chips

Alzheimer's testing chips were prepared comprising the synthetic peptides (synthetic marker peptides) of peptides 1 to 75 above immobilized on substrates. For the substrate, EVA film was affixed to a measurement plate commonly used in MALDI MS. That is, this was a plate-shaped substrate in which the surface on which the synthetic marker peptide was immobilized was made of thermoplastic resin.

Each Alzheimer's testing composition was first diluted 100 times with 0.1% TFA/50% ACN aqueous solution, to prepare a synthetic marker peptide dilution. This synthetic marker peptide dilution was then mixed at a volume ratio of 1:1 with matrix liquid. A 0.1% TFA/50% ACN aqueous solution containing 5 mg/mL sinapinic acid (CHCA) was used as the matrix liquid.

2 µL of the mixed solution obtained by mixing this matrix liquid with the synthetic marker peptide dilution was then dripped onto the substrate, and vacuum dried to prepare an Alzheimer's testing chip.

INDUSTRIAL APPLICABILITY

As discussed above, data about whether a test subject suffers from or has developed Alzheimer's (typically, data showing whether there is a strong likelihood that the test subject suffers from or has developed Alzheimer's) can be obtained by the method for aiding Alzheimer's detection disclosed here. That is, Alzheimer's can be detected with a high degree of accuracy by the method for aiding Alzheimer's detection disclosed here. Consequently, the method for aiding Alzheimer's detection disclosed here can be used favorably for predicting, diagnosing (early diagnosis) and initiating treatment for Alzheimer's, and as a follow-up indicator after the start of treatment (typically, as an indicator for evaluating the effects of treatment).

Moreover, the AD biomarker disclosed here can be used favorably as an indicator for detecting (diagnosing) with a high degree of accuracy whether a test subject suffers from or has developed Alzheimer's. That is, the synthetic marker peptide disclosed here (or an Alzheimer's testing composition, Alzheimer's testing kit or Alzheimer's testing chip containing the synthetic marker peptide) can be used favorably for the purpose of detecting (diagnosing) Alzheimer's with a high degree of accuracy.

(Sequence Listing Free Text)
SEQ ID NOS: 1 to 624 Peptides

The invention claimed is:

1. A method for aiding detection of Alzheimer's disease, the method comprising:

analyzing to determine a presence or absence of an Alzheimer's-associated signal peptide or analyzing to determine a degree of abundance of the Alzheimer's-associated signal peptide when the Alzheimer's-associated signal peptide is present in a bodily fluid from a test subject, and comparing the presence or absence of the Alzheimer's-associated signal peptide or the degree of abundance of the Alzheimer's-associated signal peptide in the bodily fluid from the test subject with a reference level set based on results obtained by analyzing the presence or absence of the Alzheimer's-associated signal peptide or the degree of abundance of the Alzheimer's-associated signal peptide in a bodily fluid from at least one healthy subject, wherein a molecular weight of the Alzheimer's-associated signal peptide is: $1629.17\pm2$, $1767.38\pm2$, $1900.43\pm2$, $1933.29\pm2$, $1966.96\pm2$, $1996.12\pm2$, $2187.30\pm2$, $2196.08\pm2$, $2196.64\pm2$, or $2240.20\pm2$, wherein an amino acid sequence constituting the Alzheimer's-associated signal peptide is any of the amino acid sequences represented by SEQ ID NOS: 1 to 75;

and wherein analyzing to determine the presence or absence of the Alzheimer's-associated signal peptide or to determine the degree of abundance of the Alzheimer's-associated signal peptide in the bodily fluid from the test subject comprises testing with a mass spectrometer and immobilizing the bodily fluid on a thermoplastic resin before the presence or absence of the Alzheimer's-associated signal peptide or the degree of abundance of the Alzheimer's-associated signal peptide in the bodily fluid is tested, wherein the presence or absence of the Alzheimer's-associated signal peptide or the degree of abundance of the Alzheimer's-associated signal peptide in the bodily fluid immobilized on the thermoplastic resin is determined by testing with a matrix assisted laser desorption/ionization-time-of-flight mass spectrometry.

2. The method according to claim 1, wherein at least 10 kinds of Alzheimer's-associated signal peptides with molecular weights differing by at least 3 from each other are tested for the bodily fluid from the test subject.

3. The method according to claim 1, wherein the bodily fluid is cerebrospinal fluid.

* * * * *

```
                             SEQUENCE LISTING

<160> NUMBER OF SEQ ID NOS: 624

<210> SEQ ID NO 1
<211> LENGTH: 14
<212> TYPE: PRT
<213> ORGANISM: Homo sapiens

<400> SEQUENCE: 1

Met Leu Leu Pro Leu Leu Leu Leu Pro Met Cys Trp Ala
1               5                   10

<210> SEQ ID NO 2
<211> LENGTH: 16
<212> TYPE: PRT
<213> ORGANISM: Homo sapiens

<400> SEQUENCE: 2

Met Leu Leu Ile Leu Leu Ser Val Ala Leu Leu Ala Leu Ser Ser Ala
1               5                   10                  15

<210> SEQ ID NO 3
<211> LENGTH: 16
<212> TYPE: PRT
<213> ORGANISM: Homo sapiens

<400> SEQUENCE: 3

Met Leu Leu Ile Leu Leu Ser Val Ala Leu Leu Ala Leu Ser Ser Ala
1               5                   10                  15

<210> SEQ ID NO 4
<211> LENGTH: 19
<212> TYPE: PRT
<213> ORGANISM: Homo sapiens

<400> SEQUENCE: 4

Met Arg Ser Leu Gly Ala Leu Leu Leu Leu Ser Ala Cys Leu Ala
1               5                   10                  15

Val Ser Ala

<210> SEQ ID NO 5
<211> LENGTH: 19
<212> TYPE: PRT
<213> ORGANISM: Homo sapiens

<400> SEQUENCE: 5

Met Lys Leu Ala Ser Gly Phe Leu Val Leu Trp Leu Ser Leu Gly Gly
1               5                   10                  15

Gly Leu Ala

<210> SEQ ID NO 6
<211> LENGTH: 17
<212> TYPE: PRT
<213> ORGANISM: Homo sapiens

<400> SEQUENCE: 6

Met Lys Val Leu Leu Arg Leu Ile Cys Phe Ile Ala Leu Leu Ile Ser
1               5                   10                  15

Ser

<210> SEQ ID NO 7
```

```
<211> LENGTH: 18
<212> TYPE: PRT
<213> ORGANISM: Homo sapiens

<400> SEQUENCE: 7

Met Trp Leu Arg Ala Phe Ile Leu Ala Thr Leu Ser Ala Ser Ala Ala
1               5                   10                  15

Trp Gly

<210> SEQ ID NO 8
<211> LENGTH: 17
<212> TYPE: PRT
<213> ORGANISM: Homo sapiens

<400> SEQUENCE: 8

Met Met Arg Glu Trp Val Leu Leu Met Ser Val Leu Leu Cys Gly Leu
1               5                   10                  15

Ala

<210> SEQ ID NO 9
<211> LENGTH: 20
<212> TYPE: PRT
<213> ORGANISM: Homo sapiens

<400> SEQUENCE: 9

Met Arg Thr Ala Leu Leu Leu Leu Ala Ala Leu Ala Val Ala Thr Gly
1               5                   10                  15

Pro Ala Leu Thr
            20

<210> SEQ ID NO 10
<211> LENGTH: 20
<212> TYPE: PRT
<213> ORGANISM: Homo sapiens

<400> SEQUENCE: 10

Met Gln Pro Thr Leu Leu Leu Ser Leu Leu Gly Ala Val Gly Leu Ala
1               5                   10                  15

Ala Val Asn Ser
            20

<210> SEQ ID NO 11
<211> LENGTH: 21
<212> TYPE: PRT
<213> ORGANISM: Homo sapiens

<400> SEQUENCE: 11

Met Met Leu His Ser Ala Leu Gly Leu Cys Leu Leu Leu Val Thr Val
1               5                   10                  15

Ser Ser Asn Leu Ala
            20

<210> SEQ ID NO 12
<211> LENGTH: 19
<212> TYPE: PRT
<213> ORGANISM: Homo sapiens

<400> SEQUENCE: 12

Met Arg Leu Phe Leu Trp Asn Ala Val Leu Thr Leu Phe Val Thr Ser
1               5                   10                  15

Leu Ile Gly
```

<210> SEQ ID NO 13
<211> LENGTH: 21
<212> TYPE: PRT
<213> ORGANISM: Homo sapiens

<400> SEQUENCE: 13

Met Ala Leu Pro Val Thr Ala Leu Leu Leu Pro Leu Ala Leu Leu Leu
1               5                   10                  15

His Ala Ala Arg Pro
            20

<210> SEQ ID NO 14
<211> LENGTH: 19
<212> TYPE: PRT
<213> ORGANISM: Homo sapiens

<400> SEQUENCE: 14

Met Ile Phe Leu Leu Leu Met Leu Ser Leu Glu Leu Gln Leu His Gln
1               5                   10                  15

Ile Ala Ala

<210> SEQ ID NO 15
<211> LENGTH: 22
<212> TYPE: PRT
<213> ORGANISM: Homo sapiens

<400> SEQUENCE: 15

Met Arg Gly Met Lys Leu Leu Gly Ala Leu Leu Ala Leu Ala Ala Leu
1               5                   10                  15

Leu Gln Gly Ala Val Ser
            20

<210> SEQ ID NO 16
<211> LENGTH: 20
<212> TYPE: PRT
<213> ORGANISM: Homo sapiens

<400> SEQUENCE: 16

Met Val Leu Gln Thr Gln Val Phe Ile Ser Leu Leu Leu Trp Ile Ser
1               5                   10                  15

Gly Ala Tyr Gly
            20

<210> SEQ ID NO 17
<211> LENGTH: 20
<212> TYPE: PRT
<213> ORGANISM: Homo sapiens

<400> SEQUENCE: 17

Met Val Leu Gln Thr Gln Val Phe Ile Ser Leu Leu Leu Trp Ile Ser
1               5                   10                  15

Gly Ala Tyr Gly
            20

<210> SEQ ID NO 18
<211> LENGTH: 20
<212> TYPE: PRT
<213> ORGANISM: Homo sapiens

<400> SEQUENCE: 18

Met Val Leu Gln Thr Gln Val Phe Ile Ser Leu Leu Leu Trp Ile Ser
1               5                   10                  15

<210> SEQ ID NO 19
<211> LENGTH: 20
<212> TYPE: PRT
<213> ORGANISM: Homo sapiens

<400> SEQUENCE: 19

Met Met Trp Pro Met His Thr Pro Leu Leu Leu Thr Ala Leu Met
1               5                   10                  15
Val Ala Val Ala
            20

<210> SEQ ID NO 20
<211> LENGTH: 20
<212> TYPE: PRT
<213> ORGANISM: Homo sapiens

<400> SEQUENCE: 20

Met Ser Pro Phe Leu Tyr Leu Val Leu Leu Val Leu Gly Leu His Ala
1               5                   10                  15
Thr Ile His Cys
            20

<210> SEQ ID NO 21
<211> LENGTH: 21
<212> TYPE: PRT
<213> ORGANISM: Homo sapiens

<400> SEQUENCE: 21

Met Arg Pro Ala Phe Ala Leu Cys Leu Leu Trp Gln Ala Leu Trp Pro
1               5                   10                  15
Gly Pro Gly Gly Gly
            20

<210> SEQ ID NO 22
<211> LENGTH: 20
<212> TYPE: PRT
<213> ORGANISM: Homo sapiens

<400> SEQUENCE: 22

Met Asn Leu Gln Pro Ile Phe Trp Ile Gly Leu Ile Ser Ser Val Cys
1               5                   10                  15
Cys Val Phe Ala
            20

<210> SEQ ID NO 23
<211> LENGTH: 16
<212> TYPE: PRT
<213> ORGANISM: Homo sapiens

<400> SEQUENCE: 23

Met Leu Leu Ile Leu Leu Ser Val Ala Leu Leu Ala Leu Ser Ser Ala
1               5                   10                  15

<210> SEQ ID NO 24
<211> LENGTH: 16
<212> TYPE: PRT
<213> ORGANISM: Homo sapiens

<400> SEQUENCE: 24

Met Leu Leu Ile Leu Leu Ser Val Ala Leu Ala Leu Ser Ser Ala
1               5                   10                  15

<210> SEQ ID NO 25
<211> LENGTH: 16
<212> TYPE: PRT
<213> ORGANISM: Homo sapiens

<400> SEQUENCE: 25

Met Thr Leu Arg Leu Leu Val Ala Ala Leu Cys Ala Gly Ile Leu Ala
1               5                   10                  15

<210> SEQ ID NO 26
<211> LENGTH: 15
<212> TYPE: PRT
<213> ORGANISM: Homo sapiens

<400> SEQUENCE: 26

Met Met Leu Arg Leu Leu Ser Ser Leu Leu Val Ala Val Ala
1               5                   10                  15

<210> SEQ ID NO 27
<211> LENGTH: 15
<212> TYPE: PRT
<213> ORGANISM: Homo sapiens

<400> SEQUENCE: 27

Met Met Leu Arg Leu Leu Ser Ser Leu Leu Val Ala Val Ala
1               5                   10                  15

<210> SEQ ID NO 28
<211> LENGTH: 15
<212> TYPE: PRT
<213> ORGANISM: Homo sapiens

<400> SEQUENCE: 28

Met Val Leu Leu Leu Leu Val Ala Ile Pro Leu Leu Val His Ser
1               5                   10                  15

<210> SEQ ID NO 29
<211> LENGTH: 18
<212> TYPE: PRT
<213> ORGANISM: Homo sapiens

<400> SEQUENCE: 29

Met Ala Val Val Pro Leu Leu Leu Gly Gly Leu Trp Ser Ala Val
1               5                   10                  15

Gly Ala

<210> SEQ ID NO 30
<211> LENGTH: 17
<212> TYPE: PRT
<213> ORGANISM: Homo sapiens

<400> SEQUENCE: 30

Met Leu Leu Arg Leu Leu Leu Ala Trp Ala Ala Ala Gly Pro Thr Leu
1               5                   10                  15

Gly

<210> SEQ ID NO 31
<211> LENGTH: 18
<212> TYPE: PRT
<213> ORGANISM: Homo sapiens

```
<400> SEQUENCE: 31

Met Pro Leu Ser Pro Gly Leu Leu Leu Leu Leu Ser Gly Ala Thr
1               5                   10                  15

Ala Thr

<210> SEQ ID NO 32
<211> LENGTH: 16
<212> TYPE: PRT
<213> ORGANISM: Homo sapiens

<400> SEQUENCE: 32

Met Gly Trp Leu Phe Leu Lys Val Leu Leu Ala Gly Val Ser Phe Ser
1               5                   10                  15

<210> SEQ ID NO 33
<211> LENGTH: 19
<212> TYPE: PRT
<213> ORGANISM: Homo sapiens

<400> SEQUENCE: 33

Met Gly Ala Ala Gly Leu Leu Gly Val Phe Leu Ala Leu Val Ala Pro
1               5                   10                  15

Gly Val Leu

<210> SEQ ID NO 34
<211> LENGTH: 17
<212> TYPE: PRT
<213> ORGANISM: Homo sapiens

<400> SEQUENCE: 34

Met Gly Leu Leu Leu Leu Val Pro Leu Leu Leu Leu Pro Gly Ser Tyr
1               5                   10                  15

Gly

<210> SEQ ID NO 35
<211> LENGTH: 18
<212> TYPE: PRT
<213> ORGANISM: Homo sapiens

<400> SEQUENCE: 35

Met Val Arg Leu Cys Gln Ala Leu Leu Leu Val Ala Thr Val Ala
1               5                   10                  15

Leu Ala

<210> SEQ ID NO 36
<211> LENGTH: 19
<212> TYPE: PRT
<213> ORGANISM: Homo sapiens

<400> SEQUENCE: 36

Met Ala Leu Gln Leu Trp Ala Leu Thr Leu Leu Gly Leu Leu Gly Ala
1               5                   10                  15

Gly Ala Ser

<210> SEQ ID NO 37
<211> LENGTH: 17
<212> TYPE: PRT
<213> ORGANISM: Homo sapiens

<400> SEQUENCE: 37

Met Ala Phe Val Leu Ile Leu Val Leu Ser Phe Tyr Glu Leu Val Ser
```

```
                1               5                   10                  15

Gly

<210> SEQ ID NO 38
<211> LENGTH: 16
<212> TYPE: PRT
<213> ORGANISM: Homo sapiens

<400> SEQUENCE: 38

Met Arg Leu Ile Leu Phe Phe Gly Ala Leu Phe Gly His Ile Tyr Cys
1               5                   10                  15

<210> SEQ ID NO 39
<211> LENGTH: 17
<212> TYPE: PRT
<213> ORGANISM: Homo sapiens

<400> SEQUENCE: 39

Met Leu Pro Trp Leu Leu Val Phe Ser Ala Leu Gly Ile Gln Ala Trp
1               5                   10                  15

Gly

<210> SEQ ID NO 40
<211> LENGTH: 19
<212> TYPE: PRT
<213> ORGANISM: Homo sapiens

<400> SEQUENCE: 40

Met Lys Thr Leu Ala Gly Leu Val Leu Gly Leu Val Ile Phe Asp Ala
1               5                   10                  15

Ala Val Thr

<210> SEQ ID NO 41
<211> LENGTH: 19
<212> TYPE: PRT
<213> ORGANISM: Homo sapiens

<400> SEQUENCE: 41

Met Gly Pro Gly Val Leu Leu Leu Leu Val Ala Thr Ala Trp His
1               5                   10                  15

Gly Gln Gly

<210> SEQ ID NO 42
<211> LENGTH: 18
<212> TYPE: PRT
<213> ORGANISM: Homo sapiens

<400> SEQUENCE: 42

Met Ala Arg Val Pro Pro Val Gly Ala Leu Leu Leu Leu Arg Gly Ser
1               5                   10                  15

Arg Gln

<210> SEQ ID NO 43
<211> LENGTH: 19
<212> TYPE: PRT
<213> ORGANISM: Homo sapiens

<400> SEQUENCE: 43

Met Gly Arg Gly Val Arg Val Leu Leu Leu Leu Ser Leu Leu His Cys
1               5                   10                  15

Ala Gly Gly
```

<210> SEQ ID NO 44
<211> LENGTH: 18
<212> TYPE: PRT
<213> ORGANISM: Homo sapiens

<400> SEQUENCE: 44

Met Lys Met Leu Leu Leu Leu His Cys Leu Gly Val Phe Leu Ser Cys
1               5                   10                  15

Ser Gly

<210> SEQ ID NO 45
<211> LENGTH: 20
<212> TYPE: PRT
<213> ORGANISM: Homo sapiens

<400> SEQUENCE: 45

Met Ala Ser Leu Leu Pro Leu Leu Cys Leu Cys Val Val Ala Ala His
1               5                   10                  15

Leu Ala Gly Ala
            20

<210> SEQ ID NO 46
<211> LENGTH: 19
<212> TYPE: PRT
<213> ORGANISM: Homo sapiens

<400> SEQUENCE: 46

Met Ala Leu Leu Val Leu Gly Leu Val Ser Cys Thr Phe Phe Leu Ala
1               5                   10                  15

Val Asn Gly

<210> SEQ ID NO 47
<211> LENGTH: 18
<212> TYPE: PRT
<213> ORGANISM: Homo sapiens

<400> SEQUENCE: 47

Met Ser Leu Leu Leu Leu Leu Leu Leu Val Ser Tyr Tyr Val Gly Thr
1               5                   10                  15

Leu Gly

<210> SEQ ID NO 48
<211> LENGTH: 20
<212> TYPE: PRT
<213> ORGANISM: Homo sapiens

<400> SEQUENCE: 48

Met Arg Ala Gly Pro Gly Pro Thr Val Thr Leu Ala Leu Val Leu Ala
1               5                   10                  15

Val Ala Trp Ala
            20

<210> SEQ ID NO 49
<211> LENGTH: 19
<212> TYPE: PRT
<213> ORGANISM: Homo sapiens

<400> SEQUENCE: 49

Met Ala Gly Ile Pro Gly Leu Leu Phe Leu Leu Phe Phe Leu Leu Cys
1               5                   10                  15

Ala Val Gly

<210> SEQ ID NO 50
<211> LENGTH: 19
<212> TYPE: PRT
<213> ORGANISM: Homo sapiens

<400> SEQUENCE: 50

Met Val Leu Ser Leu Thr Gly Leu Ile Ala Phe Ser Phe Leu Gln Ala
1               5                   10                  15

Thr Leu Ala

<210> SEQ ID NO 51
<211> LENGTH: 17
<212> TYPE: PRT
<213> ORGANISM: Homo sapiens

<400> SEQUENCE: 51

Met Leu Leu Trp Leu Leu Leu Leu Ile Leu Thr Pro Gly Arg Glu Gln
1               5                   10                  15

Ser

<210> SEQ ID NO 52
<211> LENGTH: 20
<212> TYPE: PRT
<213> ORGANISM: Homo sapiens

<400> SEQUENCE: 52

Met Val Leu Leu Leu Val Ile Leu Ile Pro Val Leu Val Ser Ser Ala
1               5                   10                  15

Gly Thr Ser Ala
            20

<210> SEQ ID NO 53
<211> LENGTH: 19
<212> TYPE: PRT
<213> ORGANISM: Homo sapiens

<400> SEQUENCE: 53

Met Val Cys Gly Cys Ser Ala Leu Leu Pro Leu Pro Asn Pro Arg Pro
1               5                   10                  15

Thr Met Pro

<210> SEQ ID NO 54
<211> LENGTH: 20
<212> TYPE: PRT
<213> ORGANISM: Homo sapiens

<400> SEQUENCE: 54

Met Lys Ala Phe His Thr Phe Cys Val Val Leu Leu Val Phe Gly Ser
1               5                   10                  15

Val Ser Glu Ala
            20

<210> SEQ ID NO 55
<211> LENGTH: 20
<212> TYPE: PRT
<213> ORGANISM: Homo sapiens

<400> SEQUENCE: 55

Met Gly Gly Thr Leu Ala Trp Thr Leu Leu Leu Pro Leu Leu Leu Arg
1               5                   10                  15

Glu Ser Asp Ser
            20

<210> SEQ ID NO 56
<211> LENGTH: 22
<212> TYPE: PRT
<213> ORGANISM: Homo sapiens

<400> SEQUENCE: 56

Met Glu Phe Val Arg Ala Leu Trp Leu Gly Leu Ala Leu Ala Leu Gly
1               5                   10                  15

Pro Gly Ser Ala Gly Gly
            20

<210> SEQ ID NO 57
<211> LENGTH: 19
<212> TYPE: PRT
<213> ORGANISM: Homo sapiens

<400> SEQUENCE: 57

Met Arg Thr Leu Phe Asn Leu Leu Trp Leu Ala Leu Ala Cys Ser Pro
1               5                   10                  15

Val His Thr

<210> SEQ ID NO 58
<211> LENGTH: 20
<212> TYPE: PRT
<213> ORGANISM: Homo sapiens

<400> SEQUENCE: 58

Met Lys Ile Leu Val Ala Phe Leu Val Val Leu Thr Ile Phe Gly Ile
1               5                   10                  15

Gln Ser His Gly
            20

<210> SEQ ID NO 59
<211> LENGTH: 21
<212> TYPE: PRT
<213> ORGANISM: Homo sapiens

<400> SEQUENCE: 59

Met Glu Pro His Leu Leu Gly Leu Leu Leu Gly Leu Leu Leu Gly Gly
1               5                   10                  15

Thr Arg Val Leu Ala
            20

<210> SEQ ID NO 60
<211> LENGTH: 19
<212> TYPE: PRT
<213> ORGANISM: Homo sapiens

<400> SEQUENCE: 60

Met Arg Arg Cys Arg Trp Ala Ala Leu Ala Leu Gly Leu Leu Arg Leu
1               5                   10                  15

Cys Leu Ala

<210> SEQ ID NO 61
<211> LENGTH: 20
<212> TYPE: PRT
<213> ORGANISM: Homo sapiens

<400> SEQUENCE: 61

```
Met Lys Phe Leu Ile Phe Ala Phe Gly Gly Val His Leu Leu Ser
1               5                   10                  15

Leu Cys Ser Gly
            20

<210> SEQ ID NO 62
<211> LENGTH: 19
<212> TYPE: PRT
<213> ORGANISM: Homo sapiens

<400> SEQUENCE: 62

Met Met Leu Leu Ile Leu Phe Leu Val Ile Ile Cys Ser His Ile Ser
1               5                   10                  15

Val Asn Gln

<210> SEQ ID NO 63
<211> LENGTH: 20
<212> TYPE: PRT
<213> ORGANISM: Homo sapiens

<400> SEQUENCE: 63

Met Thr Cys Ser Pro Leu Leu Leu Thr Leu Leu Ile His Cys Thr Gly
1               5                   10                  15

Ser Trp Ala Gln
            20

<210> SEQ ID NO 64
<211> LENGTH: 18
<212> TYPE: PRT
<213> ORGANISM: Homo sapiens

<400> SEQUENCE: 64

Met Val Phe Leu Lys Phe Phe Cys Met Ser Phe Phe Cys His Leu Cys
1               5                   10                  15

Gln Gly

<210> SEQ ID NO 65
<211> LENGTH: 18
<212> TYPE: PRT
<213> ORGANISM: Homo sapiens

<400> SEQUENCE: 65

Met Leu Met Pro Leu Cys Gly Leu Leu Trp Trp Trp Cys Cys Cys
1               5                   10                  15

Ser Gly

<210> SEQ ID NO 66
<211> LENGTH: 19
<212> TYPE: PRT
<213> ORGANISM: Homo sapiens

<400> SEQUENCE: 66

Met Phe Gln Gln Phe Gln Ala Ser Cys Leu Val Leu Phe Phe Leu Val
1               5                   10                  15

Gly Phe Ala

<210> SEQ ID NO 67
<211> LENGTH: 21
<212> TYPE: PRT
<213> ORGANISM: Homo sapiens
```

```
<400> SEQUENCE: 67

Met Ala Leu Ala Ala Leu Met Ile Ala Leu Gly Ser Leu Gly Leu His
1               5                   10                  15

Thr Trp Gln Ala Gln
            20

<210> SEQ ID NO 68
<211> LENGTH: 24
<212> TYPE: PRT
<213> ORGANISM: Homo sapiens

<400> SEQUENCE: 68

Met Ala Gly Ala Val Ser Leu Leu Gly Val Val Gly Leu Leu Leu Val
1               5                   10                  15

Ser Ala Leu Ser Gly Val Leu Gly
            20

<210> SEQ ID NO 69
<211> LENGTH: 21
<212> TYPE: PRT
<213> ORGANISM: Homo sapiens

<400> SEQUENCE: 69

Met Asp Thr Ser Arg Leu Gly Val Leu Leu Ser Leu Pro Val Leu Leu
1               5                   10                  15

Gln Leu Ala Thr Gly
            20

<210> SEQ ID NO 70
<211> LENGTH: 21
<212> TYPE: PRT
<213> ORGANISM: Homo sapiens

<400> SEQUENCE: 70

Met Ser Pro Ser Gly Arg Leu Cys Leu Leu Thr Ile Val Gly Leu Ile
1               5                   10                  15

Leu Pro Thr Arg Gly
            20

<210> SEQ ID NO 71
<211> LENGTH: 21
<212> TYPE: PRT
<213> ORGANISM: Homo sapiens

<400> SEQUENCE: 71

Met Ala Ala Ala Ala Trp Leu Gln Val Leu Pro Val Ile Leu Leu Leu
1               5                   10                  15

Leu Gly Ala His Pro
            20

<210> SEQ ID NO 72
<211> LENGTH: 20
<212> TYPE: PRT
<213> ORGANISM: Homo sapiens

<400> SEQUENCE: 72

Met Arg Arg Leu Leu Leu Val Thr Ser Leu Val Val Val Leu Leu Trp
1               5                   10                  15

Glu Ala Gly Ala
            20
```

```
<210> SEQ ID NO 73
<211> LENGTH: 22
<212> TYPE: PRT
<213> ORGANISM: Homo sapiens

<400> SEQUENCE: 73

Met Ala Pro Ser Ala Trp Ala Ile Cys Trp Leu Leu Gly Gly Leu Leu
1               5                   10                  15

Leu His Gly Gly Ser Ser
            20

<210> SEQ ID NO 74
<211> LENGTH: 25
<212> TYPE: PRT
<213> ORGANISM: Homo sapiens

<400> SEQUENCE: 74

Met Val Thr Arg Ala Gly Ala Gly Thr Ala Val Ala Gly Ala Val Val
1               5                   10                  15

Val Ala Leu Leu Ser Ala Ala Leu Ala
            20                  25

<210> SEQ ID NO 75
<211> LENGTH: 19
<212> TYPE: PRT
<213> ORGANISM: Homo sapiens

<400> SEQUENCE: 75

Met Trp Pro Leu Trp Arg Leu Val Ser Leu Leu Ala Leu Ser Gln Ala
1               5                   10                  15

Leu Pro Phe

<210> SEQ ID NO 76
<211> LENGTH: 16
<212> TYPE: PRT
<213> ORGANISM: Homo sapiens

<400> SEQUENCE: 76

Met Leu Thr Val Ala Leu Leu Ala Leu Leu Cys Ala Ser Ala Ser Gly
1               5                   10                  15

<210> SEQ ID NO 77
<211> LENGTH: 15
<212> TYPE: PRT
<213> ORGANISM: Homo sapiens

<400> SEQUENCE: 77

Met Lys Val Leu Ile Leu Ala Cys Leu Val Ala Leu Ala Leu Ala
1               5                   10                  15

<210> SEQ ID NO 78
<211> LENGTH: 15
<212> TYPE: PRT
<213> ORGANISM: Homo sapiens

<400> SEQUENCE: 78

Met Asn Pro Leu Leu Ile Leu Thr Phe Val Ala Ala Ala Leu Ala
1               5                   10                  15

<210> SEQ ID NO 79
<211> LENGTH: 15
<212> TYPE: PRT
<213> ORGANISM: Homo sapiens
```

<400> SEQUENCE: 79

Met Asn Leu Leu Leu Ile Leu Thr Phe Val Ala Ala Ala Val Ala
1               5                   10                  15

<210> SEQ ID NO 80
<211> LENGTH: 16
<212> TYPE: PRT
<213> ORGANISM: Homo sapiens

<400> SEQUENCE: 80

Met Lys Val Ser Ala Val Leu Cys Leu Leu Met Thr Ala Ala
1               5                   10                  15

<210> SEQ ID NO 81
<211> LENGTH: 17
<212> TYPE: PRT
<213> ORGANISM: Homo sapiens

<400> SEQUENCE: 81

Met Ala Leu Phe Gly Ala Leu Phe Leu Ala Leu Ala Gly Ala His
1               5                   10                  15

Ala

<210> SEQ ID NO 82
<211> LENGTH: 15
<212> TYPE: PRT
<213> ORGANISM: Homo sapiens

<400> SEQUENCE: 82

Met Lys Trp Leu Leu Leu Gly Leu Val Ala Leu Ser Glu Cys
1               5                   10                  15

<210> SEQ ID NO 83
<211> LENGTH: 17
<212> TYPE: PRT
<213> ORGANISM: Homo sapiens

<400> SEQUENCE: 83

Met Leu Leu Ser Val Pro Leu Leu Leu Gly Leu Leu Gly Leu Ala Val
1               5                   10                  15

Ala

<210> SEQ ID NO 84
<211> LENGTH: 18
<212> TYPE: PRT
<213> ORGANISM: Homo sapiens

<400> SEQUENCE: 84

Met Gly Ala Pro Arg Ser Leu Leu Leu Ala Leu Ala Ala Gly Leu Ala
1               5                   10                  15

Val Ala

<210> SEQ ID NO 85
<211> LENGTH: 16
<212> TYPE: PRT
<213> ORGANISM: Homo sapiens

<400> SEQUENCE: 85

Met Ala Leu Arg Val Leu Leu Leu Thr Ala Leu Thr Leu Cys His Gly
1               5                   10                  15

<210> SEQ ID NO 86

<211> LENGTH: 17
<212> TYPE: PRT
<213> ORGANISM: Homo sapiens

<400> SEQUENCE: 86

Met Leu Gln Asn Ser Ala Val Leu Leu Val Leu Val Ile Ser Ala Ser
1               5                   10                  15

Ala

<210> SEQ ID NO 87
<211> LENGTH: 18
<212> TYPE: PRT
<213> ORGANISM: Homo sapiens

<400> SEQUENCE: 87

Met Leu Ala Leu Leu Cys Ser Cys Leu Leu Leu Ala Ala Gly Ala Ser
1               5                   10                  15

Asp Ala

<210> SEQ ID NO 88
<211> LENGTH: 16
<212> TYPE: PRT
<213> ORGANISM: Homo sapiens

<400> SEQUENCE: 88

Met Lys Arg Val Leu Val Leu Leu Leu Ala Val Ala Phe Gly His Ala
1               5                   10                  15

<210> SEQ ID NO 89
<211> LENGTH: 17
<212> TYPE: PRT
<213> ORGANISM: Homo sapiens

<400> SEQUENCE: 89

Met Ile Ser Pro Phe Leu Val Leu Ala Ile Gly Thr Cys Leu Thr Asn
1               5                   10                  15

Ser

<210> SEQ ID NO 90
<211> LENGTH: 16
<212> TYPE: PRT
<213> ORGANISM: Homo sapiens

<400> SEQUENCE: 90

Met Pro Leu Leu Leu Leu Leu Leu Leu Pro Ser Pro Leu His Pro
1               5                   10                  15

<210> SEQ ID NO 91
<211> LENGTH: 17
<212> TYPE: PRT
<213> ORGANISM: Homo sapiens

<400> SEQUENCE: 91

Met Leu Pro Gly Leu Ala Leu Leu Leu Ala Ala Trp Thr Ala Arg
1               5                   10                  15

Ala

<210> SEQ ID NO 92
<211> LENGTH: 18
<212> TYPE: PRT
<213> ORGANISM: Homo sapiens

<400> SEQUENCE: 92

```
Met Ser Leu Ser Ala Phe Thr Leu Phe Leu Ala Leu Ile Gly Gly Thr
1               5                   10                  15

Ser Gly

<210> SEQ ID NO 93
<211> LENGTH: 18
<212> TYPE: PRT
<213> ORGANISM: Homo sapiens

<400> SEQUENCE: 93

Met Leu Cys Leu Leu Leu Thr Leu Gly Val Ala Leu Val Cys Gly Val
1               5                   10                  15

Pro Ala

<210> SEQ ID NO 94
<211> LENGTH: 16
<212> TYPE: PRT
<213> ORGANISM: Homo sapiens

<400> SEQUENCE: 94

Met Phe Arg Leu Trp Leu Leu Leu Ala Gly Leu Cys Gly Leu Leu Ala
1               5                   10                  15

<210> SEQ ID NO 95
<211> LENGTH: 15
<212> TYPE: PRT
<213> ORGANISM: Homo sapiens

<400> SEQUENCE: 95

Met Trp Phe Leu Thr Thr Leu Leu Leu Trp Val Pro Val Asp Gly
1               5                   10                  15

<210> SEQ ID NO 96
<211> LENGTH: 16
<212> TYPE: PRT
<213> ORGANISM: Homo sapiens

<400> SEQUENCE: 96

Met Arg Ser Thr Ile Leu Leu Phe Cys Leu Leu Gly Ser Thr Arg Ser
1               5                   10                  15

<210> SEQ ID NO 97
<211> LENGTH: 17
<212> TYPE: PRT
<213> ORGANISM: Homo sapiens

<400> SEQUENCE: 97

Met Ala Arg Ile Leu Leu Leu Phe Leu Pro Gly Leu Val Ala Val Cys
1               5                   10                  15

Ala

<210> SEQ ID NO 98
<211> LENGTH: 18
<212> TYPE: PRT
<213> ORGANISM: Homo sapiens

<400> SEQUENCE: 98

Met Val Ala Ala Val Leu Leu Gly Leu Ser Trp Leu Cys Ser Pro Leu
1               5                   10                  15

Gly Ala
```

<210> SEQ ID NO 99
<211> LENGTH: 18
<212> TYPE: PRT
<213> ORGANISM: Homo sapiens

<400> SEQUENCE: 99

Met Lys Pro Leu Leu Leu Ala Val Ser Leu Gly Leu Ile Ala Ala Leu
1               5                   10                  15

Gln Ala

<210> SEQ ID NO 100
<211> LENGTH: 17
<212> TYPE: PRT
<213> ORGANISM: Homo sapiens

<400> SEQUENCE: 100

Met Leu Arg Arg Ala Leu Leu Cys Leu Ala Val Ala Ala Leu Val Arg
1               5                   10                  15

Ala

<210> SEQ ID NO 101
<211> LENGTH: 17
<212> TYPE: PRT
<213> ORGANISM: Homo sapiens

<400> SEQUENCE: 101

Met Ala Leu Leu Phe Leu Leu Pro Leu Val Met Gln Gly Val Ser Arg
1               5                   10                  15

Ala

<210> SEQ ID NO 102
<211> LENGTH: 17
<212> TYPE: PRT
<213> ORGANISM: Homo sapiens

<400> SEQUENCE: 102

Met Glu Lys Ile Leu Ile Leu Leu Leu Val Ala Leu Ser Val Ala Tyr
1               5                   10                  15

Ala

<210> SEQ ID NO 103
<211> LENGTH: 16
<212> TYPE: PRT
<213> ORGANISM: Homo sapiens

<400> SEQUENCE: 103

Met Thr Thr Leu Leu Trp Val Phe Val Thr Leu Arg Val Ile Thr Ala
1               5                   10                  15

<210> SEQ ID NO 104
<211> LENGTH: 19
<212> TYPE: PRT
<213> ORGANISM: Homo sapiens

<400> SEQUENCE: 104

Met Gly Ser Gly Leu Pro Leu Val Leu Leu Leu Thr Leu Leu Gly Ser
1               5                   10                  15

Ser His Gly

<210> SEQ ID NO 105
<211> LENGTH: 18
<212> TYPE: PRT

<213> ORGANISM: Homo sapiens

<400> SEQUENCE: 105

Met Gly Thr Gln Glu Gly Trp Cys Leu Leu Cys Leu Ala Leu Ser
1               5                   10                  15
Gly Ala

<210> SEQ ID NO 106
<211> LENGTH: 18
<212> TYPE: PRT
<213> ORGANISM: Homo sapiens

<400> SEQUENCE: 106

Met Lys Leu Leu Thr Gly Leu Val Phe Cys Ser Leu Val Leu Gly Val
1               5                   10                  15
Ser Ser

<210> SEQ ID NO 107
<211> LENGTH: 17
<212> TYPE: PRT
<213> ORGANISM: Homo sapiens

<400> SEQUENCE: 107

Met Ala Val Phe Leu Gln Leu Pro Leu Leu Leu Ser Arg Ala Gln
1               5                   10                  15
Gly

<210> SEQ ID NO 108
<211> LENGTH: 18
<212> TYPE: PRT
<213> ORGANISM: Homo sapiens

<400> SEQUENCE: 108

Met Ser Ala Leu Gly Ala Val Ile Ala Leu Leu Leu Trp Gly Gln Leu
1               5                   10                  15
Phe Ala

<210> SEQ ID NO 109
<211> LENGTH: 16
<212> TYPE: PRT
<213> ORGANISM: Homo sapiens

<400> SEQUENCE: 109

Met Lys Trp Met Val Val Val Leu Val Cys Leu Gln Leu Leu Glu Ala
1               5                   10                  15

<210> SEQ ID NO 110
<211> LENGTH: 18
<212> TYPE: PRT
<213> ORGANISM: Homo sapiens

<400> SEQUENCE: 110

Met Gly Leu Ala Trp Gly Leu Gly Val Leu Phe Leu Met His Val Cys
1               5                   10                  15
Gly Thr

<210> SEQ ID NO 111
<211> LENGTH: 16
<212> TYPE: PRT
<213> ORGANISM: Homo sapiens

<400> SEQUENCE: 111

```
Met Trp Ser Gly Trp Trp Leu Trp Pro Leu Val Ala Val Cys Thr Ala
1               5                   10                  15
```

<210> SEQ ID NO 112
<211> LENGTH: 18
<212> TYPE: PRT
<213> ORGANISM: Homo sapiens

<400> SEQUENCE: 112

```
Met Phe Ala Leu Gly Leu Pro Phe Leu Val Leu Leu Val Ala Ser Val
1               5                   10                  15

Glu Ser
```

<210> SEQ ID NO 113
<211> LENGTH: 18
<212> TYPE: PRT
<213> ORGANISM: Homo sapiens

<400> SEQUENCE: 113

```
Met Lys Val Leu Trp Ala Ala Leu Leu Val Thr Phe Leu Ala Gly Cys
1               5                   10                  15

Gln Ala
```

<210> SEQ ID NO 114
<211> LENGTH: 18
<212> TYPE: PRT
<213> ORGANISM: Homo sapiens

<400> SEQUENCE: 114

```
Met Lys Ala Leu Ile Ala Ala Leu Leu Leu Ile Thr Leu Gln Tyr Ser
1               5                   10                  15

Cys Ala
```

<210> SEQ ID NO 115
<211> LENGTH: 20
<212> TYPE: PRT
<213> ORGANISM: Homo sapiens

<400> SEQUENCE: 115

```
Met Asn Ser Gly Val Cys Leu Cys Val Leu Met Ala Val Leu Ala Ala
1               5                   10                  15

Gly Ala Leu Thr
            20
```

<210> SEQ ID NO 116
<211> LENGTH: 17
<212> TYPE: PRT
<213> ORGANISM: Homo sapiens

<400> SEQUENCE: 116

```
Met Ile Trp Tyr Ile Leu Ile Ile Gly Ile Leu Leu Pro Gln Ser Leu
1               5                   10                  15

Ala
```

<210> SEQ ID NO 117
<211> LENGTH: 19
<212> TYPE: PRT
<213> ORGANISM: Homo sapiens

<400> SEQUENCE: 117

```
Met Trp Arg Ser Leu Gly Leu Ala Leu Ala Leu Cys Leu Leu Pro Ser
```

-continued

```
                1               5                  10                  15

Gly Gly Thr

<210> SEQ ID NO 118
<211> LENGTH: 19
<212> TYPE: PRT
<213> ORGANISM: Homo sapiens

<400> SEQUENCE: 118

Met Pro Ala Leu Gly Trp Ala Val Ala Ala Ile Leu Met Leu Gln Thr
1               5                   10                  15

Ala Met Ala

<210> SEQ ID NO 119
<211> LENGTH: 19
<212> TYPE: PRT
<213> ORGANISM: Homo sapiens

<400> SEQUENCE: 119

Met Arg Thr Leu Ala Ile Leu Ala Ala Ile Leu Leu Val Ala Leu Gln
1               5                   10                  15

Ala Gln Ala

<210> SEQ ID NO 120
<211> LENGTH: 19
<212> TYPE: PRT
<213> ORGANISM: Homo sapiens

<400> SEQUENCE: 120

Met Arg Thr Leu Ala Ile Leu Ala Ala Ile Leu Leu Val Ala Leu Gln
1               5                   10                  15

Ala Gln Ala

<210> SEQ ID NO 121
<211> LENGTH: 20
<212> TYPE: PRT
<213> ORGANISM: Homo sapiens

<400> SEQUENCE: 121

Met Lys Ala Val Leu Leu Ala Leu Leu Met Ala Gly Leu Ala Leu Gln
1               5                   10                  15

Pro Gly Thr Ala
            20

<210> SEQ ID NO 122
<211> LENGTH: 18
<212> TYPE: PRT
<213> ORGANISM: Homo sapiens

<400> SEQUENCE: 122

Met Arg Pro Leu Leu Leu Ala Leu Leu Gly Trp Leu Leu Leu Ala
1               5                   10                  15

Glu Ala

<210> SEQ ID NO 123
<211> LENGTH: 19
<212> TYPE: PRT
<213> ORGANISM: Homo sapiens

<400> SEQUENCE: 123

Met Thr Arg Thr Arg Ala Ala Leu Leu Leu Phe Thr Ala Leu Ala Thr
```

```
                1               5                  10                 15
Ser Leu Gly

<210> SEQ ID NO 124
<211> LENGTH: 19
<212> TYPE: PRT
<213> ORGANISM: Homo sapiens

<400> SEQUENCE: 124

Met Ser Arg Gly Leu Gln Leu Leu Leu Ser Cys Ala Tyr Ser Leu
1               5                  10                 15

Ala Pro Ala

<210> SEQ ID NO 125
<211> LENGTH: 20
<212> TYPE: PRT
<213> ORGANISM: Homo sapiens

<400> SEQUENCE: 125

Met Ala Thr Pro Arg Gly Leu Gly Ala Leu Leu Leu Leu Leu Leu
1               5                  10                 15

Pro Thr Ser Gly
            20

<210> SEQ ID NO 126
<211> LENGTH: 20
<212> TYPE: PRT
<213> ORGANISM: Homo sapiens

<400> SEQUENCE: 126

Met Thr Ser Lys Leu Ala Val Ala Leu Leu Ala Ala Phe Leu Ile Ser
1               5                  10                 15

Ala Ala Leu Cys
            20

<210> SEQ ID NO 127
<211> LENGTH: 19
<212> TYPE: PRT
<213> ORGANISM: Homo sapiens

<400> SEQUENCE: 127

Met Leu Leu Leu Phe Leu Leu Phe Glu Gly Leu Cys Cys Pro Gly Glu
1               5                  10                 15

Asn Thr Ala

<210> SEQ ID NO 128
<211> LENGTH: 20
<212> TYPE: PRT
<213> ORGANISM: Homo sapiens

<400> SEQUENCE: 128

Met Trp Leu Cys Pro Leu Ala Leu Asn Leu Ile Leu Met Ala Ala Ser
1               5                  10                 15

Gly Ala Val Cys
            20

<210> SEQ ID NO 129
<211> LENGTH: 20
<212> TYPE: PRT
<213> ORGANISM: Homo sapiens

<400> SEQUENCE: 129
```

Met Gly Arg Leu Gln Leu Val Val Leu Gly Leu Thr Cys Cys Trp Ala
1               5                   10                  15

Val Ala Ser Ala
            20

<210> SEQ ID NO 130
<211> LENGTH: 21
<212> TYPE: PRT
<213> ORGANISM: Homo sapiens

<400> SEQUENCE: 130

Met Lys Val Ser Val Ala Ala Leu Ser Cys Leu Met Leu Val Ala Val
1               5                   10                  15

Leu Gly Ser Gln Ala
            20

<210> SEQ ID NO 131
<211> LENGTH: 18
<212> TYPE: PRT
<213> ORGANISM: Homo sapiens

<400> SEQUENCE: 131

Met Arg Leu Leu Pro Arg Leu Leu Leu Leu Leu Leu Leu Val Phe Pro
1               5                   10                  15

Ala Thr

<210> SEQ ID NO 132
<211> LENGTH: 18
<212> TYPE: PRT
<213> ORGANISM: Homo sapiens

<400> SEQUENCE: 132

Met Ile Phe Leu Tyr Gln Val Val His Phe Ile Leu Phe Thr Ser Val
1               5                   10                  15

Ser Gly

<210> SEQ ID NO 133
<211> LENGTH: 20
<212> TYPE: PRT
<213> ORGANISM: Homo sapiens

<400> SEQUENCE: 133

Met Thr Ile Leu Gly Thr Thr Phe Gly Met Val Phe Ser Leu Leu Gln
1               5                   10                  15

Val Val Ser Gly
            20

<210> SEQ ID NO 134
<211> LENGTH: 19
<212> TYPE: PRT
<213> ORGANISM: Homo sapiens

<400> SEQUENCE: 134

Met Lys Phe Leu Val Phe Ala Phe Ile Leu Ala Leu Met Val Ser Met
1               5                   10                  15

Ile Gly Ala

<210> SEQ ID NO 135
<211> LENGTH: 19
<212> TYPE: PRT
<213> ORGANISM: Homo sapiens

<400> SEQUENCE: 135

Met Lys Phe Phe Val Phe Ala Leu Ile Leu Ala Leu Met Leu Ser Met
1               5                   10                  15

Thr Gly Ala

<210> SEQ ID NO 136
<211> LENGTH: 19
<212> TYPE: PRT
<213> ORGANISM: Homo sapiens

<400> SEQUENCE: 136

Met Lys Phe Phe Val Phe Ala Leu Val Leu Ala Leu Met Ile Ser Met
1               5                   10                  15

Ile Ser Ala

<210> SEQ ID NO 137
<211> LENGTH: 21
<212> TYPE: PRT
<213> ORGANISM: Homo sapiens

<400> SEQUENCE: 137

Met Lys Phe Gln Gly Pro Leu Ala Cys Leu Leu Leu Ala Leu Cys Leu
1               5                   10                  15

Gly Ser Gly Glu Ala
            20

<210> SEQ ID NO 138
<211> LENGTH: 19
<212> TYPE: PRT
<213> ORGANISM: Homo sapiens

<400> SEQUENCE: 138

Met Ala Arg Pro His Pro Trp Trp Leu Cys Val Leu Gly Thr Leu Val
1               5                   10                  15

Gly Leu Ser

<210> SEQ ID NO 139
<211> LENGTH: 21
<212> TYPE: PRT
<213> ORGANISM: Homo sapiens

<400> SEQUENCE: 139

Met Ser Ala Val Leu Leu Leu Ala Leu Leu Gly Phe Ile Leu Pro Leu
1               5                   10                  15

Pro Gly Val Gln Ala
            20

<210> SEQ ID NO 140
<211> LENGTH: 22
<212> TYPE: PRT
<213> ORGANISM: Homo sapiens

<400> SEQUENCE: 140

Met Ala Arg Gly Ala Ala Leu Ala Leu Leu Leu Phe Gly Leu Leu Gly
1               5                   10                  15

Val Leu Val Ala Ala Pro
            20

<210> SEQ ID NO 141
<211> LENGTH: 19

```
<212> TYPE: PRT
<213> ORGANISM: Homo sapiens

<400> SEQUENCE: 141

Met Lys Ile Leu Ile Leu Gly Ile Phe Leu Phe Leu Cys Ser Thr Pro
1               5                   10                  15

Ala Trp Ala

<210> SEQ ID NO 142
<211> LENGTH: 20
<212> TYPE: PRT
<213> ORGANISM: Homo sapiens

<400> SEQUENCE: 142

Met Asp Cys Gln Leu Ser Ile Leu Leu Leu Ser Cys Ser Val Leu
1               5                   10                  15

Asp Ser Phe Gly
            20

<210> SEQ ID NO 143
<211> LENGTH: 20
<212> TYPE: PRT
<213> ORGANISM: Homo sapiens

<400> SEQUENCE: 143

Met Arg Ala Leu Leu Ala Arg Leu Leu Leu Cys Val Leu Val Val Ser
1               5                   10                  15

Asp Ser Lys Gly
            20

<210> SEQ ID NO 144
<211> LENGTH: 20
<212> TYPE: PRT
<213> ORGANISM: Homo sapiens

<400> SEQUENCE: 144

Met Ala Trp Thr Pro Leu Phe Leu Phe Leu Leu Thr Cys Cys Pro Gly
1               5                   10                  15

Gly Ser Asn Ser
            20

<210> SEQ ID NO 145
<211> LENGTH: 21
<212> TYPE: PRT
<213> ORGANISM: Homo sapiens

<400> SEQUENCE: 145

Met Arg Leu Leu Leu Ala Leu Leu Gly Val Leu Leu Ser Val Pro Gly
1               5                   10                  15

Pro Pro Val Leu Ser
            20

<210> SEQ ID NO 146
<211> LENGTH: 21
<212> TYPE: PRT
<213> ORGANISM: Homo sapiens

<400> SEQUENCE: 146

Met Ser Gly Ala Arg Ser Lys Leu Ala Leu Phe Leu Cys Gly Cys Tyr
1               5                   10                  15

Val Val Ala Leu Gly
            20
```

<210> SEQ ID NO 147
<211> LENGTH: 20
<212> TYPE: PRT
<213> ORGANISM: Homo sapiens

<400> SEQUENCE: 147

Met Glu Pro Trp Pro Leu Leu Leu Phe Ser Leu Cys Ser Ala Gly
1               5                   10                  15

Leu Val Leu Gly
            20

<210> SEQ ID NO 148
<211> LENGTH: 19
<212> TYPE: PRT
<213> ORGANISM: Homo sapiens

<400> SEQUENCE: 148

Met Ser Arg Leu Pro Val Leu Leu Leu Gln Leu Leu Val Arg Pro
1               5                   10                  15

Gly Leu Gln

<210> SEQ ID NO 149
<211> LENGTH: 19
<212> TYPE: PRT
<213> ORGANISM: Homo sapiens

<400> SEQUENCE: 149

Met Asp Trp Thr Trp Arg Val Phe Cys Leu Leu Ala Val Ala Pro Gly
1               5                   10                  15

Ala His Ser

<210> SEQ ID NO 150
<211> LENGTH: 20
<212> TYPE: PRT
<213> ORGANISM: Homo sapiens

<400> SEQUENCE: 150

Met Glu Met Leu Gln Gly Leu Leu Leu Leu Leu Leu Ser Met Gly
1               5                   10                  15

Gly Ala Trp Ala
            20

<210> SEQ ID NO 151
<211> LENGTH: 20
<212> TYPE: PRT
<213> ORGANISM: Homo sapiens

<400> SEQUENCE: 151

Met Lys Ser Phe Leu Leu Val Val Asn Ala Leu Ala Leu Thr Leu Pro
1               5                   10                  15

Phe Leu Ala Val
            20

<210> SEQ ID NO 152
<211> LENGTH: 20
<212> TYPE: PRT
<213> ORGANISM: Homo sapiens

<400> SEQUENCE: 152

Met Lys Leu Met Val Leu Val Phe Thr Ile Gly Leu Thr Leu Leu Leu
1               5                   10                  15

Gly Val Gln Ala
        20

<210> SEQ ID NO 153
<211> LENGTH: 21
<212> TYPE: PRT
<213> ORGANISM: Homo sapiens

<400> SEQUENCE: 153

Met Leu Pro Cys Leu Val Val Leu Leu Ala Ala Leu Leu Ser Leu Arg
1               5                   10                  15

Leu Gly Ser Asp Ala
        20

<210> SEQ ID NO 154
<211> LENGTH: 22
<212> TYPE: PRT
<213> ORGANISM: Homo sapiens

<400> SEQUENCE: 154

Met Ala Arg Gly Ser Ala Val Ala Trp Ala Leu Gly Pro Leu Leu
1               5                   10                  15

Trp Gly Cys Ala Leu Gly
        20

<210> SEQ ID NO 155
<211> LENGTH: 23
<212> TYPE: PRT
<213> ORGANISM: Homo sapiens

<400> SEQUENCE: 155

Met Ile Leu Asn Lys Ala Leu Leu Leu Gly Ala Leu Ala Leu Thr Ala
1               5                   10                  15

Val Met Ser Pro Cys Gly Gly
        20

<210> SEQ ID NO 156
<211> LENGTH: 21
<212> TYPE: PRT
<213> ORGANISM: Homo sapiens

<400> SEQUENCE: 156

Met Trp Arg Cys Pro Leu Gly Leu Leu Leu Leu Pro Leu Ala Gly
1               5                   10                  15

His Leu Ala Leu Gly
        20

<210> SEQ ID NO 157
<211> LENGTH: 21
<212> TYPE: PRT
<213> ORGANISM: Homo sapiens

<400> SEQUENCE: 157

Met Val Asp Gly Thr Leu Leu Leu Leu Leu Ser Glu Ala Leu Ala Leu
1               5                   10                  15

Thr Gln Thr Trp Ala
        20

<210> SEQ ID NO 158
<211> LENGTH: 20
<212> TYPE: PRT
<213> ORGANISM: Homo sapiens

```
<400> SEQUENCE: 158

Met Arg Pro Ala Asp Leu Leu Gln Leu Val Leu Leu Leu Asp Leu Pro
1               5                   10                  15

Arg Asp Leu Gly
            20

<210> SEQ ID NO 159
<211> LENGTH: 23
<212> TYPE: PRT
<213> ORGANISM: Homo sapiens

<400> SEQUENCE: 159

Met Lys Ala Ser Ala Ala Leu Leu Cys Leu Leu Leu Thr Ala Ala Ala
1               5                   10                  15

Phe Ser Pro Gln Gly Leu Ala
            20

<210> SEQ ID NO 160
<211> LENGTH: 21
<212> TYPE: PRT
<213> ORGANISM: Homo sapiens

<400> SEQUENCE: 160

Met Arg Leu Leu Ile Leu Ala Leu Leu Gly Ile Cys Ser Leu Thr Ala
1               5                   10                  15

Tyr Ile Val Glu Gly
            20

<210> SEQ ID NO 161
<211> LENGTH: 21
<212> TYPE: PRT
<213> ORGANISM: Homo sapiens

<400> SEQUENCE: 161

Met Lys Val Val Pro Ser Leu Leu Leu Ser Val Leu Leu Ala Gln Val
1               5                   10                  15

Trp Leu Val Pro Gly
            20

<210> SEQ ID NO 162
<211> LENGTH: 19
<212> TYPE: PRT
<213> ORGANISM: Homo sapiens

<400> SEQUENCE: 162

Met Arg Leu Leu Trp Gly Leu Ile Trp Ala Ser Ser Phe Phe Thr Leu
1               5                   10                  15

Ser Leu Gln

<210> SEQ ID NO 163
<211> LENGTH: 19
<212> TYPE: PRT
<213> ORGANISM: Homo sapiens

<400> SEQUENCE: 163

Met Arg Leu Leu Trp Gly Leu Ile Trp Ala Ser Ser Phe Phe Thr Leu
1               5                   10                  15

Ser Leu Gln

<210> SEQ ID NO 164
```

<211> LENGTH: 23
<212> TYPE: PRT
<213> ORGANISM: Homo sapiens

<400> SEQUENCE: 164

Met Met Gly Leu Ser Leu Ala Ser Ala Val Leu Leu Ala Ser Leu Leu
1               5                   10                  15

Ser Leu His Leu Gly Thr Ala
            20

<210> SEQ ID NO 165
<211> LENGTH: 21
<212> TYPE: PRT
<213> ORGANISM: Homo sapiens

<400> SEQUENCE: 165

Met Ser Leu Leu Val Val Ser Met Ala Cys Val Gly Phe Phe Leu Leu
1               5                   10                  15

Gln Gly Ala Trp Pro
            20

<210> SEQ ID NO 166
<211> LENGTH: 20
<212> TYPE: PRT
<213> ORGANISM: Homo sapiens

<400> SEQUENCE: 166

Met Ser Asp Leu Leu Ser Val Phe Leu His Leu Leu Leu Phe Lys
1               5                   10                  15

Leu Val Ala Pro
            20

<210> SEQ ID NO 167
<211> LENGTH: 23
<212> TYPE: PRT
<213> ORGANISM: Homo sapiens

<400> SEQUENCE: 167

Met Ala Glu Leu Pro Gly Pro Phe Leu Cys Gly Ala Leu Leu Gly Phe
1               5                   10                  15

Leu Cys Leu Ser Gly Leu Ala
            20

<210> SEQ ID NO 168
<211> LENGTH: 20
<212> TYPE: PRT
<213> ORGANISM: Homo sapiens

<400> SEQUENCE: 168

Met Gly Leu Phe Met Ile Ile Ala Ile Leu Leu Phe Gln Lys Pro Thr
1               5                   10                  15

Val Thr Glu Gln
            20

<210> SEQ ID NO 169
<211> LENGTH: 20
<212> TYPE: PRT
<213> ORGANISM: Homo sapiens

<400> SEQUENCE: 169

Met Val Tyr Lys Thr Leu Phe Ala Leu Cys Ile Leu Thr Ala Gly Trp
1               5                   10                  15

Arg Val Gln Ser
        20

<210> SEQ ID NO 170
<211> LENGTH: 19
<212> TYPE: PRT
<213> ORGANISM: Homo sapiens

<400> SEQUENCE: 170

Met Gln Ile Glu Leu Ser Thr Cys Phe Phe Leu Cys Leu Leu Arg Phe
1               5                   10                  15

Cys Phe Ser

<210> SEQ ID NO 171
<211> LENGTH: 21
<212> TYPE: PRT
<213> ORGANISM: Homo sapiens

<400> SEQUENCE: 171

Met Val Pro Pro Lys Leu His Val Leu Phe Cys Leu Cys Gly Cys Leu
1               5                   10                  15

Ala Val Val Tyr Pro
        20

<210> SEQ ID NO 172
<211> LENGTH: 22
<212> TYPE: PRT
<213> ORGANISM: Homo sapiens

<400> SEQUENCE: 172

Met Ala Ser Arg Leu Thr Leu Leu Thr Leu Leu Leu Leu Leu Leu Ala
1               5                   10                  15

Gly Asp Arg Ala Ser Ser
        20

<210> SEQ ID NO 173
<211> LENGTH: 21
<212> TYPE: PRT
<213> ORGANISM: Homo sapiens

<400> SEQUENCE: 173

Met Gln Arg Leu Cys Val Tyr Val Leu Ile Phe Ala Leu Ala Leu Ala
1               5                   10                  15

Ala Phe Ser Glu Ala
        20

<210> SEQ ID NO 174
<211> LENGTH: 21
<212> TYPE: PRT
<213> ORGANISM: Homo sapiens

<400> SEQUENCE: 174

Met Lys Val Leu Ile Ser Ser Leu Leu Leu Leu Leu Pro Leu Met Leu
1               5                   10                  15

Met Ser Met Val Ser
        20

<210> SEQ ID NO 175
<211> LENGTH: 22
<212> TYPE: PRT
<213> ORGANISM: Homo sapiens

<400> SEQUENCE: 175

Met Glu Pro Gly Pro Ala Leu Ala Trp Leu Leu Leu Ser Leu Leu
1               5                   10                  15

Ala Asp Cys Leu Lys Ala
            20

<210> SEQ ID NO 176
<211> LENGTH: 21
<212> TYPE: PRT
<213> ORGANISM: Homo sapiens

<400> SEQUENCE: 176

Met Leu Leu Ala Trp Val Gln Ala Phe Leu Val Ser Asn Met Leu Leu
1               5                   10                  15

Ala Glu Ala Tyr Gly
            20

<210> SEQ ID NO 177
<211> LENGTH: 21
<212> TYPE: PRT
<213> ORGANISM: Homo sapiens

<400> SEQUENCE: 177

Met Arg Leu Ser Val Cys Leu Leu Leu Thr Leu Ala Leu Cys Cys
1               5                   10                  15

Tyr Arg Ala Asn Ala
            20

<210> SEQ ID NO 178
<211> LENGTH: 22
<212> TYPE: PRT
<213> ORGANISM: Homo sapiens

<400> SEQUENCE: 178

Met Thr Ser Ser Arg Leu Trp Phe Ser Leu Leu Leu Ala Ala Ala Phe
1               5                   10                  15

Ala Gly Arg Ala Thr Ala
            20

<210> SEQ ID NO 179
<211> LENGTH: 20
<212> TYPE: PRT
<213> ORGANISM: Homo sapiens

<400> SEQUENCE: 179

Met Glu Ala Pro Ala Gln Leu Leu Phe Leu Leu Leu Leu Trp Leu Pro
1               5                   10                  15

Asp Thr Thr Arg
            20

<210> SEQ ID NO 180
<211> LENGTH: 21
<212> TYPE: PRT
<213> ORGANISM: Homo sapiens

<400> SEQUENCE: 180

Met Lys Trp Lys Ala Leu Phe Thr Ala Ala Ile Leu Gln Ala Gln Leu
1               5                   10                  15

Pro Ile Thr Glu Ala
            20

<210> SEQ ID NO 181

```
<211> LENGTH: 21
<212> TYPE: PRT
<213> ORGANISM: Homo sapiens

<400> SEQUENCE: 181

Met Glu Ile Lys His Leu Leu Phe Leu Val Ala Ala Ala Cys Leu Leu
1               5                   10                  15

Pro Met Leu Ser Met
            20

<210> SEQ ID NO 182
<211> LENGTH: 22
<212> TYPE: PRT
<213> ORGANISM: Homo sapiens

<400> SEQUENCE: 182

Met Glu Gly Pro Arg Gly Trp Leu Val Leu Cys Val Leu Ala Ile Ser
1               5                   10                  15

Leu Ala Ser Met Val Thr
            20

<210> SEQ ID NO 183
<211> LENGTH: 22
<212> TYPE: PRT
<213> ORGANISM: Homo sapiens

<400> SEQUENCE: 183

Met Ala Leu Gly Val Pro Ile Ser Val Tyr Leu Leu Phe Asn Ala Met
1               5                   10                  15

Thr Ala Leu Thr Glu Glu
            20

<210> SEQ ID NO 184
<211> LENGTH: 23
<212> TYPE: PRT
<213> ORGANISM: Homo sapiens

<400> SEQUENCE: 184

Met Lys Val Ser Ala Ala Leu Leu Trp Leu Leu Leu Ile Ala Ala Ala
1               5                   10                  15

Phe Ser Pro Gln Gly Leu Ala
            20

<210> SEQ ID NO 185
<211> LENGTH: 22
<212> TYPE: PRT
<213> ORGANISM: Homo sapiens

<400> SEQUENCE: 185

Met Leu Lys Pro Ser Leu Pro Phe Thr Ser Leu Leu Phe Leu Gln Leu
1               5                   10                  15

Pro Leu Leu Gly Val Gly
            20

<210> SEQ ID NO 186
<211> LENGTH: 21
<212> TYPE: PRT
<213> ORGANISM: Homo sapiens

<400> SEQUENCE: 186

Met Trp Val Ser Trp Ala Pro Gly Leu Trp Leu Leu Gly Leu Trp Ala
1               5                   10                  15
```

Thr Phe Gly His Gly
            20

<210> SEQ ID NO 187
<211> LENGTH: 23
<212> TYPE: PRT
<213> ORGANISM: Homo sapiens

<400> SEQUENCE: 187

Met Gln Val Ser Thr Ala Ala Leu Ala Val Leu Leu Cys Thr Met Ala
1               5                   10                  15

Leu Cys Asn Gln Phe Ser Ala
            20

<210> SEQ ID NO 188
<211> LENGTH: 22
<212> TYPE: PRT
<213> ORGANISM: Homo sapiens

<400> SEQUENCE: 188

Met Ala Lys Val Phe Ser Phe Ile Leu Val Thr Thr Ala Leu Thr Met
1               5                   10                  15

Gly Arg Glu Ile Ser Ala
            20

<210> SEQ ID NO 189
<211> LENGTH: 22
<212> TYPE: PRT
<213> ORGANISM: Homo sapiens

<400> SEQUENCE: 189

Met Gly Thr Arg Leu Leu Pro Ala Leu Phe Leu Val Leu Leu Val Leu
1               5                   10                  15

Gly Phe Glu Val Gln Gly
            20

<210> SEQ ID NO 190
<211> LENGTH: 21
<212> TYPE: PRT
<213> ORGANISM: Homo sapiens

<400> SEQUENCE: 190

Met Ala Gln His His Leu Trp Ile Leu Leu Cys Leu Gln Thr Trp
1               5                   10                  15

Pro Glu Ala Ala Gly
            20

<210> SEQ ID NO 191
<211> LENGTH: 24
<212> TYPE: PRT
<213> ORGANISM: Homo sapiens

<400> SEQUENCE: 191

Met Ser Arg Thr Ala Tyr Thr Val Gly Ala Leu Leu Leu Leu Leu Gly
1               5                   10                  15

Thr Leu Leu Pro Ala Ala Glu Gly
            20

<210> SEQ ID NO 192
<211> LENGTH: 23
<212> TYPE: PRT
<213> ORGANISM: Homo sapiens

```
<400> SEQUENCE: 192

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 193
<211> LENGTH: 23
<212> TYPE: PRT
<213> ORGANISM: Homo sapiens

<400> SEQUENCE: 193

Met Pro Ser Pro Gly Thr Val Cys Ser Leu Leu Leu Gly Met Leu
1               5                   10                  15

Trp Leu Asp Leu Ala Met Ala
            20

<210> SEQ ID NO 194
<211> LENGTH: 22
<212> TYPE: PRT
<213> ORGANISM: Homo sapiens

<400> SEQUENCE: 194

Met Asp Met Arg Val Leu Ala Gln Leu Leu Gly Leu Leu Leu Leu Cys
1               5                   10                  15

Phe Pro Gly Ala Arg Cys
            20

<210> SEQ ID NO 195
<211> LENGTH: 22
<212> TYPE: PRT
<213> ORGANISM: Homo sapiens

<400> SEQUENCE: 195

Met Ala Gln Thr Ser Ser Tyr Phe Met Leu Ile Ser Cys Leu Met Phe
1               5                   10                  15

Leu Ser Gln Ser Gln Gly
            20

<210> SEQ ID NO 196
<211> LENGTH: 25
<212> TYPE: PRT
<213> ORGANISM: Homo sapiens

<400> SEQUENCE: 196

Met Ala Gln His Gly Ala Met Gly Ala Phe Arg Ala Leu Cys Gly Leu
1               5                   10                  15

Ala Leu Leu Cys Ala Leu Ser Leu Gly
            20                  25

<210> SEQ ID NO 197
<211> LENGTH: 22
<212> TYPE: PRT
<213> ORGANISM: Homo sapiens

<400> SEQUENCE: 197

Met Ala Met Thr Trp Ile Val Phe Ser Leu Trp Pro Leu Thr Val Phe
1               5                   10                  15

Met Gly His Ile Gly Gly
            20
```

```
<210> SEQ ID NO 198
<211> LENGTH: 26
<212> TYPE: PRT
<213> ORGANISM: Homo sapiens

<400> SEQUENCE: 198

Met Gly Leu Gly Ala Arg Gly Ala Trp Ala Ala Leu Leu Leu Gly Thr
1               5                   10                  15

Leu Gln Val Leu Ala Leu Leu Gly Ala Ala
            20                  25

<210> SEQ ID NO 199
<211> LENGTH: 24
<212> TYPE: PRT
<213> ORGANISM: Homo sapiens

<400> SEQUENCE: 199

Met Ala Arg Leu Gln Thr Ala Leu Leu Val Leu Val Leu Leu Leu Ala
1               5                   10                  15

Val Ala Leu Gln Ala Thr Glu Ala
            20

<210> SEQ ID NO 200
<211> LENGTH: 25
<212> TYPE: PRT
<213> ORGANISM: Homo sapiens

<400> SEQUENCE: 200

Met Ala Gly Pro Pro Arg Leu Leu Leu Pro Leu Leu Leu Ala Leu Leu
1               5                   10                  15

Ala Arg Gly Leu Pro Gly Ala Leu Ala
            20                  25

<210> SEQ ID NO 201
<211> LENGTH: 22
<212> TYPE: PRT
<213> ORGANISM: Homo sapiens

<400> SEQUENCE: 201

Met Leu Thr Leu Gln Thr Trp Leu Val Gln Ala Leu Phe Ile Phe Leu
1               5                   10                  15

Thr Thr Glu Ser Thr Gly
            20

<210> SEQ ID NO 202
<211> LENGTH: 24
<212> TYPE: PRT
<213> ORGANISM: Homo sapiens

<400> SEQUENCE: 202

Met Glu Arg Gly Ala Gly Ala Lys Leu Leu Pro Leu Leu Leu Leu Leu
1               5                   10                  15

Arg Ala Thr Gly Phe Thr Cys Ala
            20

<210> SEQ ID NO 203
<211> LENGTH: 23
<212> TYPE: PRT
<213> ORGANISM: Homo sapiens

<400> SEQUENCE: 203

Met Lys Ser Ile Ile Leu Phe Val Leu Ser Leu Leu Ile Leu Glu
1               5                   10                  15
```

```
Lys Gln Ala Ala Val Met Gly
            20

<210> SEQ ID NO 204
<211> LENGTH: 24
<212> TYPE: PRT
<213> ORGANISM: Homo sapiens

<400> SEQUENCE: 204

Met Ala Val Met Ala Pro Arg Thr Leu Leu Leu Leu Leu Gly Ala
1               5                   10                  15

Leu Ala Leu Thr Gln Thr Arg Ala
            20

<210> SEQ ID NO 205
<211> LENGTH: 23
<212> TYPE: PRT
<213> ORGANISM: Homo sapiens

<400> SEQUENCE: 205

Met Lys Leu Ser Gly Met Phe Leu Leu Ser Leu Ala Leu Phe Cys
1               5                   10                  15

Phe Leu Thr Gly Val Phe Ser
            20

<210> SEQ ID NO 206
<211> LENGTH: 22
<212> TYPE: PRT
<213> ORGANISM: Homo sapiens

<400> SEQUENCE: 206

Met Val Met Arg Pro Leu Trp Ser Leu Leu Trp Glu Ala Leu Leu
1               5                   10                  15

Pro Ile Thr Val Thr Gly
            20

<210> SEQ ID NO 207
<211> LENGTH: 24
<212> TYPE: PRT
<213> ORGANISM: Homo sapiens

<400> SEQUENCE: 207

Met Ala Ile Met Ala Pro Arg Thr Leu Val Leu Leu Leu Ser Gly Ala
1               5                   10                  15

Leu Ala Leu Thr Gln Thr Trp Ala
            20

<210> SEQ ID NO 208
<211> LENGTH: 24
<212> TYPE: PRT
<213> ORGANISM: Homo sapiens

<400> SEQUENCE: 208

Met Ala Val Met Ala Pro Arg Thr Leu Leu Leu Leu Leu Ser Gly Ala
1               5                   10                  15

Leu Ala Leu Thr Gln Thr Trp Ala
            20

<210> SEQ ID NO 209
<211> LENGTH: 24
<212> TYPE: PRT
<213> ORGANISM: Homo sapiens
```

<400> SEQUENCE: 209

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 210
<211> LENGTH: 24
<212> TYPE: PRT
<213> ORGANISM: Homo sapiens

<400> SEQUENCE: 210

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 211
<211> LENGTH: 24
<212> TYPE: PRT
<213> ORGANISM: Homo sapiens

<400> SEQUENCE: 211

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 212
<211> LENGTH: 24
<212> TYPE: PRT
<213> ORGANISM: Homo sapiens

<400> SEQUENCE: 212

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 213
<211> LENGTH: 23
<212> TYPE: PRT
<213> ORGANISM: Homo sapiens

<400> SEQUENCE: 213

Met Lys Pro Asn Ile Ile Phe Val Leu Ser Leu Leu Leu Ile Leu Glu
1               5                   10                  15

Lys Gln Ala Ala Val Met Gly
            20

<210> SEQ ID NO 214
<211> LENGTH: 25
<212> TYPE: PRT
<213> ORGANISM: Homo sapiens

<400> SEQUENCE: 214

Met Gly Ile Gln Gly Gly Ser Val Leu Phe Gly Leu Leu Leu Val Leu
1               5                   10                  15

Ala Val Phe Cys His Ser Gly His Ser
            20                  25

<210> SEQ ID NO 215
<211> LENGTH: 23
<212> TYPE: PRT
<213> ORGANISM: Homo sapiens

<400> SEQUENCE: 215

Met Ser Ala Phe Arg Leu Trp Pro Gly Leu Leu Ile Met Leu Gly Ser
1               5                   10                  15

Leu Cys His Arg Gly Ser Pro
            20

<210> SEQ ID NO 216
<211> LENGTH: 22
<212> TYPE: PRT
<213> ORGANISM: Homo sapiens

<400> SEQUENCE: 216

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 217
<211> LENGTH: 24
<212> TYPE: PRT
<213> ORGANISM: Homo sapiens

<400> SEQUENCE: 217

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 218
<211> LENGTH: 22
<212> TYPE: PRT
<213> ORGANISM: Homo sapiens

<400> SEQUENCE: 218

Met Arg Ile His Tyr Leu Leu Phe Ala Leu Leu Phe Leu Phe Leu Val
1               5                   10                  15

Pro Val Pro Gly His Gly
            20

<210> SEQ ID NO 219
<211> LENGTH: 25
<212> TYPE: PRT
<213> ORGANISM: Homo sapiens

<400> SEQUENCE: 219

Met Gln Thr Pro Arg Ala Ser Pro Pro Arg Pro Ala Leu Leu Leu Leu
1               5                   10                  15

Leu Leu Leu Leu Gly Gly Ala His Gly
            20                  25

<210> SEQ ID NO 220
<211> LENGTH: 25
<212> TYPE: PRT
<213> ORGANISM: Homo sapiens

<400> SEQUENCE: 220

Met Gly Ser Arg Ala Glu Leu Cys Thr Leu Leu Gly Gly Phe Ser Phe

```
                1               5                  10                 15
Leu Leu Leu Leu Ile Pro Gly Glu Gly
            20                  25

<210> SEQ ID NO 221
<211> LENGTH: 22
<212> TYPE: PRT
<213> ORGANISM: Homo sapiens

<400> SEQUENCE: 221

Met Glu Lys Lys Cys Thr Leu Tyr Phe Leu Val Leu Leu Pro Phe Phe
1               5                  10                 15

Met Ile Leu Val Thr Ala
            20

<210> SEQ ID NO 222
<211> LENGTH: 27
<212> TYPE: PRT
<213> ORGANISM: Homo sapiens

<400> SEQUENCE: 222

Met Ala Pro Ser Ser Pro Arg Pro Ala Leu Pro Ala Leu Leu Val Leu
1               5                  10                 15

Leu Gly Ala Leu Phe Pro Gly Pro Gly Asn Ala
            20                  25

<210> SEQ ID NO 223
<211> LENGTH: 23
<212> TYPE: PRT
<213> ORGANISM: Homo sapiens

<400> SEQUENCE: 223

Met Arg Gln Ser His Gln Leu Pro Leu Val Gly Leu Leu Leu Phe Ser
1               5                  10                 15

Phe Ile Pro Ser Gln Leu Cys
            20

<210> SEQ ID NO 224
<211> LENGTH: 24
<212> TYPE: PRT
<213> ORGANISM: Homo sapiens

<400> SEQUENCE: 224

Met Arg Val Met Ala Pro Arg Thr Leu Ile Leu Leu Leu Ser Gly Ala
1               5                  10                 15

Leu Ala Leu Thr Glu Thr Trp Ala
            20

<210> SEQ ID NO 225
<211> LENGTH: 24
<212> TYPE: PRT
<213> ORGANISM: Homo sapiens

<400> SEQUENCE: 225

Met Arg Val Met Ala Pro Arg Thr Leu Ile Leu Leu Leu Ser Gly Ala
1               5                  10                 15

Leu Ala Leu Thr Glu Thr Trp Ala
            20

<210> SEQ ID NO 226
<211> LENGTH: 24
<212> TYPE: PRT
```

-continued

```
<213> ORGANISM: Homo sapiens

<400> SEQUENCE: 226

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 227
<211> LENGTH: 24
<212> TYPE: PRT
<213> ORGANISM: Homo sapiens

<400> SEQUENCE: 227

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 228
<211> LENGTH: 24
<212> TYPE: PRT
<213> ORGANISM: Homo sapiens

<400> SEQUENCE: 228

Met Arg Val Met Ala Pro Arg Thr Leu Leu Leu Leu Leu Ser Gly Ala
1               5                   10                  15

Leu Ala Leu Thr Glu Thr Trp Ala
            20

<210> SEQ ID NO 229
<211> LENGTH: 24
<212> TYPE: PRT
<213> ORGANISM: Homo sapiens

<400> SEQUENCE: 229

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 230
<211> LENGTH: 24
<212> TYPE: PRT
<213> ORGANISM: Homo sapiens

<400> SEQUENCE: 230

Met Arg Val Met Ala Pro Arg Thr Leu Ile Leu Leu Leu Ser Gly Ala
1               5                   10                  15

Leu Ala Leu Thr Glu Thr Trp Ala
            20

<210> SEQ ID NO 231
<211> LENGTH: 24
<212> TYPE: PRT
<213> ORGANISM: Homo sapiens

<400> SEQUENCE: 231

Met Arg Val Met Ala Pro Arg Thr Leu Ile Leu Leu Leu Ser Gly Ala
1               5                   10                  15

Leu Ala Leu Thr Glu Thr Trp Ala
            20
```

<210> SEQ ID NO 232
<211> LENGTH: 24
<212> TYPE: PRT
<213> ORGANISM: Homo sapiens

<400> SEQUENCE: 232

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 233
<211> LENGTH: 26
<212> TYPE: PRT
<213> ORGANISM: Homo sapiens

<400> SEQUENCE: 233

Met Ala Ala Val Val Ala Ala Thr Arg Trp Trp Gln Leu Leu Leu Val
1               5                   10                  15

Leu Ser Ala Ala Gly Met Gly Ala Ser Gly
            20                  25

<210> SEQ ID NO 234
<211> LENGTH: 25
<212> TYPE: PRT
<213> ORGANISM: Homo sapiens

<400> SEQUENCE: 234

Met Ala Gly Pro Ala Ile His Thr Ala Pro Met Leu Phe Leu Val Leu
1               5                   10                  15

Leu Leu Pro Leu Glu Leu Ser Leu Ala
            20                  25

<210> SEQ ID NO 235
<211> LENGTH: 25
<212> TYPE: PRT
<213> ORGANISM: Homo sapiens

<400> SEQUENCE: 235

Met Lys Asp Ser Cys Ile Thr Val Met Ala Met Ala Leu Leu Ser Gly
1               5                   10                  15

Phe Phe Phe Phe Ala Pro Ala Ser Ser
            20                  25

<210> SEQ ID NO 236
<211> LENGTH: 24
<212> TYPE: PRT
<213> ORGANISM: Homo sapiens

<400> SEQUENCE: 236

Met Arg Val Thr Ala Pro Arg Thr Leu Leu Leu Leu Leu Trp Gly Ala
1               5                   10                  15

Leu Ala Leu Thr Glu Thr Trp Ala
            20

<210> SEQ ID NO 237
<211> LENGTH: 24
<212> TYPE: PRT
<213> ORGANISM: Homo sapiens

<400> SEQUENCE: 237

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 238
<211> LENGTH: 24
<212> TYPE: PRT
<213> ORGANISM: Homo sapiens

<400> SEQUENCE: 238

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 239
<211> LENGTH: 24
<212> TYPE: PRT
<213> ORGANISM: Homo sapiens

<400> SEQUENCE: 239

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 240
<211> LENGTH: 24
<212> TYPE: PRT
<213> ORGANISM: Homo sapiens

<400> SEQUENCE: 240

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 241
<211> LENGTH: 26
<212> TYPE: PRT
<213> ORGANISM: Homo sapiens

<400> SEQUENCE: 241

Met Ala Ala Ala Ser Arg Ser Ala Ser Gly Trp Ala Leu Leu Leu
1               5                   10                  15

Val Ala Leu Trp Gln Gln Arg Ala Ala Gly
            20                  25

<210> SEQ ID NO 242
<211> LENGTH: 28
<212> TYPE: PRT
<213> ORGANISM: Homo sapiens

<400> SEQUENCE: 242

Met His Ser Lys Val Thr Ile Ile Cys Ile Arg Phe Leu Phe Trp Phe
1               5                   10                  15

Leu Leu Leu Cys Met Leu Ile Gly Lys Ser His Thr
            20                  25

<210> SEQ ID NO 243
<211> LENGTH: 30

-continued

<212> TYPE: PRT
<213> ORGANISM: Homo sapiens

<400> SEQUENCE: 243

Met Ala Phe Pro Pro Arg Arg Leu Arg Leu Gly Pro Arg Gly Leu
1               5                   10                  15

Pro Leu Leu Leu Ser Gly Leu Leu Leu Pro Leu Cys Arg Ala
            20                  25                  30

<210> SEQ ID NO 244
<211> LENGTH: 14
<212> TYPE: PRT
<213> ORGANISM: Homo sapiens

<400> SEQUENCE: 244

Met Arg Ala Leu Ala Val Leu Ser Val Thr Leu Val Met Ala
1               5                   10

<210> SEQ ID NO 245
<211> LENGTH: 15
<212> TYPE: PRT
<213> ORGANISM: Homo sapiens

<400> SEQUENCE: 245

Met Ala Leu Leu Leu Leu Ser Leu Gly Leu Ser Leu Ile Ala Ala
1               5                   10                  15

<210> SEQ ID NO 246
<211> LENGTH: 15
<212> TYPE: PRT
<213> ORGANISM: Homo sapiens

<400> SEQUENCE: 246

Met Asn Arg Val Leu Cys Ala Pro Ala Ala Gly Ala Val Arg Ala
1               5                   10                  15

<210> SEQ ID NO 247
<211> LENGTH: 15
<212> TYPE: PRT
<213> ORGANISM: Homo sapiens

<400> SEQUENCE: 247

Met Asn Pro Leu Leu Ile Leu Ala Phe Val Gly Ala Ala Val Ala
1               5                   10                  15

<210> SEQ ID NO 248
<211> LENGTH: 15
<212> TYPE: PRT
<213> ORGANISM: Homo sapiens

<400> SEQUENCE: 248

Met Lys Leu Gly Leu Leu Cys Ala Leu Leu Ser Leu Leu Ala Gly
1               5                   10                  15

<210> SEQ ID NO 249
<211> LENGTH: 16
<212> TYPE: PRT
<213> ORGANISM: Homo sapiens

<400> SEQUENCE: 249

Met Leu Gly Ile Thr Val Leu Ala Ala Leu Leu Ala Cys Ala Ser Ser
1               5                   10                  15

<210> SEQ ID NO 250

-continued

<211> LENGTH: 15
<212> TYPE: PRT
<213> ORGANISM: Homo sapiens

<400> SEQUENCE: 250

Met Arg Thr Leu Leu Thr Ile Leu Thr Val Gly Ser Leu Ala Ala
1               5                   10                  15

<210> SEQ ID NO 251
<211> LENGTH: 15
<212> TYPE: PRT
<213> ORGANISM: Homo sapiens

<400> SEQUENCE: 251

Met Arg Leu Leu Thr Leu Leu Gly Leu Leu Cys Gly Ser Val Ala
1               5                   10                  15

<210> SEQ ID NO 252
<211> LENGTH: 15
<212> TYPE: PRT
<213> ORGANISM: Homo sapiens

<400> SEQUENCE: 252

Met Lys Ile Ile Ile Leu Leu Gly Phe Leu Gly Ala Thr Leu Ser
1               5                   10                  15

<210> SEQ ID NO 253
<211> LENGTH: 15
<212> TYPE: PRT
<213> ORGANISM: Homo sapiens

<400> SEQUENCE: 253

Met Lys Val Leu Leu Leu Thr Gly Leu Gly Ala Leu Phe Phe Ala
1               5                   10                  15

<210> SEQ ID NO 254
<211> LENGTH: 15
<212> TYPE: PRT
<213> ORGANISM: Homo sapiens

<400> SEQUENCE: 254

Met Ala Met Gly Leu Phe Arg Val Cys Leu Val Val Val Thr Ala
1               5                   10                  15

<210> SEQ ID NO 255
<211> LENGTH: 16
<212> TYPE: PRT
<213> ORGANISM: Homo sapiens

<400> SEQUENCE: 255

Met Leu Leu Pro Leu Leu Leu Ser Ser Leu Leu Gly Gly Ser Gln Ala
1               5                   10                  15

<210> SEQ ID NO 256
<211> LENGTH: 16
<212> TYPE: PRT
<213> ORGANISM: Homo sapiens

<400> SEQUENCE: 256

Met Leu Leu Leu Pro Leu Leu Leu Pro Val Leu Gly Ala Gly Ser Leu
1               5                   10                  15

<210> SEQ ID NO 257
<211> LENGTH: 15
<212> TYPE: PRT

```
<213> ORGANISM: Homo sapiens

<400> SEQUENCE: 257

Leu Thr Val Thr Leu Met Val Leu Ser Ser Arg Leu Ala Phe Ala
1               5                   10                  15

<210> SEQ ID NO 258
<211> LENGTH: 17
<212> TYPE: PRT
<213> ORGANISM: Homo sapiens

<400> SEQUENCE: 258

Met Ala Gln Val Leu Ile Val Gly Ala Gly Met Thr Gly Ser Leu Cys
1               5                   10                  15

Ala

<210> SEQ ID NO 259
<211> LENGTH: 14
<212> TYPE: PRT
<213> ORGANISM: Homo sapiens

<400> SEQUENCE: 259

Met Leu Leu Leu Leu Leu Leu Ala Pro Leu Phe Leu Arg Pro
1               5                   10

<210> SEQ ID NO 260
<211> LENGTH: 16
<212> TYPE: PRT
<213> ORGANISM: Homo sapiens

<400> SEQUENCE: 260

Met Arg Val Leu Ala Cys Leu Leu Ala Ala Leu Val Gly Ile Gln Ala
1               5                   10                  15

<210> SEQ ID NO 261
<211> LENGTH: 16
<212> TYPE: PRT
<213> ORGANISM: Homo sapiens

<400> SEQUENCE: 261

Met Leu Leu Val Leu Leu Ser Val Val Leu Leu Ala Leu Ser Ser Ala
1               5                   10                  15

<210> SEQ ID NO 262
<211> LENGTH: 15
<212> TYPE: PRT
<213> ORGANISM: Homo sapiens

<400> SEQUENCE: 262

Met Val Ala Ala Ala Ala Ala Thr Glu Ala Arg Leu Arg Arg Arg
1               5                   10                  15

<210> SEQ ID NO 263
<211> LENGTH: 14
<212> TYPE: PRT
<213> ORGANISM: Homo sapiens

<400> SEQUENCE: 263

Met Lys Glu Tyr Val Leu Leu Leu Phe Leu Ala Leu Cys Ser
1               5                   10

<210> SEQ ID NO 264
<211> LENGTH: 17
<212> TYPE: PRT
```

-continued

<213> ORGANISM: Homo sapiens

<400> SEQUENCE: 264

Met Ala Ala Gly Ala Val Phe Leu Ala Leu Ser Ala Gln Leu Leu Gln
1               5                   10                  15

Ala

<210> SEQ ID NO 265
<211> LENGTH: 17
<212> TYPE: PRT
<213> ORGANISM: Homo sapiens

<400> SEQUENCE: 265

Met Ala Ala Gly Ala Val Phe Leu Ala Leu Ser Ala Gln Leu Leu Gln
1               5                   10                  15

Ala

<210> SEQ ID NO 266
<211> LENGTH: 16
<212> TYPE: PRT
<213> ORGANISM: Homo sapiens

<400> SEQUENCE: 266

Met Trp Arg Leu Ala Leu Gly Gly Val Phe Leu Ala Ala Ala Gln Ala
1               5                   10                  15

<210> SEQ ID NO 267
<211> LENGTH: 14
<212> TYPE: PRT
<213> ORGANISM: Homo sapiens

<400> SEQUENCE: 267

Met Leu Trp Leu Leu Phe Phe Leu Val Thr Ala Ile His Ala
1               5                   10

<210> SEQ ID NO 268
<211> LENGTH: 17
<212> TYPE: PRT
<213> ORGANISM: Homo sapiens

<400> SEQUENCE: 268

Met Gly Ser Arg Cys Ala Leu Ala Leu Ala Val Leu Ser Ala Leu Leu
1               5                   10                  15

Cys

<210> SEQ ID NO 269
<211> LENGTH: 17
<212> TYPE: PRT
<213> ORGANISM: Homo sapiens

<400> SEQUENCE: 269

Met Ala Cys Ala Ala Val Met Ile Pro Gly Leu Leu Arg Cys Ser Val
1               5                   10                  15

Gly

<210> SEQ ID NO 270
<211> LENGTH: 16
<212> TYPE: PRT
<213> ORGANISM: Homo sapiens

<400> SEQUENCE: 270

Met Lys Arg Leu Val Cys Val Leu Leu Val Cys Ser Ser Ala Val Ala
1               5                   10                  15

-continued

```
1               5                   10                  15
```

<210> SEQ ID NO 271
<211> LENGTH: 19
<212> TYPE: PRT
<213> ORGANISM: Homo sapiens

<400> SEQUENCE: 271

```
Met Gly Gly Ala Gly Ile Leu Leu Leu Leu Ala Gly Ala Gly Val
1               5                   10                  15

Val Val Ala
```

<210> SEQ ID NO 272
<211> LENGTH: 17
<212> TYPE: PRT
<213> ORGANISM: Homo sapiens

<400> SEQUENCE: 272

```
Met Leu Leu Leu Gly Ile Leu Thr Leu Ala Phe Ala Gly Arg Thr Ala
1               5                   10                  15

Gly
```

<210> SEQ ID NO 273
<211> LENGTH: 16
<212> TYPE: PRT
<213> ORGANISM: Homo sapiens

<400> SEQUENCE: 273

```
Met Asp Val Leu Phe Val Ala Ile Phe Ala Val Pro Leu Ile Leu Gly
1               5                   10                  15
```

<210> SEQ ID NO 274
<211> LENGTH: 14
<212> TYPE: PRT
<213> ORGANISM: Homo sapiens

<400> SEQUENCE: 274

```
Met Ala Arg Thr Arg Asp Arg Val Arg Leu Leu Leu Leu Leu
1               5                   10
```

<210> SEQ ID NO 275
<211> LENGTH: 16
<212> TYPE: PRT
<213> ORGANISM: Homo sapiens

<400> SEQUENCE: 275

```
Met Lys Arg Ser Val Ala Val Trp Leu Leu Val Gly Leu Ser Leu Gly
1               5                   10                  15
```

<210> SEQ ID NO 276
<211> LENGTH: 16
<212> TYPE: PRT
<213> ORGANISM: Homo sapiens

<400> SEQUENCE: 276

```
Met Thr Pro Ile Val Thr Val Leu Ile Cys Leu Arg Leu Ser Leu Gly
1               5                   10                  15
```

<210> SEQ ID NO 277
<211> LENGTH: 16
<212> TYPE: PRT
<213> ORGANISM: Homo sapiens

<400> SEQUENCE: 277

Met Glu Thr Phe Pro Leu Leu Leu Leu Ser Leu Gly Leu Val Leu Ala
1               5                   10                  15

<210> SEQ ID NO 278
<211> LENGTH: 16
<212> TYPE: PRT
<213> ORGANISM: Homo sapiens

<400> SEQUENCE: 278

Met Arg Gly Leu Gly Leu Trp Leu Leu Gly Ala Met Met Leu Pro Ala
1               5                   10                  15

<210> SEQ ID NO 279
<211> LENGTH: 18
<212> TYPE: PRT
<213> ORGANISM: Homo sapiens

<400> SEQUENCE: 279

Met Gly Arg Leu Leu Ala Leu Val Val Gly Ala Ala Leu Val Ser Ser
1               5                   10                  15

Ala Cys

<210> SEQ ID NO 280
<211> LENGTH: 15
<212> TYPE: PRT
<213> ORGANISM: Homo sapiens

<400> SEQUENCE: 280

Met Leu Phe Ser Ala Leu Leu Leu Glu Val Ile Trp Ile Leu Ala
1               5                   10                  15

<210> SEQ ID NO 281
<211> LENGTH: 16
<212> TYPE: PRT
<213> ORGANISM: Homo sapiens

<400> SEQUENCE: 281

Met Glu Pro Gly Leu Trp Leu Leu Phe Gly Leu Thr Val Thr Ser Ala
1               5                   10                  15

<210> SEQ ID NO 282
<211> LENGTH: 17
<212> TYPE: PRT
<213> ORGANISM: Homo sapiens

<400> SEQUENCE: 282

Met Ser Ser Ser Ser Trp Leu Leu Leu Ser Leu Val Ala Val Thr Ala
1               5                   10                  15

Ala

<210> SEQ ID NO 283
<211> LENGTH: 16
<212> TYPE: PRT
<213> ORGANISM: Homo sapiens

<400> SEQUENCE: 283

Met Ala Pro Lys Leu Ile Thr Val Leu Cys Leu Gly Phe Cys Leu Asn
1               5                   10                  15

<210> SEQ ID NO 284
<211> LENGTH: 16
<212> TYPE: PRT
<213> ORGANISM: Homo sapiens

<400> SEQUENCE: 284

Met Ala Val Leu Phe Leu Leu Leu Phe Leu Cys Gly Thr Pro Gln Ala
1               5                   10                  15

<210> SEQ ID NO 285
<211> LENGTH: 17
<212> TYPE: PRT
<213> ORGANISM: Homo sapiens

<400> SEQUENCE: 285

Met Gly Leu Ser Ile Phe Leu Leu Leu Cys Val Leu Gly Leu Ser Gln
1               5                   10                  15

Ala

<210> SEQ ID NO 286
<211> LENGTH: 16
<212> TYPE: PRT
<213> ORGANISM: Homo sapiens

<400> SEQUENCE: 286

Met Arg Arg Leu Leu Ile Pro Leu Ala Leu Trp Leu Gly Ala Val Gly
1               5                   10                  15

<210> SEQ ID NO 287
<211> LENGTH: 16
<212> TYPE: PRT
<213> ORGANISM: Homo sapiens

<400> SEQUENCE: 287

Met Leu Ile Ala Thr Ser Phe Phe Leu Phe Phe Ser Ser Val Val Ala
1               5                   10                  15

<210> SEQ ID NO 288
<211> LENGTH: 16
<212> TYPE: PRT
<213> ORGANISM: Homo sapiens

<400> SEQUENCE: 288

Met Arg Trp Ile Leu Phe Ile Gly Ala Leu Ile Gly Ser Ser Ile Cys
1               5                   10                  15

<210> SEQ ID NO 289
<211> LENGTH: 18
<212> TYPE: PRT
<213> ORGANISM: Homo sapiens

<400> SEQUENCE: 289

Met Ile Pro Leu Leu Leu Ala Ala Leu Leu Cys Val Pro Ala Gly Ala
1               5                   10                  15

Leu Thr

<210> SEQ ID NO 290
<211> LENGTH: 17
<212> TYPE: PRT
<213> ORGANISM: Homo sapiens

<400> SEQUENCE: 290

Met Val Thr Lys Ala Phe Val Leu Leu Ala Ile Phe Ala Glu Ala Ser
1               5                   10                  15

Ala

<210> SEQ ID NO 291
<211> LENGTH: 16
<212> TYPE: PRT
<213> ORGANISM: Homo sapiens

<400> SEQUENCE: 291

Met Trp Gln Leu Leu Leu Pro Thr Ala Leu Leu Leu Val Ser Ala
1               5                   10                  15

<210> SEQ ID NO 292
<211> LENGTH: 16
<212> TYPE: PRT
<213> ORGANISM: Homo sapiens

<400> SEQUENCE: 292

Met Trp Gln Leu Leu Leu Pro Thr Ala Leu Leu Leu Val Ser Ala
1               5                   10                  15

<210> SEQ ID NO 293
<211> LENGTH: 17
<212> TYPE: PRT
<213> ORGANISM: Homo sapiens

<400> SEQUENCE: 293

Met Val Pro Val Leu Leu Ser Leu Leu His Leu Leu Gly Pro Ala Ile
1               5                   10                  15

Pro

<210> SEQ ID NO 294
<211> LENGTH: 18
<212> TYPE: PRT
<213> ORGANISM: Homo sapiens

<400> SEQUENCE: 294

Met Gly Pro Glu Ala Leu Ser Ser Leu Leu Leu Leu Leu Val Ala
1               5                   10                  15

Ser Gly

<210> SEQ ID NO 295
<211> LENGTH: 18
<212> TYPE: PRT
<213> ORGANISM: Homo sapiens

<400> SEQUENCE: 295

Met Ser Gln Val Met Ser Ser Pro Leu Leu Ala Gly Gly His Ala Val
1               5                   10                  15

Ser Leu

<210> SEQ ID NO 296
<211> LENGTH: 17
<212> TYPE: PRT
<213> ORGANISM: Homo sapiens

<400> SEQUENCE: 296

Met Leu Leu Pro Ala Leu Leu Phe Gly Met Ala Trp Ala Leu Ala Asp
1               5                   10                  15

Gly

<210> SEQ ID NO 297
<211> LENGTH: 17
<212> TYPE: PRT
<213> ORGANISM: Homo sapiens

```
<400> SEQUENCE: 297

Met Val Leu Leu Cys Leu Phe Leu Ala Ser Leu Ala Ala Thr Pro Arg
1               5                   10                  15

Ala

<210> SEQ ID NO 298
<211> LENGTH: 15
<212> TYPE: PRT
<213> ORGANISM: Homo sapiens

<400> SEQUENCE: 298

Met Trp Phe Leu Thr Thr Leu Leu Leu Trp Val Pro Val Asp Gly
1               5                   10                  15

<210> SEQ ID NO 299
<211> LENGTH: 15
<212> TYPE: PRT
<213> ORGANISM: Homo sapiens

<400> SEQUENCE: 299

Met Trp Phe Leu Thr Thr Leu Leu Leu Trp Val Pro Val Asp Gly
1               5                   10                  15

<210> SEQ ID NO 300
<211> LENGTH: 17
<212> TYPE: PRT
<213> ORGANISM: Homo sapiens

<400> SEQUENCE: 300

Met Trp Leu Phe Phe Gly Ile Thr Gly Leu Leu Thr Ala Ala Leu Ser
1               5                   10                  15

Gly

<210> SEQ ID NO 301
<211> LENGTH: 18
<212> TYPE: PRT
<213> ORGANISM: Homo sapiens

<400> SEQUENCE: 301

Met Ala Val Pro Ala Arg Thr Cys Gly Ala Ser Arg Pro Gly Pro Ala
1               5                   10                  15

Arg Thr

<210> SEQ ID NO 302
<211> LENGTH: 17
<212> TYPE: PRT
<213> ORGANISM: Homo sapiens

<400> SEQUENCE: 302

Met Trp Ala Gln Leu Leu Leu Gly Met Leu Ala Leu Ser Pro Ala Ile
1               5                   10                  15

Ala

<210> SEQ ID NO 303
<211> LENGTH: 18
<212> TYPE: PRT
<213> ORGANISM: Homo sapiens

<400> SEQUENCE: 303

Met Asp Phe Gly Leu Ala Leu Leu Leu Ala Gly Leu Leu Gly Leu Leu
1               5                   10                  15
```

Leu Gly

<210> SEQ ID NO 304
<211> LENGTH: 16
<212> TYPE: PRT
<213> ORGANISM: Homo sapiens

<400> SEQUENCE: 304

Met Arg Thr Leu Leu Val Leu Trp Leu Ala Thr Arg Gly Ser Ala
1               5                   10                  15

<210> SEQ ID NO 305
<211> LENGTH: 16
<212> TYPE: PRT
<213> ORGANISM: Homo sapiens

<400> SEQUENCE: 305

Met Val Pro His Leu Leu Leu Cys Leu Leu Pro Leu Val Arg Ala
1               5                   10                  15

<210> SEQ ID NO 306
<211> LENGTH: 16
<212> TYPE: PRT
<213> ORGANISM: Homo sapiens

<400> SEQUENCE: 306

Met Phe Leu Leu Leu Ala Leu Leu Thr Glu Leu Gly Arg Leu Gln Ala
1               5                   10                  15

<210> SEQ ID NO 307
<211> LENGTH: 18
<212> TYPE: PRT
<213> ORGANISM: Homo sapiens

<400> SEQUENCE: 307

Met Ile Thr Phe Leu Pro Leu Leu Leu Gly Leu Ser Leu Gly Cys Thr
1               5                   10                  15

Gly Ala

<210> SEQ ID NO 308
<211> LENGTH: 17
<212> TYPE: PRT
<213> ORGANISM: Homo sapiens

<400> SEQUENCE: 308

Met Leu Ala Val Leu Tyr Leu Leu Val Lys Thr Ala Lys Leu Gly Thr
1               5                   10                  15

Ser

<210> SEQ ID NO 309
<211> LENGTH: 19
<212> TYPE: PRT
<213> ORGANISM: Homo sapiens

<400> SEQUENCE: 309

Met Ala Pro Pro Ala Ala Arg Leu Ala Leu Leu Ser Ala Ala Ala Leu
1               5                   10                  15

Thr Leu Ala

<210> SEQ ID NO 310
<211> LENGTH: 17
<212> TYPE: PRT
<213> ORGANISM: Homo sapiens

```
<400> SEQUENCE: 310

Met Arg Pro Leu Leu Gly Leu Leu Val Phe Ala Gly Cys Thr Phe
1               5                   10                  15

Ala

<210> SEQ ID NO 311
<211> LENGTH: 16
<212> TYPE: PRT
<213> ORGANISM: Homo sapiens

<400> SEQUENCE: 311

Met Leu Ser Leu Leu Val Trp Ile Leu Thr Leu Ser Asp Thr Phe Ser
1               5                   10                  15

<210> SEQ ID NO 312
<211> LENGTH: 17
<212> TYPE: PRT
<213> ORGANISM: Homo sapiens

<400> SEQUENCE: 312

Met Val Pro Pro Val Trp Thr Leu Leu Leu Val Gly Ala Ala Leu
1               5                   10                  15

Phe

<210> SEQ ID NO 313
<211> LENGTH: 17
<212> TYPE: PRT
<213> ORGANISM: Homo sapiens

<400> SEQUENCE: 313

Met Ala Pro Lys Leu Leu Leu Leu Cys Leu Phe Ser Gly Leu His
1               5                   10                  15

Ala

<210> SEQ ID NO 314
<211> LENGTH: 18
<212> TYPE: PRT
<213> ORGANISM: Homo sapiens

<400> SEQUENCE: 314

Met Arg Asp Leu Pro Leu Thr Ser Leu Ala Leu Val Leu Ser Ala Leu
1               5                   10                  15

Gly Ala

<210> SEQ ID NO 315
<211> LENGTH: 16
<212> TYPE: PRT
<213> ORGANISM: Homo sapiens

<400> SEQUENCE: 315

Met Pro Met Asp Leu Ile Leu Val Val Trp Phe Cys Val Cys Thr Ala
1               5                   10                  15

<210> SEQ ID NO 316
<211> LENGTH: 19
<212> TYPE: PRT
<213> ORGANISM: Homo sapiens

<400> SEQUENCE: 316

Met Lys Gly Ile Leu Val Ala Gly Ile Thr Ala Val Leu Val Ala Ala
1               5                   10                  15
```

Val Glu Ser

<210> SEQ ID NO 317
<211> LENGTH: 19
<212> TYPE: PRT
<213> ORGANISM: Homo sapiens

<400> SEQUENCE: 317

Met Ala Arg Gly Ser Ala Leu Leu Ala Ser Leu Leu Ala Ala
1               5                   10                  15

Ala Leu Ser

<210> SEQ ID NO 318
<211> LENGTH: 16
<212> TYPE: PRT
<213> ORGANISM: Homo sapiens

<400> SEQUENCE: 318

Met Asn Tyr Ser Leu His Leu Ala Phe Val Cys Leu Ser Leu Phe Thr
1               5                   10                  15

<210> SEQ ID NO 319
<211> LENGTH: 18
<212> TYPE: PRT
<213> ORGANISM: Homo sapiens

<400> SEQUENCE: 319

Met Thr Ala Pro Trp Val Ala Leu Ala Leu Leu Trp Gly Ser Leu Cys
1               5                   10                  15

Ala Gly

<210> SEQ ID NO 320
<211> LENGTH: 18
<212> TYPE: PRT
<213> ORGANISM: Homo sapiens

<400> SEQUENCE: 320

Met Gly Val Met Ala Met Leu Met Leu Pro Leu Leu Leu Gly Ile
1               5                   10                  15

Ser Gly

<210> SEQ ID NO 321
<211> LENGTH: 18
<212> TYPE: PRT
<213> ORGANISM: Homo sapiens

<400> SEQUENCE: 321

Met Arg Leu Leu Leu Leu Val Pro Leu Leu Ala Pro Ala Pro Gly
1               5                   10                  15

Ser Ser

<210> SEQ ID NO 322
<211> LENGTH: 17
<212> TYPE: PRT
<213> ORGANISM: Homo sapiens

<400> SEQUENCE: 322

Met Leu Lys Met Leu Ser Phe Lys Leu Leu Leu Ala Val Ala Leu
1               5                   10                  15

Gly

<210> SEQ ID NO 323
<211> LENGTH: 20
<212> TYPE: PRT
<213> ORGANISM: Homo sapiens

<400> SEQUENCE: 323

Met Ala Pro Ala Pro Val Thr Leu Leu Ala Pro Gly Ala Ala Ser Ser
1               5                   10                  15
Met Ser Cys Ser
            20

<210> SEQ ID NO 324
<211> LENGTH: 18
<212> TYPE: PRT
<213> ORGANISM: Homo sapiens

<400> SEQUENCE: 324

Met Thr Ser Ser Leu Leu Leu Ala Phe Leu Leu Leu Ala Pro Thr Thr
1               5                   10                  15
Val Ala

<210> SEQ ID NO 325
<211> LENGTH: 18
<212> TYPE: PRT
<213> ORGANISM: Homo sapiens

<400> SEQUENCE: 325

Met Gly Ser Cys Ala Arg Leu Leu Leu Leu Trp Gly Cys Thr Val Val
1               5                   10                  15
Ala Ala

<210> SEQ ID NO 326
<211> LENGTH: 21
<212> TYPE: PRT
<213> ORGANISM: Homo sapiens

<400> SEQUENCE: 326

Met Ala Ala Ala Gly Ala Ala Val Ala Arg Ser Pro Gly Ile Gly Ala
1               5                   10                  15
Gly Pro Ala Leu Arg
            20

<210> SEQ ID NO 327
<211> LENGTH: 16
<212> TYPE: PRT
<213> ORGANISM: Homo sapiens

<400> SEQUENCE: 327

Met Lys Ile Leu Cys Ile Phe Leu Thr Phe Val Phe Thr Val Ser Cys
1               5                   10                  15

<210> SEQ ID NO 328
<211> LENGTH: 18
<212> TYPE: PRT
<213> ORGANISM: Homo sapiens

<400> SEQUENCE: 328

Met Arg Leu Leu Val Ala Pro Leu Leu Leu Ala Trp Val Ala Gly Ala
1               5                   10                  15
Thr Ala

```
<210> SEQ ID NO 329
<211> LENGTH: 18
<212> TYPE: PRT
<213> ORGANISM: Homo sapiens

<400> SEQUENCE: 329

Met Lys Pro Leu Leu Ala Ile Ser Leu Ser Leu Ile Ala Ala Leu
1               5                   10                  15

Gln Ala

<210> SEQ ID NO 330
<211> LENGTH: 17
<212> TYPE: PRT
<213> ORGANISM: Homo sapiens

<400> SEQUENCE: 330

Met Leu Phe Leu Gln Phe Leu Leu Leu Ala Leu Leu Pro Gly Gly
1               5                   10                  15

Asp

<210> SEQ ID NO 331
<211> LENGTH: 19
<212> TYPE: PRT
<213> ORGANISM: Homo sapiens

<400> SEQUENCE: 331

Met Ala Gly Ser Leu Thr Gly Leu Leu Leu Leu Gln Ala Val Ser Trp
1               5                   10                  15

Ala Ser Gly

<210> SEQ ID NO 332
<211> LENGTH: 17
<212> TYPE: PRT
<213> ORGANISM: Homo sapiens

<400> SEQUENCE: 332

Leu Gly Leu Cys Trp Val Phe Leu Val Ala Leu Leu Arg Gly Val Leu
1               5                   10                  15

Cys

<210> SEQ ID NO 333
<211> LENGTH: 15
<212> TYPE: PRT
<213> ORGANISM: Homo sapiens

<400> SEQUENCE: 333

Met Lys Leu Phe Trp Leu Leu Phe Thr Ile Gly Phe Cys Trp Ala
1               5                   10                  15

<210> SEQ ID NO 334
<211> LENGTH: 18
<212> TYPE: PRT
<213> ORGANISM: Homo sapiens

<400> SEQUENCE: 334

Met Ala Leu Arg Arg Leu Gly Ala Ala Leu Leu Leu Leu Pro Leu Leu
1               5                   10                  15

Ala Ala

<210> SEQ ID NO 335
<211> LENGTH: 18
<212> TYPE: PRT
```

-continued

<213> ORGANISM: Homo sapiens

<400> SEQUENCE: 335

Met Ile Pro Ala Val Val Leu Leu Leu Leu Val Glu Gln Ala
1               5                   10                  15
Ala Ala

<210> SEQ ID NO 336
<211> LENGTH: 19
<212> TYPE: PRT
<213> ORGANISM: Homo sapiens

<400> SEQUENCE: 336

Met Ala Arg Ala Arg Ala Gly Ala Leu Leu Ala Leu Trp Val Leu Gly
1               5                   10                  15
Ala Ala Ala

<210> SEQ ID NO 337
<211> LENGTH: 18
<212> TYPE: PRT
<213> ORGANISM: Homo sapiens

<400> SEQUENCE: 337

Met Lys Ala Leu Cys Leu Leu Leu Pro Val Leu Gly Leu Leu Val
1               5                   10                  15
Ser Ser

<210> SEQ ID NO 338
<211> LENGTH: 18
<212> TYPE: PRT
<213> ORGANISM: Homo sapiens

<400> SEQUENCE: 338

Met Leu Ser Leu Leu Leu Leu Ala Leu Pro Val Leu Ala Ser Pro Ala
1               5                   10                  15
Tyr Val

<210> SEQ ID NO 339
<211> LENGTH: 19
<212> TYPE: PRT
<213> ORGANISM: Homo sapiens

<400> SEQUENCE: 339

Met Lys Ala Ser Val Val Leu Ser Leu Leu Gly Tyr Leu Val Val Pro
1               5                   10                  15
Ser Gly Ala

<210> SEQ ID NO 340
<211> LENGTH: 18
<212> TYPE: PRT
<213> ORGANISM: Homo sapiens

<400> SEQUENCE: 340

Met Leu Leu Leu Leu Leu Leu Leu Pro Pro Leu Leu Cys Gly Arg Val
1               5                   10                  15
Gly Ala

<210> SEQ ID NO 341
<211> LENGTH: 18
<212> TYPE: PRT
<213> ORGANISM: Homo sapiens

<400> SEQUENCE: 341

Met Leu Leu Leu Phe Ser Val Ile Leu Ile Ser Trp Val Ser Thr Val
1               5                   10                  15

Gly Gly

<210> SEQ ID NO 342
<211> LENGTH: 17
<212> TYPE: PRT
<213> ORGANISM: Homo sapiens

<400> SEQUENCE: 342

Met Trp Gln Leu Trp Ala Ser Leu Cys Cys Leu Leu Val Leu Ala Asn
1               5                   10                  15

Ala

<210> SEQ ID NO 343
<211> LENGTH: 17
<212> TYPE: PRT
<213> ORGANISM: Homo sapiens

<400> SEQUENCE: 343

Met Leu Met Leu Phe Val Phe Gly Val Leu Leu His Glu Val Ser Leu
1               5                   10                  15

Ser

<210> SEQ ID NO 344
<211> LENGTH: 18
<212> TYPE: PRT
<213> ORGANISM: Homo sapiens

<400> SEQUENCE: 344

Met Arg Ser Leu Leu Leu Ser Ala Phe Cys Leu Leu Glu Ala Ala
1               5                   10                  15

Leu Ala

<210> SEQ ID NO 345
<211> LENGTH: 19
<212> TYPE: PRT
<213> ORGANISM: Homo sapiens

<400> SEQUENCE: 345

Met Gln Gln Arg Gly Leu Ala Ile Val Ala Leu Ala Val Cys Ala Ala
1               5                   10                  15

Leu His Ala

<210> SEQ ID NO 346
<211> LENGTH: 19
<212> TYPE: PRT
<213> ORGANISM: Homo sapiens

<400> SEQUENCE: 346

Met Gly Ala Arg Gly Ala Leu Leu Leu Ala Leu Leu Leu Ala Arg Ala
1               5                   10                  15

Gly Leu Arg

<210> SEQ ID NO 347
<211> LENGTH: 20
<212> TYPE: PRT
<213> ORGANISM: Homo sapiens

```
<400> SEQUENCE: 347

Met Pro Leu Ala Leu Thr Leu Leu Leu Ser Gly Leu Gly Ala Pro
1               5                   10                  15

Gly Gly Trp Gly
            20

<210> SEQ ID NO 348
<211> LENGTH: 22
<212> TYPE: PRT
<213> ORGANISM: Homo sapiens

<400> SEQUENCE: 348

Met Ala Ala Ala Gly Leu Val Ala Val Ala Ala Ala Glu Tyr Ser
1               5                   10                  15

Gly Thr Val Ala Ser Gly
            20

<210> SEQ ID NO 349
<211> LENGTH: 18
<212> TYPE: PRT
<213> ORGANISM: Homo sapiens

<400> SEQUENCE: 349

Met Ser Thr Met Arg Leu Leu Thr Leu Ala Leu Leu Phe Ser Cys Ser
1               5                   10                  15

Val Ala

<210> SEQ ID NO 350
<211> LENGTH: 20
<212> TYPE: PRT
<213> ORGANISM: Homo sapiens

<400> SEQUENCE: 350

Met Ser Ile Ser Ser Ala Leu Ala Met Val Phe Met Gly Ala Lys Gly
1               5                   10                  15

Asn Thr Ala Ala
            20

<210> SEQ ID NO 351
<211> LENGTH: 18
<212> TYPE: PRT
<213> ORGANISM: Homo sapiens

<400> SEQUENCE: 351

Met Lys Leu His Cys Cys Leu Phe Thr Leu Val Ala Ser Ile Ile Val
1               5                   10                  15

Pro Ala

<210> SEQ ID NO 352
<211> LENGTH: 19
<212> TYPE: PRT
<213> ORGANISM: Homo sapiens

<400> SEQUENCE: 352

Met Leu Thr Pro Pro Leu Leu Leu Leu Pro Leu Leu Ser Ala Leu
1               5                   10                  15

Val Ala Ala

<210> SEQ ID NO 353
<211> LENGTH: 18
<212> TYPE: PRT
```

<213> ORGANISM: Homo sapiens

<400> SEQUENCE: 353

Met Pro Ala Arg Arg Leu Leu Leu Leu Thr Leu Leu Pro Gly
1               5                   10                  15
Leu Gly

<210> SEQ ID NO 354
<211> LENGTH: 18
<212> TYPE: PRT
<213> ORGANISM: Homo sapiens

<400> SEQUENCE: 354

Met Phe Leu Leu Leu Thr Ala Leu Gln Val Leu Ala Ile Ala Met Thr
1               5                   10                  15
Gln Ser

<210> SEQ ID NO 355
<211> LENGTH: 17
<212> TYPE: PRT
<213> ORGANISM: Homo sapiens

<400> SEQUENCE: 355

Met Leu Leu Leu Leu Leu Pro Leu Leu Trp Gly Arg Glu Arg Ala Glu
1               5                   10                  15
Gly

<210> SEQ ID NO 356
<211> LENGTH: 19
<212> TYPE: PRT
<213> ORGANISM: Homo sapiens

<400> SEQUENCE: 356

Met Arg Thr Ile Ala Ile Leu Ala Ala Ile Leu Leu Val Ala Leu Gln
1               5                   10                  15
Ala Gln Ala

<210> SEQ ID NO 357
<211> LENGTH: 17
<212> TYPE: PRT
<213> ORGANISM: Homo sapiens

<400> SEQUENCE: 357

Met Ser Leu Ser Phe Leu Leu Leu Phe Phe Ser His Leu Ile Leu
1               5                   10                  15
Ser

<210> SEQ ID NO 358
<211> LENGTH: 18
<212> TYPE: PRT
<213> ORGANISM: Homo sapiens

<400> SEQUENCE: 358

Met Gly Arg Val Pro Leu Ala Trp Cys Leu Ala Leu Cys Gly Trp Ala
1               5                   10                  15
Cys Met

<210> SEQ ID NO 359
<211> LENGTH: 18
<212> TYPE: PRT
<213> ORGANISM: Homo sapiens

<400> SEQUENCE: 359

Met Gly Leu Leu Gly Ile Leu Cys Phe Leu Ile Phe Leu Gly Lys Thr
1               5                   10                  15

Trp Gly

<210> SEQ ID NO 360
<211> LENGTH: 18
<212> TYPE: PRT
<213> ORGANISM: Homo sapiens

<400> SEQUENCE: 360

Met Ala Phe Leu Ile Ile Leu Ile Thr Cys Phe Val Ile Ile Leu Ala
1               5                   10                  15

Thr Ser

<210> SEQ ID NO 361
<211> LENGTH: 18
<212> TYPE: PRT
<213> ORGANISM: Homo sapiens

<400> SEQUENCE: 361

Met Trp Leu Pro Leu Val Leu Leu Leu Ala Val Leu Leu Leu Ala Val
1               5                   10                  15

Leu Cys

<210> SEQ ID NO 362
<211> LENGTH: 20
<212> TYPE: PRT
<213> ORGANISM: Homo sapiens

<400> SEQUENCE: 362

Met Gly Gly Leu Leu Leu Ala Ala Phe Leu Ala Leu Val Ser Val Pro
1               5                   10                  15

Arg Ala Gln Ala
            20

<210> SEQ ID NO 363
<211> LENGTH: 20
<212> TYPE: PRT
<213> ORGANISM: Homo sapiens

<400> SEQUENCE: 363

Met Val Thr Leu Ala Glu Leu Leu Val Leu Leu Ala Ala Leu Leu Ala
1               5                   10                  15

Thr Val Ser Gly
            20

<210> SEQ ID NO 364
<211> LENGTH: 20
<212> TYPE: PRT
<213> ORGANISM: Homo sapiens

<400> SEQUENCE: 364

Met Gln Leu Thr Gly Lys Val Val Leu Ser Ala Ala Ala Leu Leu Leu
1               5                   10                  15

Val Thr Val Ala
            20

<210> SEQ ID NO 365
<211> LENGTH: 18

-continued

```
<212> TYPE: PRT
<213> ORGANISM: Homo sapiens

<400> SEQUENCE: 365

Met Met Trp Leu Leu Leu Thr Thr Thr Cys Leu Ile Cys Gly Thr Leu
1               5                   10                  15

Asn Ala

<210> SEQ ID NO 366
<211> LENGTH: 19
<212> TYPE: PRT
<213> ORGANISM: Homo sapiens

<400> SEQUENCE: 366

Met Arg Pro Val Ala Leu Leu Leu Pro Ser Leu Leu Ala Leu Leu
1               5                   10                  15

Ala His Gly

<210> SEQ ID NO 367
<211> LENGTH: 20
<212> TYPE: PRT
<213> ORGANISM: Homo sapiens

<400> SEQUENCE: 367

Met Gly Pro Ala Gly Cys Ala Phe Thr Leu Leu Leu Leu Gly Ser
1               5                   10                  15

Cys Leu His Ser
            20

<210> SEQ ID NO 368
<211> LENGTH: 18
<212> TYPE: PRT
<213> ORGANISM: Homo sapiens

<400> SEQUENCE: 368

Met Leu Pro Gln Ile Pro Phe Leu Leu Val Ser Leu Asn Leu Val
1               5                   10                  15

His Gly

<210> SEQ ID NO 369
<211> LENGTH: 18
<212> TYPE: PRT
<213> ORGANISM: Homo sapiens

<400> SEQUENCE: 369

Met Glu Val Val Leu Ile Phe Val Tyr Ser Leu Leu Val Pro Val
1               5                   10                  15

Leu Ala

<210> SEQ ID NO 370
<211> LENGTH: 19
<212> TYPE: PRT
<213> ORGANISM: Homo sapiens

<400> SEQUENCE: 370

Met Asp Leu Ser Ala Ala Ala Ala Leu Cys Leu Trp Leu Leu Ser Ala
1               5                   10                  15

Cys Arg Pro

<210> SEQ ID NO 371
<211> LENGTH: 18
```

```
<212> TYPE: PRT
<213> ORGANISM: Homo sapiens

<400> SEQUENCE: 371

Met Trp Leu Leu Arg Cys Val Leu Leu Cys Val Ser Leu Ser Leu Ala
1               5                   10                  15

Val Ser

<210> SEQ ID NO 372
<211> LENGTH: 19
<212> TYPE: PRT
<213> ORGANISM: Homo sapiens

<400> SEQUENCE: 372

Met Leu Ser Ser Val Val Phe Trp Gly Leu Ile Ala Leu Ile Gly Thr
1               5                   10                  15

Ser Arg Gly

<210> SEQ ID NO 373
<211> LENGTH: 22
<212> TYPE: PRT
<213> ORGANISM: Homo sapiens

<400> SEQUENCE: 373

Met Pro Gly Ala Ala Gly Val Leu Leu Leu Leu Leu Ser Gly Gly
1               5                   10                  15

Leu Gly Gly Val Gln Ala
            20

<210> SEQ ID NO 374
<211> LENGTH: 18
<212> TYPE: PRT
<213> ORGANISM: Homo sapiens

<400> SEQUENCE: 374

Met Glu Leu Leu Gln Val Thr Ile Leu Phe Leu Leu Pro Ser Ile Cys
1               5                   10                  15

Ser Ser

<210> SEQ ID NO 375
<211> LENGTH: 20
<212> TYPE: PRT
<213> ORGANISM: Homo sapiens

<400> SEQUENCE: 375

Met Thr Pro Ala Cys Pro Leu Leu Leu Ser Val Ile Leu Ser Leu Arg
1               5                   10                  15

Leu Ala Thr Ala
            20

<210> SEQ ID NO 376
<211> LENGTH: 20
<212> TYPE: PRT
<213> ORGANISM: Homo sapiens

<400> SEQUENCE: 376

Met Leu Leu Ala Leu Ala Leu Leu Leu Ala Phe Leu Pro Pro Ala Ser
1               5                   10                  15

Gln Lys Ser Ser
            20
```

```
<210> SEQ ID NO 377
<211> LENGTH: 19
<212> TYPE: PRT
<213> ORGANISM: Homo sapiens

<400> SEQUENCE: 377

Met Gly Arg Pro Leu Leu Leu Pro Leu Leu Pro Leu Leu Leu Pro Pro
1               5                   10                  15

Ala Phe Leu

<210> SEQ ID NO 378
<211> LENGTH: 20
<212> TYPE: PRT
<213> ORGANISM: Homo sapiens

<400> SEQUENCE: 378

Met Ala Phe Leu Pro Ser Trp Val Cys Val Leu Val Gly Ser Phe Ser
1               5                   10                  15

Ala Ser Leu Ala
            20

<210> SEQ ID NO 379
<211> LENGTH: 21
<212> TYPE: PRT
<213> ORGANISM: Homo sapiens

<400> SEQUENCE: 379

Met Gly Pro His Phe Thr Leu Leu Cys Ala Ala Leu Ala Gly Cys Leu
1               5                   10                  15

Leu Pro Ala Glu Gly
            20

<210> SEQ ID NO 380
<211> LENGTH: 19
<212> TYPE: PRT
<213> ORGANISM: Homo sapiens

<400> SEQUENCE: 380

Met Gly Val Leu Gly Arg Val Leu Leu Trp Leu Gln Leu Cys Ala Leu
1               5                   10                  15

Thr Gln Ala

<210> SEQ ID NO 381
<211> LENGTH: 19
<212> TYPE: PRT
<213> ORGANISM: Homo sapiens

<400> SEQUENCE: 381

Met Ala Gly Ile Phe Tyr Phe Ala Leu Phe Ser Cys Leu Phe Gly Ile
1               5                   10                  15

Cys Asp Ala

<210> SEQ ID NO 382
<211> LENGTH: 18
<212> TYPE: PRT
<213> ORGANISM: Homo sapiens

<400> SEQUENCE: 382

Met Glu Leu Leu Pro Leu Trp Leu Cys Leu Gly Phe His Phe Leu Thr
1               5                   10                  15

Val Gly
```

<210> SEQ ID NO 383
<211> LENGTH: 19
<212> TYPE: PRT
<213> ORGANISM: Homo sapiens

<400> SEQUENCE: 383

Met Thr Trp Leu Val Leu Leu Gly Thr Leu Leu Cys Met Leu Arg Val
1               5                   10                  15

Gly Leu Gly

<210> SEQ ID NO 384
<211> LENGTH: 19
<212> TYPE: PRT
<213> ORGANISM: Homo sapiens

<400> SEQUENCE: 384

Met Ser Asp Leu Gly Ala Val Ile Ser Leu Leu Leu Trp Gly Arg Gln
1               5                   10                  15

Leu Phe Ala

<210> SEQ ID NO 385
<211> LENGTH: 18
<212> TYPE: PRT
<213> ORGANISM: Homo sapiens

<400> SEQUENCE: 385

Met Ile Val Phe Ile Phe Leu Ala Met Gly Leu Ser Leu Glu Asn Glu
1               5                   10                  15

Tyr Thr

<210> SEQ ID NO 386
<211> LENGTH: 19
<212> TYPE: PRT
<213> ORGANISM: Homo sapiens

<400> SEQUENCE: 386

Met Phe Gly Thr Leu Leu Leu Tyr Cys Phe Phe Leu Ala Thr Val Pro
1               5                   10                  15

Ala Leu Ala

<210> SEQ ID NO 387
<211> LENGTH: 20
<212> TYPE: PRT
<213> ORGANISM: Homo sapiens

<400> SEQUENCE: 387

Met Trp Pro Leu Thr Val Pro Pro Leu Leu Leu Leu Leu Cys Ser
1               5                   10                  15

Gly Leu Ala Gly
            20

<210> SEQ ID NO 388
<211> LENGTH: 21
<212> TYPE: PRT
<213> ORGANISM: Homo sapiens

<400> SEQUENCE: 388

Met Pro Val Ile Ala Gly Gly Ile Leu Ala Ala Leu Leu Leu Ile
1               5                   10                  15

Val Val Val Leu Cys
            20

<210> SEQ ID NO 389
<211> LENGTH: 19
<212> TYPE: PRT
<213> ORGANISM: Homo sapiens

<400> SEQUENCE: 389

Met Ala Trp Thr Pro Leu Phe Leu Phe Leu Leu Thr Cys Cys Pro Gly
1               5                   10                  15

Ser Asn Ser

<210> SEQ ID NO 390
<211> LENGTH: 19
<212> TYPE: PRT
<213> ORGANISM: Homo sapiens

<400> SEQUENCE: 390

Met Leu Leu Leu Ile Asn Val Ile Leu Thr Leu Trp Val Ser Cys Ala
1               5                   10                  15

Asn Gly Gln

<210> SEQ ID NO 391
<211> LENGTH: 19
<212> TYPE: PRT
<213> ORGANISM: Homo sapiens

<400> SEQUENCE: 391

Met Leu Leu Leu Ile Asn Val Ile Leu Thr Leu Trp Val Ser Cys Ala
1               5                   10                  15

Asn Gly Gln

<210> SEQ ID NO 392
<211> LENGTH: 20
<212> TYPE: PRT
<213> ORGANISM: Homo sapiens

<400> SEQUENCE: 392

Met Lys Gly Leu Leu Pro Leu Ala Trp Phe Leu Ala Cys Ser Val Pro
1               5                   10                  15

Ala Val Gln Gly
            20

<210> SEQ ID NO 393
<211> LENGTH: 20
<212> TYPE: PRT
<213> ORGANISM: Homo sapiens

<400> SEQUENCE: 393

Met Thr Leu Ala Arg Phe Val Leu Ala Leu Met Leu Gly Ala Leu Pro
1               5                   10                  15

Glu Val Val Gly
            20

<210> SEQ ID NO 394
<211> LENGTH: 22
<212> TYPE: PRT
<213> ORGANISM: Homo sapiens

<400> SEQUENCE: 394

Met Arg Pro Pro Pro Ala Leu Ala Leu Ala Gly Leu Cys Leu Leu Ala
1               5                   10                  15

```
Leu Pro Ala Ala Ala Ala
        20
```

<210> SEQ ID NO 395
<211> LENGTH: 18
<212> TYPE: PRT
<213> ORGANISM: Homo sapiens

<400> SEQUENCE: 395

```
Met Asp Thr Ile Phe Leu Trp Ser Leu Leu Leu Phe Phe Gly Ser
1               5                   10                  15

Gln Ala
```

<210> SEQ ID NO 396
<211> LENGTH: 18
<212> TYPE: PRT
<213> ORGANISM: Homo sapiens

<400> SEQUENCE: 396

```
Met Ser Ile Leu Phe Tyr Val Ile Phe Leu Ala Tyr Leu Arg Gly Ile
1               5                   10                  15

Gln Gly
```

<210> SEQ ID NO 397
<211> LENGTH: 19
<212> TYPE: PRT
<213> ORGANISM: Homo sapiens

<400> SEQUENCE: 397

```
Met Gly Trp Thr Trp Arg Ile Leu Phe Leu Val Val Ile Ala Ala Gly
1               5                   10                  15

Ala Gln Ser
```

<210> SEQ ID NO 398
<211> LENGTH: 22
<212> TYPE: PRT
<213> ORGANISM: Homo sapiens

<400> SEQUENCE: 398

```
Met Ala Ala Pro Val Pro Trp Ala Cys Cys Ala Val Leu Ala Ala Ala
1               5                   10                  15

Ala Ala Val Val Tyr Ala
        20
```

<210> SEQ ID NO 399
<211> LENGTH: 19
<212> TYPE: PRT
<213> ORGANISM: Homo sapiens

<400> SEQUENCE: 399

```
Met Trp Gly Leu Val Arg Leu Leu Leu Ala Trp Leu Gly Gly Trp Gly
1               5                   10                  15

Cys Met Gly
```

<210> SEQ ID NO 400
<211> LENGTH: 21
<212> TYPE: PRT
<213> ORGANISM: Homo sapiens

<400> SEQUENCE: 400

```
Met Leu Gly Val Leu Glu Leu Leu Leu Leu Gly Ala Ala Trp Leu Ala
1               5                   10                  15
```

Gly Pro Ala Arg Gly
        20

<210> SEQ ID NO 401
<211> LENGTH: 18
<212> TYPE: PRT
<213> ORGANISM: Homo sapiens

<400> SEQUENCE: 401

Met Leu Leu Leu Leu Leu Leu Pro Leu Leu Trp Gly Arg Glu Arg Val
1               5                   10                  15

Glu Gly

<210> SEQ ID NO 402
<211> LENGTH: 20
<212> TYPE: PRT
<213> ORGANISM: Homo sapiens

<400> SEQUENCE: 402

Met Arg Pro Gly Leu Ser Phe Leu Leu Ala Leu Leu Phe Phe Leu Gly
1               5                   10                  15

Gln Ala Ala Gly
        20

<210> SEQ ID NO 403
<211> LENGTH: 17
<212> TYPE: PRT
<213> ORGANISM: Homo sapiens

<400> SEQUENCE: 403

Met His Trp Lys Met Leu Leu Leu Leu Leu Tyr Tyr Asn Ala Glu
1               5                   10                  15

Ala

<210> SEQ ID NO 404
<211> LENGTH: 22
<212> TYPE: PRT
<213> ORGANISM: Homo sapiens

<400> SEQUENCE: 404

Met Ala Val Lys Leu Gly Thr Leu Leu Ala Leu Ala Leu Gly Leu
1               5                   10                  15

Ala Gln Pro Ala Ser Ala
        20

<210> SEQ ID NO 405
<211> LENGTH: 20
<212> TYPE: PRT
<213> ORGANISM: Homo sapiens

<400> SEQUENCE: 405

Met Gln Lys Val Thr Leu Gly Leu Leu Val Phe Leu Ala Gly Phe Pro
1               5                   10                  15

Val Leu Asp Ala
        20

<210> SEQ ID NO 406
<211> LENGTH: 20
<212> TYPE: PRT
<213> ORGANISM: Homo sapiens

<400> SEQUENCE: 406

Met Ala Gln Leu Trp Leu Ser Cys Phe Leu Leu Pro Ala Leu Val Val
1               5                   10                  15

Ser Val Ala Ala
            20

<210> SEQ ID NO 407
<211> LENGTH: 21
<212> TYPE: PRT
<213> ORGANISM: Homo sapiens

<400> SEQUENCE: 407

Met Pro Ala Ile Ala Val Leu Ala Ala Ala Ala Ala Trp Cys Phe
1               5                   10                  15

Leu Gln Val Glu Ser
            20

<210> SEQ ID NO 408
<211> LENGTH: 19
<212> TYPE: PRT
<213> ORGANISM: Homo sapiens

<400> SEQUENCE: 408

Met Ala Met Val Ser Ala Met Ser Trp Val Leu Tyr Leu Trp Ile Ser
1               5                   10                  15

Ala Cys Ala

<210> SEQ ID NO 409
<211> LENGTH: 21
<212> TYPE: PRT
<213> ORGANISM: Homo sapiens

<400> SEQUENCE: 409

Met Gly Ser Ala Pro Trp Ala Pro Val Leu Leu Leu Ala Leu Gly Leu
1               5                   10                  15

Arg Gly Leu Gln Ala
            20

<210> SEQ ID NO 410
<211> LENGTH: 18
<212> TYPE: PRT
<213> ORGANISM: Homo sapiens

<400> SEQUENCE: 410

Met His Arg Leu Ile Phe Val Tyr Thr Leu Ile Cys Ala Asn Phe Cys
1               5                   10                  15

Ser Cys

<210> SEQ ID NO 411
<211> LENGTH: 22
<212> TYPE: PRT
<213> ORGANISM: Homo sapiens

<400> SEQUENCE: 411

Met Leu Leu Leu Trp Val Ser Val Val Ala Leu Ala Leu Ala Val
1               5                   10                  15

Leu Ala Pro Gly Ala Gly
            20

<210> SEQ ID NO 412
<211> LENGTH: 21
<212> TYPE: PRT

<213> ORGANISM: Homo sapiens

<400> SEQUENCE: 412

Met Ala Cys Leu Gly Phe Leu Leu Pro Val Gly Phe Leu Leu Leu Ile
1               5                   10                  15

Ser Thr Val Ala Gly
            20

<210> SEQ ID NO 413
<211> LENGTH: 20
<212> TYPE: PRT
<213> ORGANISM: Homo sapiens

<400> SEQUENCE: 413

Met Ala Ser Leu Gly Leu Leu Leu Leu Leu Leu Thr Ala Leu Pro
1               5                   10                  15

Pro Leu Trp Ser
            20

<210> SEQ ID NO 414
<211> LENGTH: 18
<212> TYPE: PRT
<213> ORGANISM: Homo sapiens

<400> SEQUENCE: 414

Met Val Leu Leu Ser Ile Leu Arg Ile Leu Phe Leu Cys Glu Leu Val
1               5                   10                  15

Leu Phe

<210> SEQ ID NO 415
<211> LENGTH: 20
<212> TYPE: PRT
<213> ORGANISM: Homo sapiens

<400> SEQUENCE: 415

Met Ser Pro Ala Pro Arg Pro Ser Arg Cys Leu Leu Leu Pro Leu Leu
1               5                   10                  15

Thr Leu Gly Thr
            20

<210> SEQ ID NO 416
<211> LENGTH: 19
<212> TYPE: PRT
<213> ORGANISM: Homo sapiens

<400> SEQUENCE: 416

Met Arg Leu Leu Trp Lys Leu Val Ile Leu Leu Pro Leu Ile Asn Ser
1               5                   10                  15

Ser Ala Gly

<210> SEQ ID NO 417
<211> LENGTH: 21
<212> TYPE: PRT
<213> ORGANISM: Homo sapiens

<400> SEQUENCE: 417

Met Arg Phe Val Val Ala Leu Val Leu Leu Asn Val Ala Ala Ala Gly
1               5                   10                  15

Ala Val Pro Leu Leu
            20

```
<210> SEQ ID NO 418
<211> LENGTH: 19
<212> TYPE: PRT
<213> ORGANISM: Homo sapiens

<400> SEQUENCE: 418

Met His Pro Gly Val Leu Ala Ala Phe Leu Phe Leu Ser Trp Thr His
1               5                   10                  15

Cys Arg Ala

<210> SEQ ID NO 419
<211> LENGTH: 20
<212> TYPE: PRT
<213> ORGANISM: Homo sapiens

<400> SEQUENCE: 419

Met Ser Glu Phe Leu Leu Ala Leu Leu Thr Leu Ser Gly Leu Leu Pro
1               5                   10                  15

Ile Ala Arg Val
            20

<210> SEQ ID NO 420
<211> LENGTH: 21
<212> TYPE: PRT
<213> ORGANISM: Homo sapiens

<400> SEQUENCE: 420

Met Asn Ala Lys Val Val Val Leu Val Leu Val Leu Thr Ala Leu
1               5                   10                  15

Cys Leu Ser Asp Gly
            20

<210> SEQ ID NO 421
<211> LENGTH: 20
<212> TYPE: PRT
<213> ORGANISM: Homo sapiens

<400> SEQUENCE: 421

Met Glu Thr Leu Gly Ala Leu Leu Val Leu Glu Phe Leu Leu Leu Ser
1               5                   10                  15

Pro Val Glu Ala
            20

<210> SEQ ID NO 422
<211> LENGTH: 21
<212> TYPE: PRT
<213> ORGANISM: Homo sapiens

<400> SEQUENCE: 422

Met Ala Ser Ser Leu Thr Cys Thr Gly Val Ile Trp Ala Leu Leu Ser
1               5                   10                  15

Phe Leu Cys Ala Ala
            20

<210> SEQ ID NO 423
<211> LENGTH: 21
<212> TYPE: PRT
<213> ORGANISM: Homo sapiens

<400> SEQUENCE: 423

Met Ala Val Gly Lys Phe Leu Leu Gly Ser Leu Leu Leu Leu Ser Leu
1               5                   10                  15
```

```
Gln Leu Gly Gln Gly
        20

<210> SEQ ID NO 424
<211> LENGTH: 19
<212> TYPE: PRT
<213> ORGANISM: Homo sapiens

<400> SEQUENCE: 424

Met Trp Gln Leu Leu Ala Ala Ala Cys Trp Met Leu Leu Leu Gly Ser
1               5                   10                  15

Met Tyr Gly

<210> SEQ ID NO 425
<211> LENGTH: 23
<212> TYPE: PRT
<213> ORGANISM: Homo sapiens

<400> SEQUENCE: 425

Met Gly Thr Gly Gly Ser Leu Leu Cys Gly Cys Ser Leu Val Leu Ser
1               5                   10                  15

Cys Leu Cys Pro Ser Ala Ser
        20

<210> SEQ ID NO 426
<211> LENGTH: 17
<212> TYPE: PRT
<213> ORGANISM: Homo sapiens

<400> SEQUENCE: 426

Met Trp Leu Tyr Leu Ala Ala Phe Val Gly Leu Tyr Tyr Leu Leu His
1               5                   10                  15

Trp

<210> SEQ ID NO 427
<211> LENGTH: 19
<212> TYPE: PRT
<213> ORGANISM: Homo sapiens

<400> SEQUENCE: 427

Met Asp Trp Thr Trp Arg Ile Leu Phe Leu Val Ala Ala Ala Thr Gly
1               5                   10                  15

Thr His Ala

<210> SEQ ID NO 428
<211> LENGTH: 21
<212> TYPE: PRT
<213> ORGANISM: Homo sapiens

<400> SEQUENCE: 428

Asp Leu Arg Val Ala Thr Val Thr Leu Met Leu Ala Ile Leu Ser Ser
1               5                   10                  15

Ser Leu Ala Glu Gly
        20

<210> SEQ ID NO 429
<211> LENGTH: 20
<212> TYPE: PRT
<213> ORGANISM: Homo sapiens

<400> SEQUENCE: 429

Met Gly Gly Arg Val Phe Leu Ala Phe Cys Val Trp Leu Thr Leu Pro
```

```
                1               5                  10                 15
Gly Ala Glu Thr
            20

<210> SEQ ID NO 430
<211> LENGTH: 19
<212> TYPE: PRT
<213> ORGANISM: Homo sapiens

<400> SEQUENCE: 430

Met Glu Phe Gly Leu Ser Trp Val Phe Leu Val Ala Leu Leu Arg Gly
1               5                  10                 15

Val Gln Cys

<210> SEQ ID NO 431
<211> LENGTH: 21
<212> TYPE: PRT
<213> ORGANISM: Homo sapiens

<400> SEQUENCE: 431

Met Arg Val Gly Gly Ala Phe His Leu Leu Val Cys Leu Ser Pro
1               5                  10                 15

Ala Leu Leu Ser Ala
            20

<210> SEQ ID NO 432
<211> LENGTH: 19
<212> TYPE: PRT
<213> ORGANISM: Homo sapiens

<400> SEQUENCE: 432

Met Ala Gln Ser Arg Val Leu Leu Leu Leu Leu Leu Pro Pro Gln
1               5                  10                 15

Leu His Leu

<210> SEQ ID NO 433
<211> LENGTH: 20
<212> TYPE: PRT
<213> ORGANISM: Homo sapiens

<400> SEQUENCE: 433

Met Ala Leu Arg Ala Pro Ala Leu Leu Pro Leu Leu Leu Leu Leu Leu
1               5                  10                 15

Pro Leu Arg Ala
            20

<210> SEQ ID NO 434
<211> LENGTH: 20
<212> TYPE: PRT
<213> ORGANISM: Homo sapiens

<400> SEQUENCE: 434

Met Asp Pro Lys Gly Leu Leu Ser Leu Thr Phe Val Leu Phe Leu Ser
1               5                  10                 15

Leu Ala Phe Gly
            20

<210> SEQ ID NO 435
<211> LENGTH: 18
<212> TYPE: PRT
<213> ORGANISM: Homo sapiens
```

```
<400> SEQUENCE: 435

Met Val Trp Arg Leu Val Leu Leu Ala Leu Trp Val Trp Pro Ser Thr
1               5                   10                  15

Gln Ala

<210> SEQ ID NO 436
<211> LENGTH: 20
<212> TYPE: PRT
<213> ORGANISM: Homo sapiens

<400> SEQUENCE: 436

Met Asp Leu Leu Trp Met Pro Leu Leu Val Ala Ala Cys Val Ser
1               5                   10                  15

Ala Val His Ser
            20

<210> SEQ ID NO 437
<211> LENGTH: 19
<212> TYPE: PRT
<213> ORGANISM: Homo sapiens

<400> SEQUENCE: 437

Met Lys Phe Leu Leu Asp Ile Leu Leu Leu Pro Leu Leu Ile Val
1               5                   10                  15

Cys Ser Leu

<210> SEQ ID NO 438
<211> LENGTH: 19
<212> TYPE: PRT
<213> ORGANISM: Homo sapiens

<400> SEQUENCE: 438

Met Asn Thr Leu Leu Leu Val Ser Leu Ser Phe Leu Tyr Leu Lys Glu
1               5                   10                  15

Val Met Gly

<210> SEQ ID NO 439
<211> LENGTH: 23
<212> TYPE: PRT
<213> ORGANISM: Homo sapiens

<400> SEQUENCE: 439

Met Ala Gly Val Arg Ala Arg Ala Pro Leu Pro Leu Ala Leu Leu Leu
1               5                   10                  15

Ser Leu Pro Ala Ala Pro Gly
            20

<210> SEQ ID NO 440
<211> LENGTH: 21
<212> TYPE: PRT
<213> ORGANISM: Homo sapiens

<400> SEQUENCE: 440

Met Leu Leu Pro Gln Leu Cys Trp Leu Pro Leu Leu Ala Gly Leu Leu
1               5                   10                  15

Pro Pro Val Pro Ala
            20

<210> SEQ ID NO 441
<211> LENGTH: 22
<212> TYPE: PRT
```

<213> ORGANISM: Homo sapiens

<400> SEQUENCE: 441

Met Gln Ile Pro Arg Ala Ala Leu Leu Pro Leu Leu Leu Leu Leu Leu
1               5                   10                  15

Ala Ala Pro Ala Ser Ala
            20

<210> SEQ ID NO 442
<211> LENGTH: 19
<212> TYPE: PRT
<213> ORGANISM: Homo sapiens

<400> SEQUENCE: 442

Met Arg Leu Leu Cys Gly Leu Trp Leu Trp Leu Ser Leu Leu Lys Val
1               5                   10                  15

Leu Gln Ala

<210> SEQ ID NO 443
<211> LENGTH: 21
<212> TYPE: PRT
<213> ORGANISM: Homo sapiens

<400> SEQUENCE: 443

Met Ser Leu Thr Val Val Ser Met Ala Cys Val Gly Phe Phe Leu Leu
1               5                   10                  15

Gln Gly Ala Trp Pro
            20

<210> SEQ ID NO 444
<211> LENGTH: 19
<212> TYPE: PRT
<213> ORGANISM: Homo sapiens

<400> SEQUENCE: 444

Met Lys Leu Leu Phe Pro Ile Phe Ala Ser Leu Met Leu Gln Tyr Gln
1               5                   10                  15

Val Asn Thr

<210> SEQ ID NO 445
<211> LENGTH: 23
<212> TYPE: PRT
<213> ORGANISM: Homo sapiens

<400> SEQUENCE: 445

Met Val Pro Ser Ala Gly Gln Leu Ala Leu Phe Ala Leu Gly Ile Val
1               5                   10                  15

Leu Ala Ala Cys Gln Ala Leu
            20

<210> SEQ ID NO 446
<211> LENGTH: 22
<212> TYPE: PRT
<213> ORGANISM: Homo sapiens

<400> SEQUENCE: 446

Met Leu Arg Leu Gly Leu Cys Ala Ala Ala Leu Leu Cys Val Cys Arg
1               5                   10                  15

Pro Gly Ala Val Arg Ala
            20

<210> SEQ ID NO 447
<211> LENGTH: 22
<212> TYPE: PRT
<213> ORGANISM: Homo sapiens

<400> SEQUENCE: 447

Met Thr Trp Lys Gly Gly Gly Gly Trp Met Ala Ala Val Thr His Gly
1               5                   10                  15

Pro Gly Ile Thr Trp Gly
            20

<210> SEQ ID NO 448
<211> LENGTH: 22
<212> TYPE: PRT
<213> ORGANISM: Homo sapiens

<400> SEQUENCE: 448

Met Gly Ser Leu Phe Pro Leu Ser Leu Leu Phe Phe Leu Ala Ala Ala
1               5                   10                  15

Tyr Pro Gly Val Gly Ser
            20

<210> SEQ ID NO 449
<211> LENGTH: 20
<212> TYPE: PRT
<213> ORGANISM: Homo sapiens

<400> SEQUENCE: 449

Met Lys Ser Tyr Thr Pro Tyr Phe Ile Leu Leu Trp Ser Ala Val Gly
1               5                   10                  15

Ile Ala Lys Ala
            20

<210> SEQ ID NO 450
<211> LENGTH: 21
<212> TYPE: PRT
<213> ORGANISM: Homo sapiens

<400> SEQUENCE: 450

Met Lys Gly Ile Cys Ser Asp Ala Ile Leu Val Leu Ala Thr Ser Met
1               5                   10                  15

Trp Met Ala Phe Ala
            20

<210> SEQ ID NO 451
<211> LENGTH: 21
<212> TYPE: PRT
<213> ORGANISM: Homo sapiens

<400> SEQUENCE: 451

Met Ser Pro Leu Leu Arg Arg Leu Leu Ala Leu Leu Gln Leu
1               5                   10                  15

Ala Pro Ala Gln Ala
            20

<210> SEQ ID NO 452
<211> LENGTH: 20
<212> TYPE: PRT
<213> ORGANISM: Homo sapiens

<400> SEQUENCE: 452

Met Val Phe Ser Leu Lys Val Ile Leu Phe Leu Ser Leu Leu Leu Ser
1               5                   10                  15

Pro Val Leu Lys
        20

<210> SEQ ID NO 453
<211> LENGTH: 20
<212> TYPE: PRT
<213> ORGANISM: Homo sapiens

<400> SEQUENCE: 453

Met Leu Met Leu Met Leu Val Ala Ala Val Thr Met Trp Leu Arg Pro
1               5                   10                  15

Leu Val Thr Ala
        20

<210> SEQ ID NO 454
<211> LENGTH: 22
<212> TYPE: PRT
<213> ORGANISM: Homo sapiens

<400> SEQUENCE: 454

Met Thr Ser Gln Arg Ser Pro Leu Ala Pro Leu Leu Leu Ser Leu
1               5                   10                  15

His Gly Val Ala Ala Ser
        20

<210> SEQ ID NO 455
<211> LENGTH: 22
<212> TYPE: PRT
<213> ORGANISM: Homo sapiens

<400> SEQUENCE: 455

Met Ala Ala Arg Gly Ser Gly Pro Arg Ala Leu Arg Leu Leu Leu Leu
1               5                   10                  15

Val Gln Leu Val Ala Gly
        20

<210> SEQ ID NO 456
<211> LENGTH: 22
<212> TYPE: PRT
<213> ORGANISM: Homo sapiens

<400> SEQUENCE: 456

Met Leu Gly Ala Arg Ala Trp Leu Gly Arg Val Leu Leu Leu Pro Arg
1               5                   10                  15

Ala Gly Ala Gly Leu Ala
        20

<210> SEQ ID NO 457
<211> LENGTH: 21
<212> TYPE: PRT
<213> ORGANISM: Homo sapiens

<400> SEQUENCE: 457

Met Arg Leu Leu Ile Leu Ala Leu Leu Gly Ile Cys Ser Leu Thr Ala
1               5                   10                  15

Tyr Ile Val Glu Gly
        20

<210> SEQ ID NO 458
<211> LENGTH: 22
<212> TYPE: PRT
<213> ORGANISM: Homo sapiens

```
<400> SEQUENCE: 458

Met Pro Leu Ser Ser His Leu Leu Pro Ala Leu Val Leu Phe Leu Ala
1               5                   10                  15

Gly Ser Ser Gly Trp Ala
            20

<210> SEQ ID NO 459
<211> LENGTH: 22
<212> TYPE: PRT
<213> ORGANISM: Homo sapiens

<400> SEQUENCE: 459

Met Ala Leu Ala Ala Leu Met Ile Ala Leu Gly Ser Leu Gly Leu His
1               5                   10                  15

Thr Trp Gln Ala Gln Ala
            20

<210> SEQ ID NO 460
<211> LENGTH: 20
<212> TYPE: PRT
<213> ORGANISM: Homo sapiens

<400> SEQUENCE: 460

Met Pro Arg Gly Phe Thr Trp Leu Arg Tyr Leu Gly Ile Phe Leu Gly
1               5                   10                  15

Val Ala Leu Gly
            20

<210> SEQ ID NO 461
<211> LENGTH: 23
<212> TYPE: PRT
<213> ORGANISM: Homo sapiens

<400> SEQUENCE: 461

Met Ser Leu Ala Ser Gly Pro Gly Pro Gly Trp Leu Leu Phe Ser Phe
1               5                   10                  15

Gly Met Gly Leu Val Ser Gly
            20

<210> SEQ ID NO 462
<211> LENGTH: 20
<212> TYPE: PRT
<213> ORGANISM: Homo sapiens

<400> SEQUENCE: 462

Met Lys Met His Leu Gln Arg Ala Leu Val Val Leu Ala Leu Leu Asn
1               5                   10                  15

Phe Ala Thr Val
            20

<210> SEQ ID NO 463
<211> LENGTH: 22
<212> TYPE: PRT
<213> ORGANISM: Homo sapiens

<400> SEQUENCE: 463

Met Lys Ile Ala Thr Val Ser Val Leu Leu Pro Leu Ala Leu Cys Leu
1               5                   10                  15

Ile Gln Asp Ala Ala Ser
            20
```

<210> SEQ ID NO 464
<211> LENGTH: 21
<212> TYPE: PRT
<213> ORGANISM: Homo sapiens

<400> SEQUENCE: 464

Met Lys Leu Ser Val Cys Leu Leu Leu Val Thr Ala Leu Cys Cys
1               5                   10                  15
Tyr Gln Ala Asn Ala
            20

<210> SEQ ID NO 465
<211> LENGTH: 23
<212> TYPE: PRT
<213> ORGANISM: Homo sapiens

<400> SEQUENCE: 465

Met Pro Pro Trp Gly Ala Ala Leu Ala Leu Ile Leu Ala Val Leu Ala
1               5                   10                  15
Leu Leu Gly Leu Leu Gly Pro
            20

<210> SEQ ID NO 466
<211> LENGTH: 20
<212> TYPE: PRT
<213> ORGANISM: Homo sapiens

<400> SEQUENCE: 466

Met Ser Gly Asn Trp Val His Pro Gly Gln Ile Leu Ile Trp Ala Ile
1               5                   10                  15
Trp Val Leu Ala
            20

<210> SEQ ID NO 467
<211> LENGTH: 20
<212> TYPE: PRT
<213> ORGANISM: Homo sapiens

<400> SEQUENCE: 467

Met Arg Arg Trp Ala Trp Ala Ala Val Val Leu Leu Gly Pro Gln
1               5                   10                  15
Leu Val Leu Leu
            20

<210> SEQ ID NO 468
<211> LENGTH: 19
<212> TYPE: PRT
<213> ORGANISM: Homo sapiens

<400> SEQUENCE: 468

Met Arg Leu Pro Asp Val Gln Leu Trp Leu Val Leu Leu Trp Ala Leu
1               5                   10                  15
Val Arg Ala

<210> SEQ ID NO 469
<211> LENGTH: 22
<212> TYPE: PRT
<213> ORGANISM: Homo sapiens

<400> SEQUENCE: 469

Met Arg Cys Ala Leu Ala Leu Ser Ala Leu Leu Leu Leu Leu Ser Thr
1               5                   10                  15

Pro Pro Leu Leu Pro Ser
            20

<210> SEQ ID NO 470
<211> LENGTH: 20
<212> TYPE: PRT
<213> ORGANISM: Homo sapiens

<400> SEQUENCE: 470

Met Asp Trp Pro His Asn Leu Leu Phe Leu Leu Thr Ile Ser Ile Phe
1               5                   10                  15

Leu Gly Leu Gly
            20

<210> SEQ ID NO 471
<211> LENGTH: 22
<212> TYPE: PRT
<213> ORGANISM: Homo sapiens

<400> SEQUENCE: 471

Met Thr Ala Arg Gly Leu Ala Leu Gly Leu Leu Leu Leu Leu Leu Cys
1               5                   10                  15

Pro Ala Gln Val Phe Ser
            20

<210> SEQ ID NO 472
<211> LENGTH: 21
<212> TYPE: PRT
<213> ORGANISM: Homo sapiens

<400> SEQUENCE: 472

Met Asn Cys Val Cys Arg Leu Val Leu Val Val Leu Ser Leu Trp Pro
1               5                   10                  15

Asp Thr Ala Val Ala
            20

<210> SEQ ID NO 473
<211> LENGTH: 21
<212> TYPE: PRT
<213> ORGANISM: Homo sapiens

<400> SEQUENCE: 473

Met Ser Arg Ser Ala Thr Leu Leu Leu Cys Leu Leu Gly Cys His Val
1               5                   10                  15

Trp Lys Ala Val Thr
            20

<210> SEQ ID NO 474
<211> LENGTH: 22
<212> TYPE: PRT
<213> ORGANISM: Homo sapiens

<400> SEQUENCE: 474

Met Ala Thr Trp Ala Leu Leu Leu Leu Ala Ala Met Leu Leu Gly Asn
1               5                   10                  15

Pro Gly Leu Val Phe Ser
            20

<210> SEQ ID NO 475
<211> LENGTH: 23
<212> TYPE: PRT
<213> ORGANISM: Homo sapiens

<400> SEQUENCE: 475

Met Pro Ser Trp Ile Gly Ala Val Ile Leu Pro Leu Leu Gly Leu Leu
1               5                   10                  15

Leu Ser Leu Pro Ala Gly Ala
            20

<210> SEQ ID NO 476
<211> LENGTH: 25
<212> TYPE: PRT
<213> ORGANISM: Homo sapiens

<400> SEQUENCE: 476

Met Ala Gly Arg Gly Gly Ser Ala Leu Leu Ala Leu Cys Gly Ala Leu
1               5                   10                  15

Ala Ala Cys Gly Trp Leu Leu Gly Ala
            20                  25

<210> SEQ ID NO 477
<211> LENGTH: 20
<212> TYPE: PRT
<213> ORGANISM: Homo sapiens

<400> SEQUENCE: 477

Met Pro Leu Trp Val Phe Phe Phe Val Ile Leu Thr Leu Ser Asn Ser
1               5                   10                  15

Ser His Cys Ser
            20

<210> SEQ ID NO 478
<211> LENGTH: 22
<212> TYPE: PRT
<213> ORGANISM: Homo sapiens

<400> SEQUENCE: 478

Met Val Gly Gln Arg Val Leu Leu Leu Val Ala Phe Leu Leu Ser Gly
1               5                   10                  15

Val Leu Leu Ser Glu Ala
            20

<210> SEQ ID NO 479
<211> LENGTH: 19
<212> TYPE: PRT
<213> ORGANISM: Homo sapiens

<400> SEQUENCE: 479

Met Val Leu Leu His Trp Cys Leu Leu Trp Leu Leu Phe Pro Leu Ser
1               5                   10                  15

Ser Arg Thr

<210> SEQ ID NO 480
<211> LENGTH: 24
<212> TYPE: PRT
<213> ORGANISM: Homo sapiens

<400> SEQUENCE: 480

Met Val Pro Gly Val Pro Gly Ala Val Leu Thr Leu Cys Leu Trp Leu
1               5                   10                  15

Ala Ala Ser Ser Gly Cys Leu Ala
            20

```
<210> SEQ ID NO 481
<211> LENGTH: 21
<212> TYPE: PRT
<213> ORGANISM: Homo sapiens

<400> SEQUENCE: 481

Met Asn Arg Phe Leu Leu Leu Met Ser Leu Tyr Leu Leu Gly Ser Ala
1               5                   10                  15

Arg Gly Thr Ser Ser
            20

<210> SEQ ID NO 482
<211> LENGTH: 24
<212> TYPE: PRT
<213> ORGANISM: Homo sapiens

<400> SEQUENCE: 482

Met Glu Ala Ala Val Ala Ala Pro Arg Pro Arg Leu Leu Leu Leu Val
1               5                   10                  15

Leu Ala Ala Ala Ala Ala Ala Ala
            20

<210> SEQ ID NO 483
<211> LENGTH: 22
<212> TYPE: PRT
<213> ORGANISM: Homo sapiens

<400> SEQUENCE: 483

Met Gly Arg Leu Val Leu Leu Trp Gly Ala Ala Val Phe Leu Leu Gly
1               5                   10                  15

Gly Trp Met Ala Leu Gly
            20

<210> SEQ ID NO 484
<211> LENGTH: 23
<212> TYPE: PRT
<213> ORGANISM: Homo sapiens

<400> SEQUENCE: 484

Met Ala Ala Trp Gly Cys Val Ala Ala Leu Gly Ala Ala Arg Gly Leu
1               5                   10                  15

Cys Trp Arg Ala Ala Arg Ala
            20

<210> SEQ ID NO 485
<211> LENGTH: 20
<212> TYPE: PRT
<213> ORGANISM: Homo sapiens

<400> SEQUENCE: 485

Met Glu Ala Leu Thr Leu Trp Leu Leu Pro Trp Ile Cys Gln Cys Val
1               5                   10                  15

Ser Val Arg Ala
            20

<210> SEQ ID NO 486
<211> LENGTH: 22
<212> TYPE: PRT
<213> ORGANISM: Homo sapiens

<400> SEQUENCE: 486

Met Ile His Gly Arg Ser Val Leu His Ile Val Ala Ser Leu Ile Ile
1               5                   10                  15
```

Leu His Leu Ser Gly Ala
            20

<210> SEQ ID NO 487
<211> LENGTH: 21
<212> TYPE: PRT
<213> ORGANISM: Homo sapiens

<400> SEQUENCE: 487

Met Ile Ile Lys His Phe Phe Gly Thr Val Leu Val Leu Leu Ala Ser
1               5                   10                  15

Thr Thr Ile Phe Ser
            20

<210> SEQ ID NO 488
<211> LENGTH: 24
<212> TYPE: PRT
<213> ORGANISM: Homo sapiens

<400> SEQUENCE: 488

Met Pro Ala Ala Met Leu Pro Tyr Ala Cys Val Leu Val Leu Leu Gly
1               5                   10                  15

Ala His Thr Ala Pro Ala Ala Gly
            20

<210> SEQ ID NO 489
<211> LENGTH: 20
<212> TYPE: PRT
<213> ORGANISM: Homo sapiens

<400> SEQUENCE: 489

Met Arg Ile Ile Ser Arg Gln Ile Val Leu Leu Phe Ser Gly Phe Trp
1               5                   10                  15

Gly Leu Ala Met
            20

<210> SEQ ID NO 490
<211> LENGTH: 22
<212> TYPE: PRT
<213> ORGANISM: Homo sapiens

<400> SEQUENCE: 490

Met Gly Ser Pro Arg Ser Ala Leu Ser Cys Leu Leu Leu His Leu Leu
1               5                   10                  15

Val Leu Cys Leu Gln Ala
            20

<210> SEQ ID NO 491
<211> LENGTH: 21
<212> TYPE: PRT
<213> ORGANISM: Homo sapiens

<400> SEQUENCE: 491

Met Thr Asp Lys Ser Ile Val Ile Leu Ser Leu Met Val Phe His Ser
1               5                   10                  15

Ser Phe Ile Asn Gly
            20

<210> SEQ ID NO 492
<211> LENGTH: 21
<212> TYPE: PRT
<213> ORGANISM: Homo sapiens

<400> SEQUENCE: 492

Met Pro Phe Arg Leu Leu Ile Pro Leu Gly Leu Leu Cys Ala Leu Leu
1               5                   10                  15

Pro Gln His His Gly
            20

<210> SEQ ID NO 493
<211> LENGTH: 21
<212> TYPE: PRT
<213> ORGANISM: Homo sapiens

<400> SEQUENCE: 493

Met Ser Leu Met Val Val Ser Met Ala Arg Val Gly Phe Phe Leu Leu
1               5                   10                  15

Gln Gly Ala Trp Pro
            20

<210> SEQ ID NO 494
<211> LENGTH: 21
<212> TYPE: PRT
<213> ORGANISM: Homo sapiens

<400> SEQUENCE: 494

Met Asp Ser Trp Thr Phe Cys Cys Val Ser Leu Cys Ile Leu Val Ala
1               5                   10                  15

Lys His Thr Asp Ala
            20

<210> SEQ ID NO 495
<211> LENGTH: 22
<212> TYPE: PRT
<213> ORGANISM: Homo sapiens

<400> SEQUENCE: 495

Met Ala Gly Ala Ser Arg Leu Leu Phe Leu Trp Leu Gly Cys Phe Cys
1               5                   10                  15

Val Ser Leu Ala Gln Gly
            20

<210> SEQ ID NO 496
<211> LENGTH: 21
<212> TYPE: PRT
<213> ORGANISM: Homo sapiens

<400> SEQUENCE: 496

Met Glu Ala Ser Arg Trp Trp Leu Leu Val Thr Val Leu Met Ala Gly
1               5                   10                  15

Ala His Cys Val Ala
            20

<210> SEQ ID NO 497
<211> LENGTH: 21
<212> TYPE: PRT
<213> ORGANISM: Homo sapiens

<400> SEQUENCE: 497

Met Asp Pro Lys Gln Thr Thr Leu Leu Cys Leu Val Leu Cys Leu Gly
1               5                   10                  15

Gln Arg Ile Gln Ala
            20

<210> SEQ ID NO 498
<211> LENGTH: 21
<212> TYPE: PRT
<213> ORGANISM: Homo sapiens

<400> SEQUENCE: 498

Met Lys Leu Leu Tyr Leu Phe Leu Ala Ile Leu Ala Ile Glu Glu
1               5                   10                  15

Pro Val Ile Ser Gly
            20

<210> SEQ ID NO 499
<211> LENGTH: 21
<212> TYPE: PRT
<213> ORGANISM: Homo sapiens

<400> SEQUENCE: 499

Met Arg Trp Cys Leu Leu Ile Trp Ala Gln Gly Leu Arg Gln Ala
1               5                   10                  15

Pro Leu Ala Ser Gly
            20

<210> SEQ ID NO 500
<211> LENGTH: 21
<212> TYPE: PRT
<213> ORGANISM: Homo sapiens

<400> SEQUENCE: 500

Met Arg Leu Arg Leu Arg Leu Leu Ala Leu Leu Leu Leu Leu Ala
1               5                   10                  15

Pro Pro Ala Arg Ala
            20

<210> SEQ ID NO 501
<211> LENGTH: 23
<212> TYPE: PRT
<213> ORGANISM: Homo sapiens

<400> SEQUENCE: 501

Met Ala Ser His Ser Gly Pro Ser Thr Ser Val Leu Phe Leu Phe Cys
1               5                   10                  15

Cys Leu Gly Gly Trp Leu Ala
            20

<210> SEQ ID NO 502
<211> LENGTH: 25
<212> TYPE: PRT
<213> ORGANISM: Homo sapiens

<400> SEQUENCE: 502

Met Asp Arg Gly Pro Ala Ala Val Ala Cys Thr Leu Leu Leu Ala Leu
1               5                   10                  15

Val Ala Cys Leu Ala Pro Ala Ser Gly
            20                  25

<210> SEQ ID NO 503
<211> LENGTH: 21
<212> TYPE: PRT
<213> ORGANISM: Homo sapiens

<400> SEQUENCE: 503

Met Arg Phe Ala Trp Thr Val Leu Leu Leu Gly Pro Leu Gln Leu Cys

```
1               5                   10                  15

Ala Leu Val His Cys
            20

<210> SEQ ID NO 504
<211> LENGTH: 20
<212> TYPE: PRT
<213> ORGANISM: Homo sapiens

<400> SEQUENCE: 504

Met Arg Gly Phe Asn Leu Leu Phe Trp Gly Cys Cys Val Met His
1               5                   10                  15

Ser Trp Glu Gly
            20

<210> SEQ ID NO 505
<211> LENGTH: 22
<212> TYPE: PRT
<213> ORGANISM: Homo sapiens

<400> SEQUENCE: 505

Met Asn Leu Arg Leu Cys Val Gln Ala Leu Leu Leu Trp Leu Ser
1               5                   10                  15

Leu Thr Ala Val Cys Gly
            20

<210> SEQ ID NO 506
<211> LENGTH: 24
<212> TYPE: PRT
<213> ORGANISM: Homo sapiens

<400> SEQUENCE: 506

Met Pro Gly Pro Trp Leu Leu Leu Ala Leu Ala Leu Thr Leu Asn Leu
1               5                   10                  15

Thr Gly Val Pro Gly Gly Arg Ala
            20

<210> SEQ ID NO 507
<211> LENGTH: 25
<212> TYPE: PRT
<213> ORGANISM: Homo sapiens

<400> SEQUENCE: 507

Met Ala Gly Gly Ser Ala Thr Thr Trp Gly Tyr Pro Val Ala Leu Leu
1               5                   10                  15

Leu Leu Val Ala Thr Leu Gly Leu Gly
            20                  25

<210> SEQ ID NO 508
<211> LENGTH: 21
<212> TYPE: PRT
<213> ORGANISM: Homo sapiens

<400> SEQUENCE: 508

Met Glu Cys Leu Tyr Tyr Phe Leu Gly Phe Leu Leu Leu Ala Ala Arg
1               5                   10                  15

Leu Pro Leu Asp Ala
            20

<210> SEQ ID NO 509
<211> LENGTH: 21
<212> TYPE: PRT
```

<213> ORGANISM: Homo sapiens

<400> SEQUENCE: 509

Met Lys Met Arg Phe Leu Gly Leu Val Val Cys Leu Val Leu Trp Thr
1               5                   10                  15

Leu His Ser Glu Gly
            20

<210> SEQ ID NO 510
<211> LENGTH: 23
<212> TYPE: PRT
<213> ORGANISM: Homo sapiens

<400> SEQUENCE: 510

Met Lys Gly Arg Gly Met Leu Val Leu Leu His Ala Val Val Leu
1               5                   10                  15

Gly Leu Pro Ser Ala Trp Ala
            20

<210> SEQ ID NO 511
<211> LENGTH: 23
<212> TYPE: PRT
<213> ORGANISM: Homo sapiens

<400> SEQUENCE: 511

Met Thr Pro Ile Leu Thr Val Leu Ile Cys Leu Gly Leu Ser Leu Gly
1               5                   10                  15

Pro Arg Thr His Val Gln Ala
            20

<210> SEQ ID NO 512
<211> LENGTH: 23
<212> TYPE: PRT
<213> ORGANISM: Homo sapiens

<400> SEQUENCE: 512

Met Thr Pro Ile Leu Thr Val Leu Ile Cys Leu Gly Leu Ser Leu Gly
1               5                   10                  15

Pro Arg Thr His Val Gln Ala
            20

<210> SEQ ID NO 513
<211> LENGTH: 22
<212> TYPE: PRT
<213> ORGANISM: Homo sapiens

<400> SEQUENCE: 513

Met Lys Asp Met Pro Leu Arg Ile His Val Leu Leu Gly Leu Ala Ile
1               5                   10                  15

Thr Thr Leu Val Gln Ala
            20

<210> SEQ ID NO 514
<211> LENGTH: 24
<212> TYPE: PRT
<213> ORGANISM: Homo sapiens

<400> SEQUENCE: 514

Met Thr Cys Trp Leu Cys Val Leu Ser Leu Pro Leu Leu Leu Leu Pro
1               5                   10                  15

Ala Ala Pro Pro Pro Ala Gly Gly
            20

<210> SEQ ID NO 515
<211> LENGTH: 24
<212> TYPE: PRT
<213> ORGANISM: Homo sapiens

<400> SEQUENCE: 515

Met Arg Ser Arg Leu Pro Pro Ala Leu Ala Ala Leu Gly Ala Ala Leu
1               5                   10                  15

Leu Leu Ser Ser Ile Glu Ala Glu
            20

<210> SEQ ID NO 516
<211> LENGTH: 24
<212> TYPE: PRT
<213> ORGANISM: Homo sapiens

<400> SEQUENCE: 516

Met Glu Gln Arg Pro Arg Gly Cys Ala Ala Val Ala Ala Ala Leu Leu
1               5                   10                  15

Leu Val Leu Leu Gly Ala Arg Ala
            20

<210> SEQ ID NO 517
<211> LENGTH: 23
<212> TYPE: PRT
<213> ORGANISM: Homo sapiens

<400> SEQUENCE: 517

Met Ser Arg Leu Ser Arg Ser Leu Leu Trp Ala Ala Thr Cys Leu Gly
1               5                   10                  15

Val Leu Cys Val Leu Ser Ala
            20

<210> SEQ ID NO 518
<211> LENGTH: 25
<212> TYPE: PRT
<213> ORGANISM: Homo sapiens

<400> SEQUENCE: 518

Met Val Cys Ser Ala Ala Pro Leu Leu Leu Ala Thr Thr Leu Pro
1               5                   10                  15

Leu Leu Gly Ser Pro Val Ala Gln Ala
            20                  25

<210> SEQ ID NO 519
<211> LENGTH: 22
<212> TYPE: PRT
<213> ORGANISM: Homo sapiens

<400> SEQUENCE: 519

Met Ile Leu Asn Trp Lys Leu Leu Gly Ile Leu Val Leu Cys Leu His
1               5                   10                  15

Thr Arg Gly Ile Ser Gly
            20

<210> SEQ ID NO 520
<211> LENGTH: 23
<212> TYPE: PRT
<213> ORGANISM: Homo sapiens

<400> SEQUENCE: 520

Met Ala Pro Tyr Pro Cys Gly Cys His Ile Leu Leu Leu Phe Cys
1               5                   10                  15

Cys Leu Ala Ala Ala Arg Ala
            20

<210> SEQ ID NO 521
<211> LENGTH: 20
<212> TYPE: PRT
<213> ORGANISM: Homo sapiens

<400> SEQUENCE: 521

Met Ile Ile Met Val Ile Ile Phe Leu Val Leu Leu Phe Trp Glu Asn
1               5                   10                  15

Glu Val Asn Asp
            20

<210> SEQ ID NO 522
<211> LENGTH: 22
<212> TYPE: PRT
<213> ORGANISM: Homo sapiens

<400> SEQUENCE: 522

Met Lys Leu His Ser Leu Ile Ser Val Leu Leu Leu Phe Val Thr Leu
1               5                   10                  15

Ile Pro Lys Gly Lys Thr
            20

<210> SEQ ID NO 523
<211> LENGTH: 22
<212> TYPE: PRT
<213> ORGANISM: Homo sapiens

<400> SEQUENCE: 523

Met Ile Met Phe Pro Leu Phe Gly Lys Ile Ser Leu Gly Ile Leu Ile
1               5                   10                  15

Phe Val Leu Ile Glu Gly
            20

<210> SEQ ID NO 524
<211> LENGTH: 23
<212> TYPE: PRT
<213> ORGANISM: Homo sapiens

<400> SEQUENCE: 524

Met Thr Pro Ile Leu Thr Val Leu Ile Cys Leu Gly Leu Ser Leu Gly
1               5                   10                  15

Pro Arg Thr Arg Val Gln Ala
            20

<210> SEQ ID NO 525
<211> LENGTH: 22
<212> TYPE: PRT
<213> ORGANISM: Homo sapiens

<400> SEQUENCE: 525

Met Ala Lys Pro Arg Leu Leu Val Leu Tyr Phe Ala Leu Ile Val Val
1               5                   10                  15

Pro Ala Trp Val Ser Ser
            20

<210> SEQ ID NO 526
<211> LENGTH: 23

```
<212> TYPE: PRT
<213> ORGANISM: Homo sapiens

<400> SEQUENCE: 526

Met Glu Lys Met Leu Ala Gly Cys Phe Leu Leu Ile Leu Gly Gln Ile
1               5                   10                  15

Val Leu Leu Pro Ala Glu Ala
            20

<210> SEQ ID NO 527
<211> LENGTH: 22
<212> TYPE: PRT
<213> ORGANISM: Homo sapiens

<400> SEQUENCE: 527

Met Glu Leu Pro Phe Val Thr His Leu Phe Leu Pro Leu Val Phe Leu
1               5                   10                  15

Thr Gly Leu Cys Ser Pro
            20

<210> SEQ ID NO 528
<211> LENGTH: 23
<212> TYPE: PRT
<213> ORGANISM: Homo sapiens

<400> SEQUENCE: 528

Met Lys Ile Cys Ser Leu Thr Leu Leu Ser Phe Leu Leu Leu Ala Ala
1               5                   10                  15

Gln Val Leu Leu Val Glu Gly
            20

<210> SEQ ID NO 529
<211> LENGTH: 25
<212> TYPE: PRT
<213> ORGANISM: Homo sapiens

<400> SEQUENCE: 529

Met Gln Arg Leu Met Met Leu Leu Ala Thr Ser Gly Ala Cys Leu Gly
1               5                   10                  15

Leu Leu Ala Val Ala Ala Val Ala Ala
            20                  25

<210> SEQ ID NO 530
<211> LENGTH: 25
<212> TYPE: PRT
<213> ORGANISM: Homo sapiens

<400> SEQUENCE: 530

Met Arg Gly Ala Ala Arg Leu Gly Arg Pro Gly Arg Ser Cys Leu Pro
1               5                   10                  15

Gly Pro Ala Leu Arg Ala Ala Ala Ala
            20                  25

<210> SEQ ID NO 531
<211> LENGTH: 22
<212> TYPE: PRT
<213> ORGANISM: Homo sapiens

<400> SEQUENCE: 531

Met Glu Arg Ile Val Ile Cys Leu Met Val Ile Phe Leu Gly Thr Leu
1               5                   10                  15

Val His Lys Ser Ser Ser
```

<210> SEQ ID NO 532
<211> LENGTH: 23
<212> TYPE: PRT
<213> ORGANISM: Homo sapiens

<400> SEQUENCE: 532

Met Gly Arg His Val Ala Thr Ser Cys His Val Ala Trp Leu Leu Val
1               5                   10                  15

Leu Ile Ser Gly Cys Trp Gly
            20

<210> SEQ ID NO 533
<211> LENGTH: 23
<212> TYPE: PRT
<213> ORGANISM: Homo sapiens

<400> SEQUENCE: 533

Met Leu Leu Trp Val Gln Gln Ala Leu Leu Ala Leu Leu Leu Pro Thr
1               5                   10                  15

Leu Leu Ala Gln Gly Glu Ala
            20

<210> SEQ ID NO 534
<211> LENGTH: 22
<212> TYPE: PRT
<213> ORGANISM: Homo sapiens

<400> SEQUENCE: 534

Met Arg Arg Arg Leu Trp Leu Gly Leu Ala Trp Leu Leu Leu Ala Arg
1               5                   10                  15

Ala Pro Asp Ala Ala Gly
            20

<210> SEQ ID NO 535
<211> LENGTH: 20
<212> TYPE: PRT
<213> ORGANISM: Homo sapiens

<400> SEQUENCE: 535

Met Arg Lys Thr Arg Leu Trp Gly Leu Leu Trp Met Leu Phe Val Ser
1               5                   10                  15

Glu Leu Arg Ala
            20

<210> SEQ ID NO 536
<211> LENGTH: 21
<212> TYPE: PRT
<213> ORGANISM: Homo sapiens

<400> SEQUENCE: 536

Met Lys Phe Tyr Ser Leu Leu Leu Cys Ser Leu Leu Phe Ser Phe Pro
1               5                   10                  15

Phe Leu Cys His Pro
            20

<210> SEQ ID NO 537
<211> LENGTH: 25
<212> TYPE: PRT
<213> ORGANISM: Homo sapiens

<400> SEQUENCE: 537

```
Met Ala Val Glu Ser Gln Gly Gly Arg Pro Leu Val Leu Gly Leu Leu
1               5                   10                  15

Leu Cys Val Leu Gly Pro Val Val Ser
            20                  25

<210> SEQ ID NO 538
<211> LENGTH: 26
<212> TYPE: PRT
<213> ORGANISM: Homo sapiens

<400> SEQUENCE: 538

Met Ala Ala Ala Thr Arg Gly Cys Arg Pro Trp Gly Ser Leu Leu Gly
1               5                   10                  15

Leu Leu Gly Leu Val Ser Ala Ala Ala Ala
            20                  25

<210> SEQ ID NO 539
<211> LENGTH: 26
<212> TYPE: PRT
<213> ORGANISM: Homo sapiens

<400> SEQUENCE: 539

Met Ala Ala Ala Thr Arg Gly Cys Arg Pro Trp Gly Ser Leu Leu Gly
1               5                   10                  15

Leu Leu Gly Leu Val Ser Ala Ala Ala Ala
            20                  25

<210> SEQ ID NO 540
<211> LENGTH: 25
<212> TYPE: PRT
<213> ORGANISM: Homo sapiens

<400> SEQUENCE: 540

Met Gly Ala Pro Ser Ala Cys Arg Thr Leu Val Leu Ala Leu Ala Ala
1               5                   10                  15

Met Leu Val Val Pro Gln Ala Glu Thr
            20                  25

<210> SEQ ID NO 541
<211> LENGTH: 24
<212> TYPE: PRT
<213> ORGANISM: Homo sapiens

<400> SEQUENCE: 541

Met Ala Gly Leu Gly Ala Ser Leu His Val Trp Gly Trp Leu Met Leu
1               5                   10                  15

Gly Ser Cys Leu Leu Ala Arg Ala
            20

<210> SEQ ID NO 542
<211> LENGTH: 24
<212> TYPE: PRT
<213> ORGANISM: Homo sapiens

<400> SEQUENCE: 542

Met Ala Ser Leu Gly Gln Ile Leu Phe Trp Ser Ile Ile Ser Ile Ile
1               5                   10                  15

Ile Ile Leu Ala Gly Ala Ile Ala
            20

<210> SEQ ID NO 543
```

```
<211> LENGTH: 23
<212> TYPE: PRT
<213> ORGANISM: Homo sapiens

<400> SEQUENCE: 543

Met Gly Gln Leu Cys Trp Leu Pro Leu Leu Ala Pro Leu Leu Leu Leu
1               5                   10                  15

Arg Pro Pro Gly Val Gln Ser
            20

<210> SEQ ID NO 544
<211> LENGTH: 21
<212> TYPE: PRT
<213> ORGANISM: Homo sapiens

<400> SEQUENCE: 544

Met Cys Leu Thr Asp Glu Trp Gly Phe Leu Phe Phe Phe Phe Phe Leu
1               5                   10                  15

Gly Val Pro Glu Ala
            20

<210> SEQ ID NO 545
<211> LENGTH: 22
<212> TYPE: PRT
<213> ORGANISM: Homo sapiens

<400> SEQUENCE: 545

Met Arg Thr His Thr Arg Gly Ala Pro Ser Val Phe Phe Ile Tyr Leu
1               5                   10                  15

Leu Cys Phe Val Ser Ala
            20

<210> SEQ ID NO 546
<211> LENGTH: 23
<212> TYPE: PRT
<213> ORGANISM: Homo sapiens

<400> SEQUENCE: 546

Met Ser Asp Leu Leu Ser Ile Tyr Ser Ala Pro Val Val Ser Thr
1               5                   10                  15

Val Leu His Met Leu Gln Ile
            20

<210> SEQ ID NO 547
<211> LENGTH: 22
<212> TYPE: PRT
<213> ORGANISM: Homo sapiens

<400> SEQUENCE: 547

Met Phe Leu Ser Lys Pro Ser Val Tyr Ile Cys Leu Phe Thr Cys Val
1               5                   10                  15

Leu Gln Leu Ser His Ser
            20

<210> SEQ ID NO 548
<211> LENGTH: 22
<212> TYPE: PRT
<213> ORGANISM: Homo sapiens

<400> SEQUENCE: 548

Met Arg Leu His Leu Leu Leu Leu Ile Leu Leu Leu Phe Ser Ile Leu
1               5                   10                  15
```

Leu Ser Pro Val Arg Gly
            20

<210> SEQ ID NO 549
<211> LENGTH: 24
<212> TYPE: PRT
<213> ORGANISM: Homo sapiens

<400> SEQUENCE: 549

Met Leu Ser Gln Leu Ala Met Leu Gln Gly Ser Leu Leu Val Val
1               5                   10                  15

Ala Thr Met Ser Val Ala Gln Gln
            20

<210> SEQ ID NO 550
<211> LENGTH: 25
<212> TYPE: PRT
<213> ORGANISM: Homo sapiens

<400> SEQUENCE: 550

Met Pro Ala Gly Val Pro Met Ser Thr Tyr Leu Lys Met Phe Ala Ala
1               5                   10                  15

Ser Leu Leu Ala Met Cys Ala Gly Ala
            20                  25

<210> SEQ ID NO 551
<211> LENGTH: 22
<212> TYPE: PRT
<213> ORGANISM: Homo sapiens

<400> SEQUENCE: 551

Met Asp Leu Trp Asn Leu Ser Trp Phe Leu Phe Leu Asp Ala Leu Leu
1               5                   10                  15

Val Ile Ser Gly Leu Ala
            20

<210> SEQ ID NO 552
<211> LENGTH: 26
<212> TYPE: PRT
<213> ORGANISM: Homo sapiens

<400> SEQUENCE: 552

Met Gly Leu Ser Ala Ala Ala Pro Leu Trp Gly Pro Pro Gly Leu Leu
1               5                   10                  15

Leu Ala Ile Ala Leu His Pro Ala Leu Ser
            20                  25

<210> SEQ ID NO 553
<211> LENGTH: 25
<212> TYPE: PRT
<213> ORGANISM: Homo sapiens

<400> SEQUENCE: 553

Met Trp Gly Leu Ala Gly Gly Arg Leu Phe Gly Ile Phe Ser Ala Pro
1               5                   10                  15

Val Leu Val Ala Val Val Cys Cys Ala
            20                  25

<210> SEQ ID NO 554
<211> LENGTH: 24
<212> TYPE: PRT
<213> ORGANISM: Homo sapiens

```
<400> SEQUENCE: 554

Met Arg Val Ala Gly Ala Ala Lys Leu Val Ala Val Ala Val Phe
1               5                   10                  15

Leu Leu Thr Phe Tyr Val Ile Ser
            20

<210> SEQ ID NO 555
<211> LENGTH: 22
<212> TYPE: PRT
<213> ORGANISM: Homo sapiens

<400> SEQUENCE: 555

Met Asp Met Arg Val Pro Ala Gln Leu Leu Gly Leu Leu Leu Leu Trp
1               5                   10                  15

Leu Pro Gly Val Arg Phe
            20

<210> SEQ ID NO 556
<211> LENGTH: 25
<212> TYPE: PRT
<213> ORGANISM: Homo sapiens

<400> SEQUENCE: 556

Met His Leu Ala Arg Leu Val Gly Ser Cys Ser Leu Leu Leu Leu Leu
1               5                   10                  15

Gly Ala Leu Ser Gly Trp Ala Ala Ser
            20                  25

<210> SEQ ID NO 557
<211> LENGTH: 24
<212> TYPE: PRT
<213> ORGANISM: Homo sapiens

<400> SEQUENCE: 557

Met Gly Leu Pro Arg Gly Pro Leu Ala Ser Leu Leu Leu Leu Gln Val
1               5                   10                  15

Cys Trp Leu Gln Cys Ala Ala Ser
            20

<210> SEQ ID NO 558
<211> LENGTH: 26
<212> TYPE: PRT
<213> ORGANISM: Homo sapiens

<400> SEQUENCE: 558

Gly Gly Ile Pro Gly Asp Leu Arg Val Ala Thr Val Thr Leu Met Leu
1               5                   10                  15

Ala Ile Leu Ser Ser Ser Leu Ala Glu Gly
            20                  25

<210> SEQ ID NO 559
<211> LENGTH: 24
<212> TYPE: PRT
<213> ORGANISM: Homo sapiens

<400> SEQUENCE: 559

Met Ala Val Met Ala Pro Arg Thr Leu Leu Leu Leu Leu Ser Gly Ala
1               5                   10                  15

Leu Ala Leu Thr Gln Thr Trp Ala
            20
```

-continued

```
<210> SEQ ID NO 560
<211> LENGTH: 24
<212> TYPE: PRT
<213> ORGANISM: Homo sapiens

<400> SEQUENCE: 560

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 561
<211> LENGTH: 24
<212> TYPE: PRT
<213> ORGANISM: Homo sapiens

<400> SEQUENCE: 561

Met Ala Val Met Ala Pro Arg Thr Leu Leu Leu Leu Ser Gly Ala
1               5                   10                  15

Leu Ala Leu Thr Gln Thr Trp Ala
            20

<210> SEQ ID NO 562
<211> LENGTH: 26
<212> TYPE: PRT
<213> ORGANISM: Homo sapiens

<400> SEQUENCE: 562

Met Lys His Thr Leu Ala Leu Leu Ala Pro Leu Leu Gly Leu Gly Leu
1               5                   10                  15

Gly Leu Ala Leu Ser Gln Leu Ala Ala Gly
            20                  25

<210> SEQ ID NO 563
<211> LENGTH: 24
<212> TYPE: PRT
<213> ORGANISM: Homo sapiens

<400> SEQUENCE: 563

Met Glu Leu Leu Pro Pro Leu Pro Gln Ser Phe Leu Leu Leu Leu Leu
1               5                   10                  15

Leu Pro Ala Lys Pro Ala Ala Gly
            20

<210> SEQ ID NO 564
<211> LENGTH: 23
<212> TYPE: PRT
<213> ORGANISM: Homo sapiens

<400> SEQUENCE: 564

Met Gln Ser Pro Trp Lys Ile Leu Thr Val Ala Pro Leu Phe Leu Leu
1               5                   10                  15

Leu Ser Leu Gln Ser Ser Ala
            20

<210> SEQ ID NO 565
<211> LENGTH: 23
<212> TYPE: PRT
<213> ORGANISM: Homo sapiens

<400> SEQUENCE: 565

Met Gln Pro Pro Ser Leu Leu Leu Leu Leu Leu Leu Leu Leu Leu
1               5                   10                  15
```

Cys Val Ser Val Val Arg Pro
            20

<210> SEQ ID NO 566
<211> LENGTH: 22
<212> TYPE: PRT
<213> ORGANISM: Homo sapiens

<400> SEQUENCE: 566

Met Arg Thr Pro Gln Leu Ala Leu Leu Gln Val Phe Phe Leu Val Phe
1               5                   10                  15

Pro Asp Gly Val Arg Pro
            20

<210> SEQ ID NO 567
<211> LENGTH: 24
<212> TYPE: PRT
<213> ORGANISM: Homo sapiens

<400> SEQUENCE: 567

Met Ala Arg Gln Pro Pro Pro Trp Val His Ala Ala Phe Leu Leu
1               5                   10                  15

Cys Leu Leu Ser Leu Gly Gly Ala
            20

<210> SEQ ID NO 568
<211> LENGTH: 22
<212> TYPE: PRT
<213> ORGANISM: Homo sapiens

<400> SEQUENCE: 568

Met Asp Val Cys Val Arg Leu Ala Leu Trp Leu Leu Trp Gly Leu Leu
1               5                   10                  15

Leu His Gln Gly Gln Ser
            20

<210> SEQ ID NO 569
<211> LENGTH: 21
<212> TYPE: PRT
<213> ORGANISM: Homo sapiens

<400> SEQUENCE: 569

Met Gln Phe Arg Leu Phe Ser Phe Ala Leu Ile Ile Leu Asn Cys Met
1               5                   10                  15

Asp Tyr Ser His Cys
            20

<210> SEQ ID NO 570
<211> LENGTH: 25
<212> TYPE: PRT
<213> ORGANISM: Homo sapiens

<400> SEQUENCE: 570

Met Gly Ser Arg Gly Gln Gly Leu Leu Leu Ala Tyr Cys Leu Leu Leu
1               5                   10                  15

Ala Phe Ala Ser Gly Leu Val Leu Ser
            20                  25

<210> SEQ ID NO 571
<211> LENGTH: 24
<212> TYPE: PRT
<213> ORGANISM: Homo sapiens

```
<400> SEQUENCE: 571

Met Phe Leu Ala Thr Leu Tyr Phe Ala Leu Pro Leu Leu Asp Leu Leu
1               5                   10                  15

Leu Ser Ala Glu Val Ser Gly Gly
            20

<210> SEQ ID NO 572
<211> LENGTH: 22
<212> TYPE: PRT
<213> ORGANISM: Homo sapiens

<400> SEQUENCE: 572

Met Gln Arg Leu Val Leu Leu Ala Ile Ser Leu Leu Tyr Gln
1               5                   10                  15

Asp Leu Pro Val Arg Ser
            20

<210> SEQ ID NO 573
<211> LENGTH: 23
<212> TYPE: PRT
<213> ORGANISM: Homo sapiens

<400> SEQUENCE: 573

Met Arg Leu Trp Lys Ala Val Val Val Thr Leu Ala Phe Met Ser Val
1               5                   10                  15

Asp Ile Cys Val Thr Thr Ala
            20

<210> SEQ ID NO 574
<211> LENGTH: 23
<212> TYPE: PRT
<213> ORGANISM: Homo sapiens

<400> SEQUENCE: 574

Met Arg Gln Lys Ala Val Ser Leu Phe Leu Cys Tyr Leu Leu Leu Phe
1               5                   10                  15

Thr Cys Ser Gly Val Glu Ala
            20

<210> SEQ ID NO 575
<211> LENGTH: 25
<212> TYPE: PRT
<213> ORGANISM: Homo sapiens

<400> SEQUENCE: 575

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 576
<211> LENGTH: 23
<212> TYPE: PRT
<213> ORGANISM: Homo sapiens

<400> SEQUENCE: 576

Met Leu Phe Arg Asn Arg Phe Leu Leu Leu Ala Leu Ala Ala Leu
1               5                   10                  15

Leu Ala Phe Val Ser Leu Ser
            20
```

<210> SEQ ID NO 577
<211> LENGTH: 24
<212> TYPE: PRT
<213> ORGANISM: Homo sapiens

<400> SEQUENCE: 577

Met Leu Pro Leu Pro Ser Cys Ser Leu Pro Ile Leu Leu Leu Phe Leu
1               5                   10                  15

Leu Pro Ser Val Pro Ile Glu Ser
            20

<210> SEQ ID NO 578
<211> LENGTH: 23
<212> TYPE: PRT
<213> ORGANISM: Homo sapiens

<400> SEQUENCE: 578

Met Lys Ala Met Pro Trp Asn Trp Thr Cys Leu Leu Ser His Leu Leu
1               5                   10                  15

Met Val Gly Met Gly Ser Ser
            20

<210> SEQ ID NO 579
<211> LENGTH: 27
<212> TYPE: PRT
<213> ORGANISM: Homo sapiens

<400> SEQUENCE: 579

Met Ala Leu Gly Lys Val Leu Ala Met Ala Leu Val Leu Ala Leu Ala
1               5                   10                  15

Val Leu Gly Ser Leu Ser Pro Gly Ala Arg Ala
            20                  25

<210> SEQ ID NO 580
<211> LENGTH: 24
<212> TYPE: PRT
<213> ORGANISM: Homo sapiens

<400> SEQUENCE: 580

Met Val Pro Ser Ser Pro Arg Ala Leu Phe Leu Leu Leu Ile Leu
1               5                   10                  15

Ala Cys Pro Glu Pro Arg Ala Ser
            20

<210> SEQ ID NO 581
<211> LENGTH: 25
<212> TYPE: PRT
<213> ORGANISM: Homo sapiens

<400> SEQUENCE: 581

Met Cys Arg Ile Ala Gly Ala Leu Arg Thr Leu Leu Pro Leu Leu Ala
1               5                   10                  15

Ala Leu Leu Gln Ala Ser Val Glu Ala
            20                  25

<210> SEQ ID NO 582
<211> LENGTH: 24
<212> TYPE: PRT
<213> ORGANISM: Homo sapiens

<400> SEQUENCE: 582

Met Asn Asn Phe Arg Ala Thr Ile Leu Phe Trp Ala Ala Ala Ala Trp

-continued

```
                1               5                  10                 15

Ala Lys Ser Gly Lys Pro Ser Gly
            20

<210> SEQ ID NO 583
<211> LENGTH: 24
<212> TYPE: PRT
<213> ORGANISM: Homo sapiens

<400> SEQUENCE: 583

Met Ala Val Trp Leu Ala Gln Trp Leu Gly Pro Leu Leu Val Ser
1               5                  10                 15

Leu Trp Gly Leu Leu Ala Pro Ala
            20

<210> SEQ ID NO 584
<211> LENGTH: 25
<212> TYPE: PRT
<213> ORGANISM: Homo sapiens

<400> SEQUENCE: 584

Met Glu Ala Ala Arg Ala Leu Arg Leu Leu Val Val Cys Gly Cys
1               5                  10                 15

Leu Ala Leu Pro Pro Leu Ala Glu Pro
            20                  25

<210> SEQ ID NO 585
<211> LENGTH: 24
<212> TYPE: PRT
<213> ORGANISM: Homo sapiens

<400> SEQUENCE: 585

Met Asp Leu Gly Lys Pro Met Lys Ser Val Leu Val Val Ala Leu Leu
1               5                  10                 15

Val Ile Phe Gln Val Cys Leu Cys
            20

<210> SEQ ID NO 586
<211> LENGTH: 26
<212> TYPE: PRT
<213> ORGANISM: Homo sapiens

<400> SEQUENCE: 586

Met Pro Ser Leu Pro Ala Pro Pro Ala Pro Leu Leu Leu Gly Leu
1               5                  10                 15

Leu Leu Leu Gly Ser Arg Pro Ala Arg Gly
            20                  25

<210> SEQ ID NO 587
<211> LENGTH: 24
<212> TYPE: PRT
<213> ORGANISM: Homo sapiens

<400> SEQUENCE: 587

Met Arg Val Met Ala Pro Arg Thr Leu Ile Leu Leu Leu Ser Gly Ala
1               5                  10                 15

Leu Ala Leu Thr Glu Thr Trp Ala
            20

<210> SEQ ID NO 588
<211> LENGTH: 24
<212> TYPE: PRT
```

-continued

<213> ORGANISM: Homo sapiens

<400> SEQUENCE: 588

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 589
<211> LENGTH: 24
<212> TYPE: PRT
<213> ORGANISM: Homo sapiens

<400> SEQUENCE: 589

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 590
<211> LENGTH: 24
<212> TYPE: PRT
<213> ORGANISM: Homo sapiens

<400> SEQUENCE: 590

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 591
<211> LENGTH: 24
<212> TYPE: PRT
<213> ORGANISM: Homo sapiens

<400> SEQUENCE: 591

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 592
<211> LENGTH: 25
<212> TYPE: PRT
<213> ORGANISM: Homo sapiens

<400> SEQUENCE: 592

Met Thr Ser Cys Gly Gln Gln Ser Leu Asn Val Leu Ala Val Leu Phe
1               5                   10                  15

Ser Leu Leu Phe Ser Ala Val Leu Ser
            20                  25

<210> SEQ ID NO 593
<211> LENGTH: 24
<212> TYPE: PRT
<213> ORGANISM: Homo sapiens

<400> SEQUENCE: 593

Met Ala Thr Arg Ser Val Leu Leu Ala Leu Val Val Leu Asn Leu Leu
1               5                   10                  15

Phe Tyr Val Pro Pro Gly Arg Ser
            20

<210> SEQ ID NO 594
<211> LENGTH: 24
<212> TYPE: PRT
<213> ORGANISM: Homo sapiens

<400> SEQUENCE: 594

Met Ala Arg Phe Leu Thr Leu Cys Thr Trp Leu Leu Leu Gly Pro
1               5                   10                  15

Gly Leu Leu Ala Thr Val Arg Ala
            20

<210> SEQ ID NO 595
<211> LENGTH: 23
<212> TYPE: PRT
<213> ORGANISM: Homo sapiens

<400> SEQUENCE: 595

Met His Thr Leu Thr Gly Phe Ser Leu Val Ser Leu Leu Ser Phe Gly
1               5                   10                  15

Tyr Leu Ser Trp Asp Trp Ala
            20

<210> SEQ ID NO 596
<211> LENGTH: 21
<212> TYPE: PRT
<213> ORGANISM: Homo sapiens

<400> SEQUENCE: 596

Met His Trp Gly Thr Leu Cys Gly Phe Leu Trp Leu Trp Pro Tyr Leu
1               5                   10                  15

Phe Tyr Val Gln Ala
            20

<210> SEQ ID NO 597
<211> LENGTH: 24
<212> TYPE: PRT
<213> ORGANISM: Homo sapiens

<400> SEQUENCE: 597

Met Val Val Met Ala Pro Arg Thr Leu Phe Leu Leu Leu Ser Gly Ala
1               5                   10                  15

Leu Thr Leu Thr Glu Thr Trp Ala
            20

<210> SEQ ID NO 598
<211> LENGTH: 23
<212> TYPE: PRT
<213> ORGANISM: Homo sapiens

<400> SEQUENCE: 598

Met Ile Ser Ser Val Lys Leu Asn Leu Ile Leu Val Leu Ser Leu Ser
1               5                   10                  15

Thr Met His Val Phe Trp Cys
            20

<210> SEQ ID NO 599
<211> LENGTH: 26
<212> TYPE: PRT
<213> ORGANISM: Homo sapiens

<400> SEQUENCE: 599

Met Gln Gly Arg Val Ala Gly Ser Cys Ala Pro Leu Gly Leu Leu Leu
1               5                   10                  15

Val Cys Leu His Leu Pro Gly Leu Phe Ala
            20                  25

<210> SEQ ID NO 600
<211> LENGTH: 26
<212> TYPE: PRT
<213> ORGANISM: Homo sapiens

<400> SEQUENCE: 600

Met Thr Pro Pro Lys Leu Arg Ala Ser Leu Ser Pro Ser Leu Leu Leu
1               5                   10                  15

Leu Leu Ser Gly Cys Leu Leu Ala Ala Ala
            20                  25

<210> SEQ ID NO 601
<211> LENGTH: 22
<212> TYPE: PRT
<213> ORGANISM: Homo sapiens

<400> SEQUENCE: 601

Met Asn Tyr Ser Ser Phe Leu Arg Ile Trp Val Ser Phe Ile Phe Ala
1               5                   10                  15

Leu Val Gln His Gln Ala
            20

<210> SEQ ID NO 602
<211> LENGTH: 27
<212> TYPE: PRT
<213> ORGANISM: Homo sapiens

<400> SEQUENCE: 602

Met Arg Pro Arg Ala Pro Ala Cys Ala Ala Ala Leu Gly Leu Cys
1               5                   10                  15

Ser Leu Leu Leu Leu Ala Pro Gly His Ala
            20                  25

<210> SEQ ID NO 603
<211> LENGTH: 25
<212> TYPE: PRT
<213> ORGANISM: Homo sapiens

<400> SEQUENCE: 603

Met Met Ser Pro Ser Gln Ala Ser Leu Leu Phe Leu Asn Val Cys Ile
1               5                   10                  15

Phe Ile Cys Gly Glu Ala Val Gln Gly
            20                  25

<210> SEQ ID NO 604
<211> LENGTH: 24
<212> TYPE: PRT
<213> ORGANISM: Homo sapiens

<400> SEQUENCE: 604

Met Ala Val Ser Gln Gly Asp Gly Thr Leu Cys Phe Val Leu Leu Leu
1               5                   10                  15

Cys Cys Trp Gln Glu Thr Glu Leu
            20

<210> SEQ ID NO 605
<211> LENGTH: 24

```
<212> TYPE: PRT
<213> ORGANISM: Homo sapiens

<400> SEQUENCE: 605

Met Lys Met Gln Lys Gly Asn Val Leu Leu Met Phe Gly Leu Leu Leu
1               5                   10                  15

His Leu Glu Ala Ala Thr Asn Ser
            20

<210> SEQ ID NO 606
<211> LENGTH: 27
<212> TYPE: PRT
<213> ORGANISM: Homo sapiens

<400> SEQUENCE: 606

Met Pro Ser Ser Thr Ala Met Ala Val Gly Ala Leu Ser Ser Ser Leu
1               5                   10                  15

Leu Val Thr Cys Cys Leu Met Val Ala Leu Cys
            20                  25

<210> SEQ ID NO 607
<211> LENGTH: 24
<212> TYPE: PRT
<213> ORGANISM: Homo sapiens

<400> SEQUENCE: 607

Met Ala Gln Arg Met Thr Thr Gln Leu Leu Leu Leu Val Trp Val
1               5                   10                  15

Ala Val Val Gly Glu Ala Gln Thr
            20

<210> SEQ ID NO 608
<211> LENGTH: 24
<212> TYPE: PRT
<213> ORGANISM: Homo sapiens

<400> SEQUENCE: 608

Met Arg Leu Leu Val Leu Ser Ser Leu Leu Cys Ile Leu Leu Leu Cys
1               5                   10                  15

Phe Ser Ile Phe Ser Thr Glu Gly
            20

<210> SEQ ID NO 609
<211> LENGTH: 25
<212> TYPE: PRT
<213> ORGANISM: Homo sapiens

<400> SEQUENCE: 609

Met Ala Ala Ala Ala Ile Pro Ala Leu Leu Leu Cys Leu Pro Leu Leu
1               5                   10                  15

Phe Leu Leu Phe Gly Trp Ser Arg Ala
            20                  25

<210> SEQ ID NO 610
<211> LENGTH: 25
<212> TYPE: PRT
<213> ORGANISM: Homo sapiens

<400> SEQUENCE: 610

Met Glu Arg Pro Leu Cys Ser His Leu Cys Ser Cys Leu Ala Met Leu
1               5                   10                  15

Ala Leu Leu Ser Pro Leu Ser Leu Ala
```

<210> SEQ ID NO 611
<211> LENGTH: 25
<212> TYPE: PRT
<213> ORGANISM: Homo sapiens

<400> SEQUENCE: 611

Met Pro Ala Leu Arg Pro Ala Leu Leu Trp Ala Leu Leu Ala Leu Trp
1               5                   10                  15

Leu Cys Cys Ala Ala Pro Ala His Ala
            20                  25

<210> SEQ ID NO 612
<211> LENGTH: 23
<212> TYPE: PRT
<213> ORGANISM: Homo sapiens

<400> SEQUENCE: 612

Met Glu Ser Gly His Leu Leu Trp Ala Leu Leu Phe Met Gln Ser Leu
1               5                   10                  15

Trp Pro Gln Leu Thr Asp Gly
            20

<210> SEQ ID NO 613
<211> LENGTH: 25
<212> TYPE: PRT
<213> ORGANISM: Homo sapiens

<400> SEQUENCE: 613

Met Gly Gly Cys Thr Val Lys Pro Gln Leu Leu Leu Ala Leu Val
1               5                   10                  15

Leu His Pro Trp Asn Pro Cys Leu Gly
            20                  25

<210> SEQ ID NO 614
<211> LENGTH: 24
<212> TYPE: PRT
<213> ORGANISM: Homo sapiens

<400> SEQUENCE: 614

Met Ala Leu Ser Ser Ala Trp Arg Ser Val Leu Pro Leu Trp Leu Leu
1               5                   10                  15

Trp Ser Ala Ala Cys Ser Arg Ala
            20

<210> SEQ ID NO 615
<211> LENGTH: 24
<212> TYPE: PRT
<213> ORGANISM: Homo sapiens

<400> SEQUENCE: 615

Met Trp Gly Phe Arg Leu Leu Arg Ser Pro Leu Leu Leu Leu Leu
1               5                   10                  15

Pro Gln Leu Gly Ile Gly Asn Ala
            20

<210> SEQ ID NO 616
<211> LENGTH: 24
<212> TYPE: PRT
<213> ORGANISM: Homo sapiens

<400> SEQUENCE: 616

Met Ala Thr Ser Thr Gly Arg Trp Leu Leu Arg Leu Ala Leu Phe
1               5                   10                  15

Gly Phe Leu Trp Glu Ala Ser Gly
            20

<210> SEQ ID NO 617
<211> LENGTH: 25
<212> TYPE: PRT
<213> ORGANISM: Homo sapiens

<400> SEQUENCE: 617

Met Ala Trp Gly Gly Val His Thr Cys Cys Phe His Leu Cys Cys
1               5                   10                  15

Cys Ser Trp Pro Gln Gly Ala Val Pro
            20                  25

<210> SEQ ID NO 618
<211> LENGTH: 24
<212> TYPE: PRT
<213> ORGANISM: Homo sapiens

<400> SEQUENCE: 618

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 619
<211> LENGTH: 29
<212> TYPE: PRT
<213> ORGANISM: Homo sapiens

<400> SEQUENCE: 619

Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala
            20                  25

<210> SEQ ID NO 620
<211> LENGTH: 24
<212> TYPE: PRT
<213> ORGANISM: Homo sapiens

<400> SEQUENCE: 620

Met Leu Ala Ala Ser Ile Phe Arg Pro Thr Leu Leu Leu Cys Trp Leu
1               5                   10                  15

Ala Ala Pro Trp Pro Thr Gln Pro
            20

<210> SEQ ID NO 621
<211> LENGTH: 25
<212> TYPE: PRT
<213> ORGANISM: Homo sapiens

<400> SEQUENCE: 621

Met Arg Gln Arg Leu Leu Pro Ser Val Thr Ser Leu Leu Leu Val Ala
1               5                   10                  15

Leu Leu Phe Pro Gly Ser Ser Gln Ala
            20                  25

<210> SEQ ID NO 622

```
<211> LENGTH: 30
<212> TYPE: PRT
<213> ORGANISM: Homo sapiens

<400> SEQUENCE: 622

Met Glu Ala Gly Glu Gly Lys Glu Arg Val Pro Lys Gln Arg Gln Val
1               5                   10                  15

Leu Ile Phe Phe Val Leu Leu Gly Ile Ala Gln Ala Ser Cys
            20                  25                  30

<210> SEQ ID NO 623
<211> LENGTH: 30
<212> TYPE: PRT
<213> ORGANISM: Homo sapiens

<400> SEQUENCE: 623

Met Ala Arg Phe Pro Lys Ala Asp Leu Ala Ala Ala Gly Val Met Leu
1               5                   10                  15

Leu Cys His Phe Phe Thr Asp Gln Phe Gln Phe Ala Asp Gly
            20                  25                  30

<210> SEQ ID NO 624
<211> LENGTH: 29
<212> TYPE: PRT
<213> ORGANISM: Homo sapiens

<400> SEQUENCE: 624

Met Asp Tyr His Trp Arg Gly Glu Leu Gly Ser Trp Arg Leu Leu Leu
1               5                   10                  15

Leu Leu Leu Leu Leu Ala Ala Trp Lys Val Gly Ser Gly
            20                  25
```